US007985415B2

(12) United States Patent
Giroux

(10) Patent No.: US 7,985,415 B2
(45) Date of Patent: Jul. 26, 2011

(54) MEDICAL DEVICES EMPLOYING NOVEL POLYMERS

(75) Inventor: Karen J. Giroux, Piscataway, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 1422 days.

(21) Appl. No.: 10/716,577

(22) Filed: Nov. 18, 2003

(65) Prior Publication Data

US 2006/0188546 A1    Aug. 24, 2006

Related U.S. Application Data

(63) Continuation-in-part of application No. 10/273,244, filed on Oct. 17, 2002, now abandoned, which is a continuation of application No. 09/627,215, filed on Jul. 27, 2000, now Pat. No. 6,486,214, which is a continuation-in-part of application No. 09/422,294, filed on Oct. 21, 1999, now Pat. No. 6,468,519, which is a continuation-in-part of application No. PCT/US98/18816, filed on Sep. 10, 1998, application No. 10/716,577, which is a continuation-in-part of application No. 09/917,914, filed on Jul. 27, 2001, now Pat. No. 6,689,350.

(60) Provisional application No. 60/427,476, filed on Nov. 18, 2002, provisional application No. 60/261,337, filed on Jan. 12, 2001, provisional application No. 60/220,707, filed on Jul. 27, 2000, provisional application No. 60/058,328, filed on Sep. 10, 1997.

(51) Int. Cl.
*A61F 2/00*    (2006.01)

(52) U.S. Cl. ...................................................... 424/426
(58) Field of Classification Search .................. 424/426
See application file for complete search history.

(56) References Cited

U.S. PATENT DOCUMENTS

| 5,464,650 | A * | 11/1995 | Berg et al. .................. 427/2.3 |
| 6,107,416 | A | 8/2000 | Patnaik et al. |
| 6,110,453 | A | 8/2000 | Keefer et al. |
| 6,174,539 | B1 | 1/2001 | Stamler et al. |
| 6,197,051 | B1 | 3/2001 | Zhong |
| 6,218,016 | B1 | 4/2001 | Tedeschi et al. |

(Continued)

FOREIGN PATENT DOCUMENTS

CA    2124852    6/1993

(Continued)

OTHER PUBLICATIONS

European Search Report, European Application No. 03 78 6836, dated Mar. 19, 2008.

(Continued)

*Primary Examiner* — Blessing M Fubara
(74) *Attorney, Agent, or Firm* — Viksnins Harris & Padys PLLP

(57) ABSTRACT

Medical devices with at least one surface comprising a polymer or polymers on the surface are provided. The polymer or polymers are capable of breaking down (e.g., including, but not limited to, hydrolyzing) in the physiologic milieu to form an active agent or agents under physiologic conditions, and can contain other active agents dispersed within or appended to the polymer matrix. Methods of delivering an active agent to an interior surface of a vein or artery are also provided.

14 Claims, 29 Drawing Sheets

U.S. PATENT DOCUMENTS

| | | |
|---|---|---|
| 6,395,021 B1 | 5/2002 | Hart et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich |
| 6,689,350 B2 | 2/2004 | Uhrich |
| 6,730,064 B2 * | 5/2004 | Ragheb et al. ............ 604/265 |
| 7,122,615 B1 | 10/2006 | Uhrich |
| 7,396,527 B2 | 7/2008 | Uhrich |
| 7,411,031 B2 | 8/2008 | Uhrich |
| 7,534,852 B2 | 5/2009 | Uhrich |
| 7,662,864 B2 | 2/2010 | Kanamathareddy et al. |
| 7,666,398 B2 | 2/2010 | Uhrich |
| 2002/0028243 A1 | 3/2002 | Masters |
| 2003/0035787 A1 | 2/2003 | Uhrich |
| 2004/0038948 A1 | 2/2004 | Uhrich |
| 2004/0096476 A1 | 5/2004 | Uhrich |
| 2005/0048121 A1 | 3/2005 | East |
| 2005/0089506 A1 | 4/2005 | Uhrich |
| 2005/0249697 A1 | 11/2005 | Uhrich |
| 2006/0013851 A1 | 1/2006 | Giroux |
| 2006/0057179 A1 | 3/2006 | Giroux |
| 2007/0014832 A1 | 1/2007 | Uhrich |
| 2007/0098800 A1 | 5/2007 | Giroux |
| 2007/0196417 A1 | 8/2007 | Uhrich |
| 2007/0213500 A1 | 9/2007 | Uhrich |
| 2008/0226583 A1 | 9/2008 | Uhrich |
| 2008/0233078 A1 | 9/2008 | Uhrich |
| 2008/0234235 A1 | 9/2008 | Uhrich |
| 2009/0035248 A1 | 2/2009 | Uhrich et al. |
| 2010/0074937 A1 | 3/2010 | Uhrich |
| 2010/0152410 A1 | 6/2010 | East et al. |

FOREIGN PATENT DOCUMENTS

| | | |
|---|---|---|
| EP | 0716836 | 6/1996 |
| JP | H06-172426 | 6/1994 |
| JP | H07-70233 | 3/1995 |
| JP | H08-224297 | 9/1996 |
| WO | WO 99/12990 * | 3/1999 |
| WO | WO-99/12990 A1 | 3/1999 |
| WO | WO 01/28492 | 4/2001 |
| WO | WO 01/41753 | 6/2001 |
| WO | WO 02/09767 | 2/2002 |
| WO | WO 02/09768 | 2/2002 |
| WO | WO 02/09768 A2 * | 2/2002 |
| WO | WO 02/09769 | 2/2002 |
| WO | WO 02/056790 * | 7/2002 |
| WO | WO 02/56790 A2 * | 7/2002 |
| WO | WO-02/056790 A2 | 7/2002 |
| WO | WO 02/087586 | 11/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |

OTHER PUBLICATIONS

Woo, G.L.Y., et al., "Synthesis and characterization of a novel biodegradable antimicrobial polymer", *Biomaterials, 21*, 1235-1246, (2000).

* cited by examiner

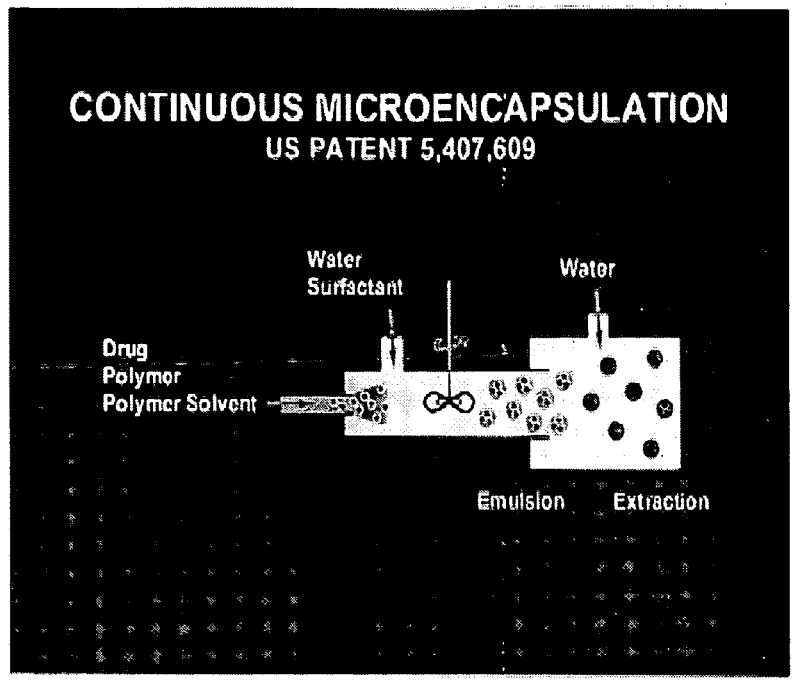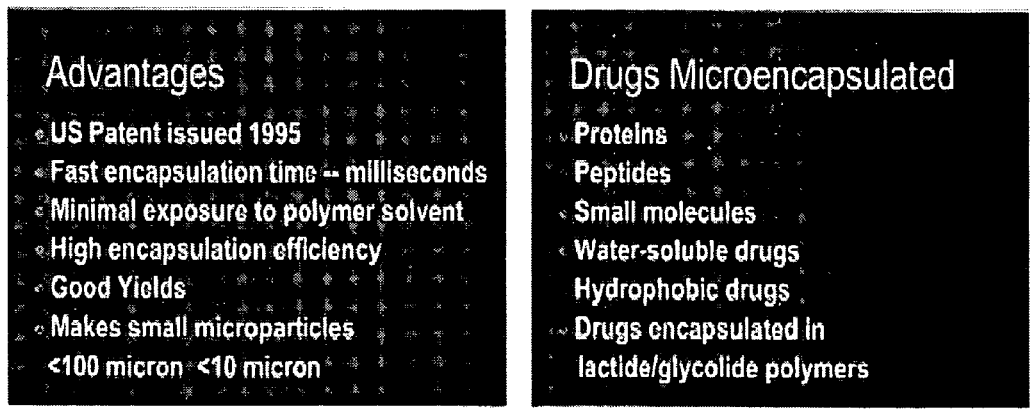
Figure 1

Conditions: Ambient

| Material: | PX510 | PX261 | PX749 | PX125 | PX510 + 14% Paclitaxel |
|---|---|---|---|---|---|
| Hardness: | F | B | 3B | 4B | F |

Conditions: 5 minutes in 37°C pH 7.4 Saline Buffer

| Material: | PX510 | PX261 | PX749 | PX125 | PX510 + 14% Paclitaxel |
|---|---|---|---|---|---|
| Hardness: | F | B | 9B | <9B | F |

Hardness Rating: 2H-H-F-HB-B-2B-3B-4B-5B-6B-7B-8B-9B

Harder ⟵ ⟶ Softer

Figure 5

Conditions: Ambient

| Material: | PX510 | PX261 | PX749 | PX125 | PX510 + 14% Paclitaxel |
|---|---|---|---|---|---|
| Resistance To Cracking | < 3 mm | < 3 mm | < 3mm | < 3mm | <3mm |

Conditions: 5 minutes in 37°C pH 7.4 Saline Buffer

| Material: | PX510 | PX261 | PX749 | PX125 | PX510 + 14% Paclitaxel |
|---|---|---|---|---|---|
| Resistance To Cracking | < 3 mm | < 3 mm | < 3mm | < 3mm | < 3mm |

Figure 6

Conditions: Ambient

| Material: | PX510 | PX261 | PX749 | PX125 | PX510 + 14% Paclitaxel |
|---|---|---|---|---|---|
| Class: | 5B | 5B | 5B | 4B | 5B |

Class Rating: 5B = 0% of coating removed from substrate
4B = Less than 5% of coating removed from substrate

Figure 7

|  | Formulation | | | |
| --- | --- | --- | --- | --- |
| Property | PX510 | PX721 | PX261 | PX749 |
| $T_g$ (°C) | 44 | 38 | 29 | 16 |
| Tensile modulus (MPa) | 2.0 (25 °C)<br>5.1 (37 °C) | | | 3.0 (25 °C) |
| Yield Strength (MPa) | Not observed | | | 6.0 (25 °C) |
| Ultimate Elongation (%) | 1.5 (25 °C)<br>350 (37 °C) | | | 500 (25 °C) |

Figure 10

|  | E Beam (3 MRad) | | | γ (25-35 KGys) | | |
| --- | --- | --- | --- | --- | --- | --- |
| Property | PX510 | PX721 | PX261 | PX510 | PX721 | PX261 |
| MW | -26% | -39% | -26% | -14% | N/C | N/C |
| Hardness | -2 units | N/C | -1 unit | N/C | -3 units | -2 units |
| Flexibility | N/C | N/C | N/C | N/C | N/C | N/C |
| Adhesion | N/C | N/C | -1 unit | N/C | N/C | N/C |

N/C: no change

Figure 12

Thermoanalysis of PolyAspirin™

| Property | PolyAspirin I | PolyAspirin II | |
|---|---|---|---|
| | PX261 | PX657 | |
| | Mw ~ 20K | $M_w$ ~ 33K | $M_w$ ~ 100K |
| $T_g$ (°C) | 29 | 36 | 44 |
| Ultimate Stress (kPa) | 1700 (25°C)<br>>2000 (37°C) | >2800 (25°C) | >2600 (25°C) |
| Ultimate Elongation (%) | >500 (25°C)<br>>500 (37°C) | >4 (25°C) | >500 (25°C) |
| Toughness (kPa) | >3900 (25°C)<br>>4400 (37°C) | >560 (25°C) | >4000 (25°C) |

Figure 21

Properties of PolyAspirin™ Coatings

|  | PolyAspirin I | PolyAspirin II | |
|---|---|---|---|
| Test | PX261<br>Mw ~ 20K | PX657<br>Mw ~ 33K | Mw ~ 100K |
| Hardness | | | |
| Ambient | B | F | 3H |
| 5 min in PBS, 37 °C | B | 2B | B |
| 1 hr in PBS, 37 °C | - | 8B | 4B |
| Flexibility | | | |
| Ambient | <3 mm | <3 mm | <3 mm |
| 5 min in PBS, 37 °C | <3 mm | <3 mm | <3 mm |
| 1 hr in PBS, 37 °C | | <3 mm | <3 mm |
| Adhesion | | | |
| Ambient | 5B | 5B | 5B |

Figure 22

PolyAspirin Coatings with Admixtures

| Test | PolyAspirin II (PX657) | |
|---|---|---|
| | No Admixture | 20% Paclitaxel Admixed |
| Hardness | | |
| Ambient | F | F |
| 5 min in PBS, 37 °C | 2B | F |
| 1 hr in PBS, 37 °C | 8B | 6B |
| Flexibility | | |
| Ambient | <3 mm | <3 mm |
| 5 min in PBS, 37 °C | <3 mm | <3 mm |
| 1 hr in PBS, 37 °C | <3 mm | <3 mm |
| Adhesion | | |
| Ambient | 5B | 5B |

Figure 23

Erosion of PolyAspirin I & II

Diflunisal Generation & Paclitaxel Release into 37 °C Serum from ~5 µm-thick Coatings on 316L SS Plates Erosion of Sterilized PolyAspirin II Generation of Diflunisal into 37 °C Serum from ~5 μm-thick Coatings on 316L SS Plates γ Irradiation (25-35 Kgys)

| Property | PolyAspirin I<br>PX261<br>$M_w \sim 20K$ | PolyAspirin II<br>PX657<br>$M_w \sim 100K$ |
| --- | --- | --- |
| MW | N/C | -50% |
| Hardness | -2 units | -3 units |
| Flexibility | N/C | - |
| Adhesion | N/C | - |

N/C: no change

Figure 26

E Beam (3-4.5 MRad)

| Property | PolyAspirin I<br>PX261<br>$M_w \sim 20 K$ | PolyAspirin II<br>PX657<br>$M_w \sim 33K$ | PolyAspirin II<br>PX657<br>$M_w \sim 80K$ |
| --- | --- | --- | --- |
| MW | -26% | +5% | -30% |
| Hardness | -1 unit | +2 units | N/C |
| Flexibility | N/C | - | N/C |
| Adhesion | -1 unit | - | - |

Figure 27

Figure 33
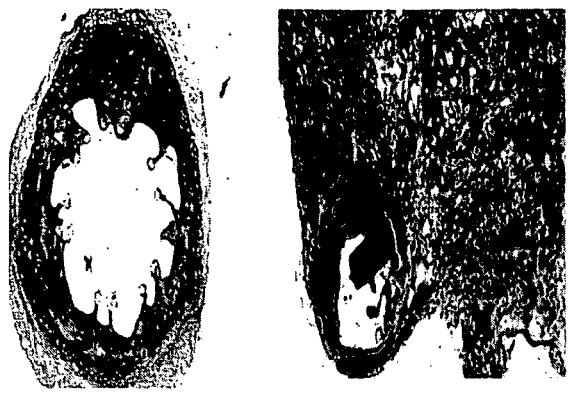
Figure 34
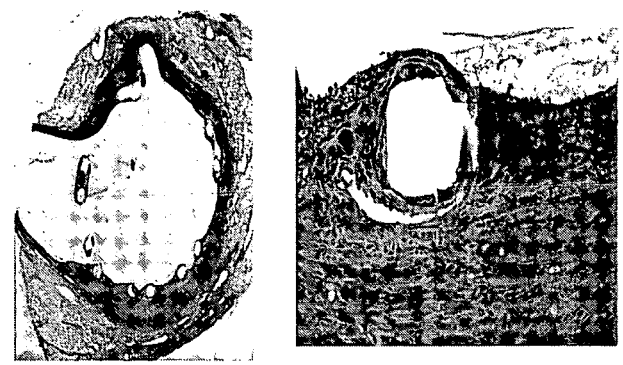
Figure 35
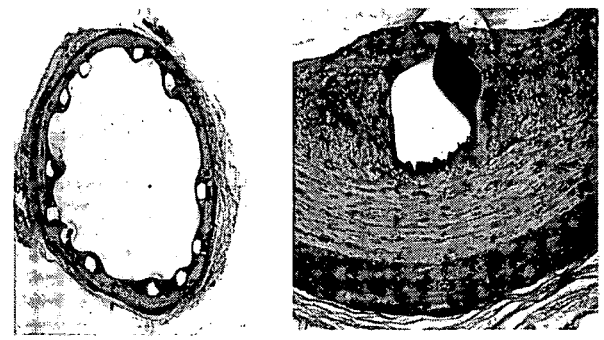
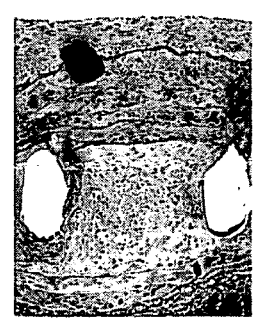

uncrimped/unexpanded
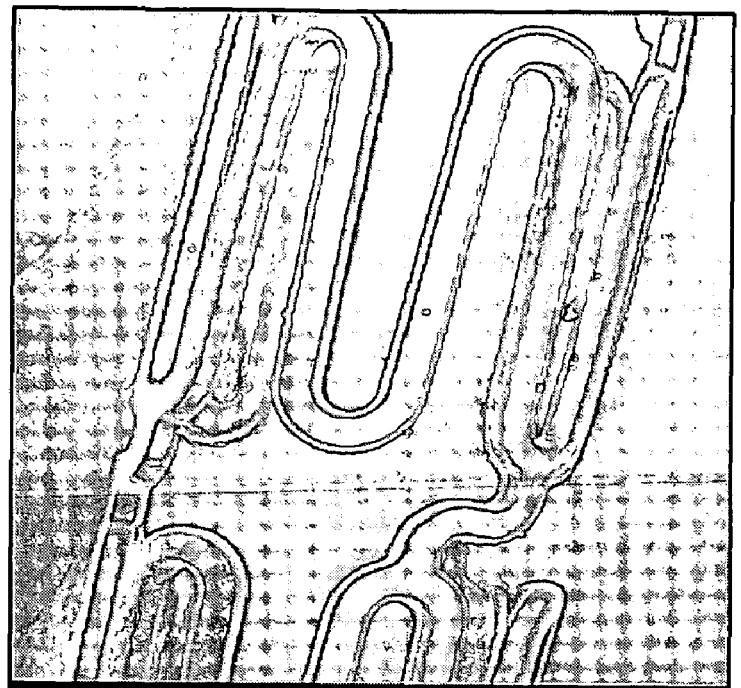
Fig. 44a
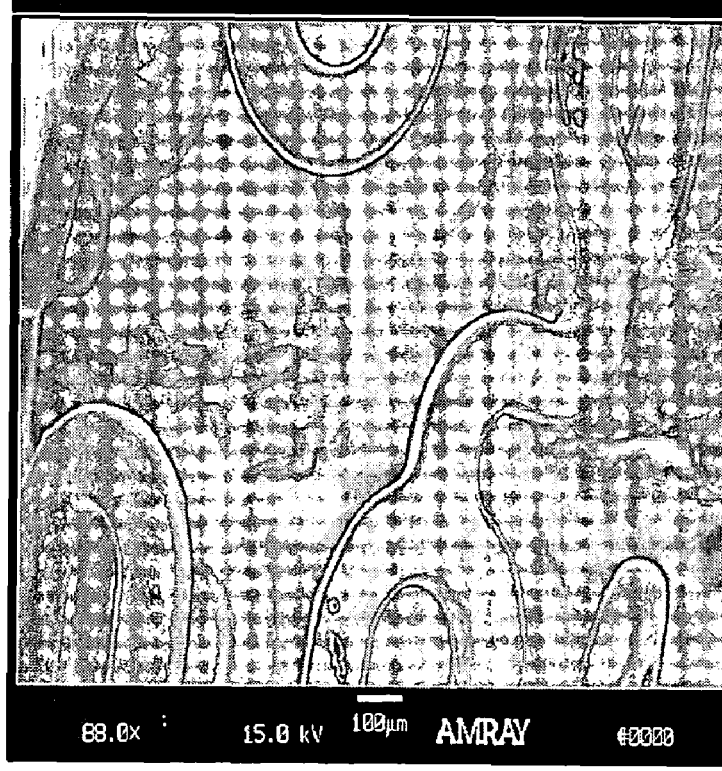
Fig. 44b
Figure 44 uncrimped/unexpanded
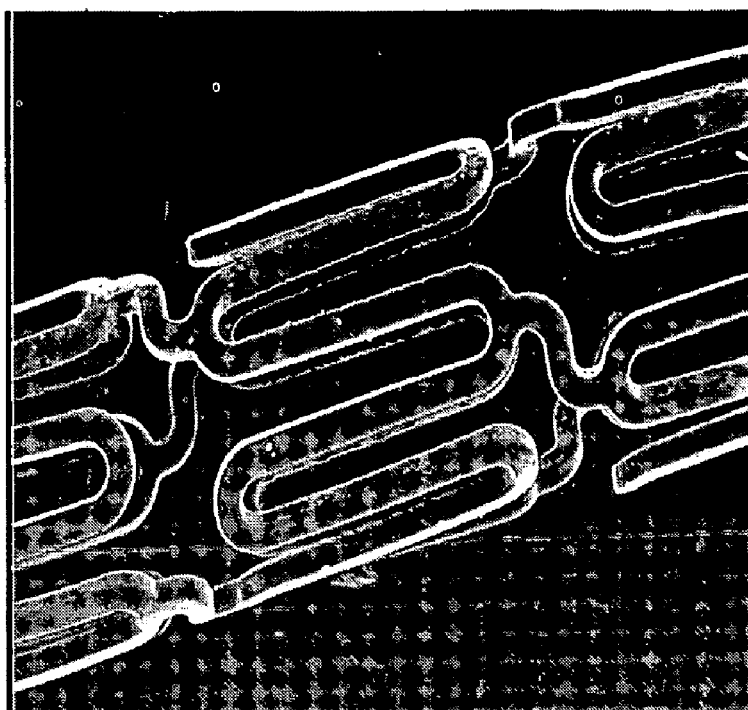
Fig. 45a
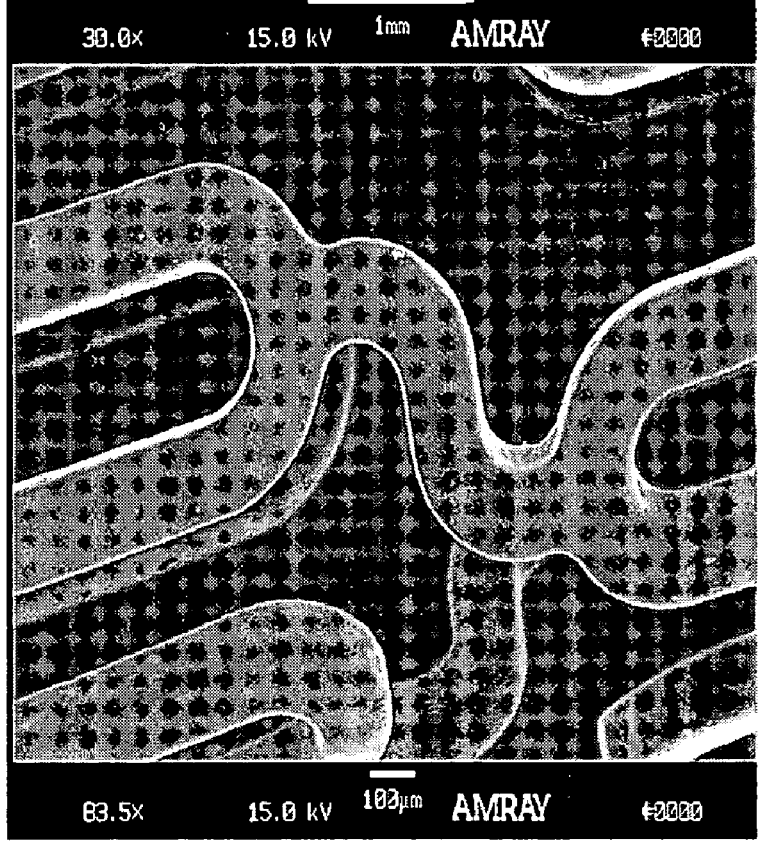
Fig. 45b
Figure 45

Uncrimped/unexpanded
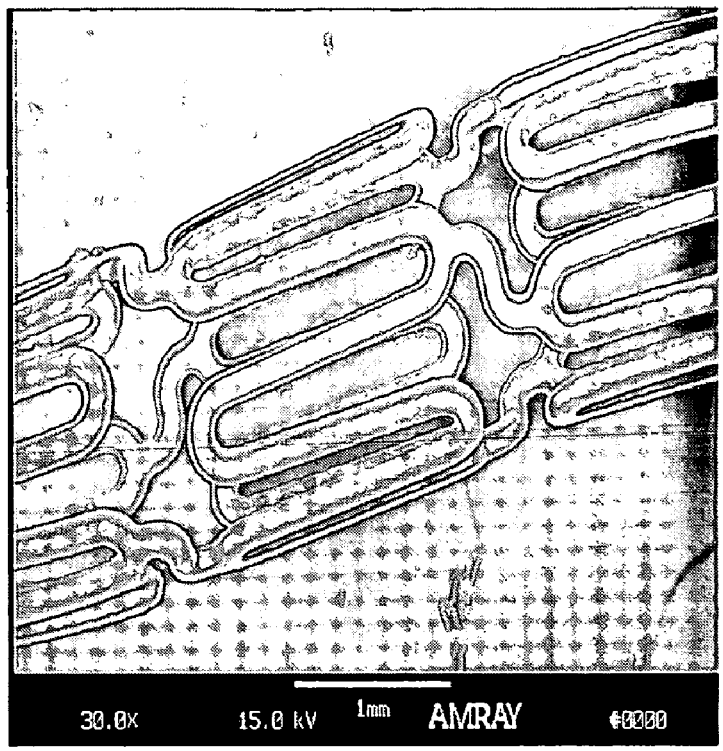
Fig. 46a
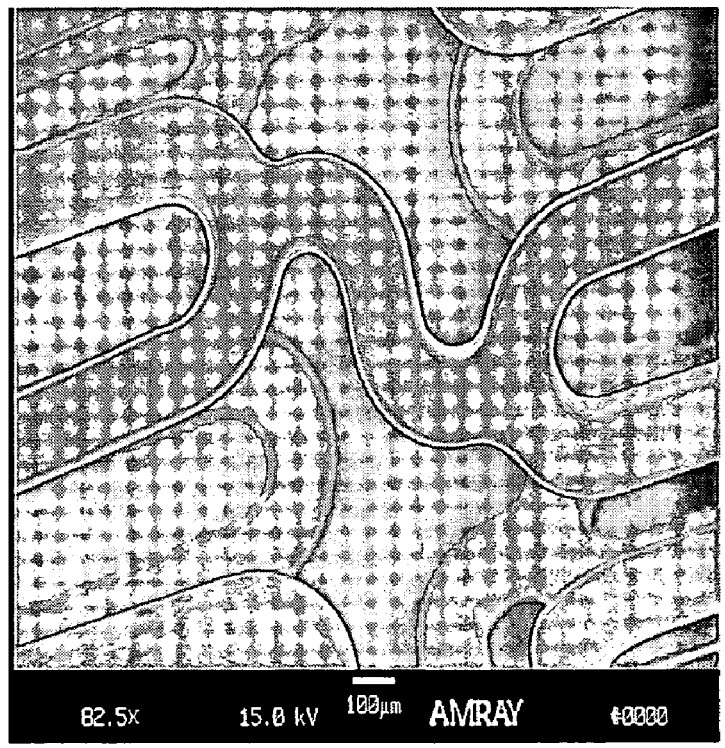
Fig. 46b
Figure 46

MEDICAL DEVICES EMPLOYING NOVEL POLYMERS

This application claims priority to U.S. Provisional Application Ser. No. 60/427,476, filed Nov. 18, 2002. This application is a continuation-in-part of U.S. patent application Ser. No. 10/273,244, filed Oct. 17, 2002, now abandoned which is a continuation of U.S. patent application Ser. No. 09/627,215, filed Jul. 27, 2000, now U.S. Pat. No. 6,486,214, which is a continuation-in-part of U.S. patent application Ser. No. 09/422,294, filed Oct. 21, 1999, now U.S. Pat. No. 6,468,519, which is a continuation-in-part of International Patent Application PCT/US98/18816 WO 99/12990, filed Sep. 10, 1998, which claims priority to U.S. Provisional Application Ser. No. 60/058,328, filed Sep. 10, 1997. This application is a continuation-in-part of U.S. patent application Ser. No. 09/917,194, filed Jul. 27, 2001, now U.S. Pat. No. 6,689,350 which claims priority to U.S. Provisional Patent Application Ser. Nos. 60/261,337, filed Jan. 12, 2001, and 60/220,707, filed Jul. 27, 2000.

This application claims priority to all such previous applications, and such applications are hereby incorporated herein by reference to the extent permitted by law.

BACKGROUND OF THE INVENTION

Targeted delivery of therapeutics is highly desirable in many medical and veterinary applications. The ability to safely and effectively deliver a therapeutic to a specific location would enable administration of the therapeutic or therapeutics directly to the site of treatment while minimizing any possible side effects associated with systemic delivery of the drug.

Site-specific delivery of a therapeutic or therapeutics is desirable for the treatment of many different conditions, including, for example, the treatment of cancers; cardiovascular diseases; vascular conditions; orthopedic disorders; dental disorders; wounds; autoimmune diseases, such as, e.g., rheumatoid arthritis; gastrointestinal disorders; and even for the targeted delivery of proteins and nucleic acid sequences. Furthermore, medical and veterinary devices, including stents, such as, e.g., coronary vascular stents and peripheral vascular stents; vascular grafts; orthopedic implants, such as, for example, hip and knee implants; devices used in surgical applications and wound healing, such as, e.g., sutures, surgical meshes, bandages, and other mechanical wound closure products; and other types of medical and veterinary devices implanted in the body of humans and animals, frequently induce or are associated with inflammation, swelling, infection, hyperproliferation of adjacent tissues, formation of a capsule or granuloma or fibroma surrounding the implant (also known as the foreign body response), and/or pain in the recipient. Devices and methods that reduce these and other pathological responses are desirable to increase the effectiveness and safety of the implanted medical or veterinary device.

One form of drug delivery involves the use of polymers. The use of polymers for drug delivery began in the 1960s with controlled-release oral formulations that involved coating drug tablets, particles or molecules with non-therapeutic biodegradable polymer materials that break down to release the encoated drug. Since that time, polymers containing therapeutics that are admixed or pendant to the polymer backbone have been developed. In the admixture approach, therapeutics are mixed with the polymers before the polymers harden or gel. In the pendant approach, therapeutics are attached to the polymer backbones, by using linkages such as, e.g., enzymatic, chemical, covalent or electrostatic linkages. Unfortunately, such types of biodegradable polymer drug delivery systems are undesirable due to characteristics such as induction of inflammation and/or host response at the site of delivery, low and/or unpredictable potency, unpredictable breakdown products, non-zero-order release rates and burst effects, that is, initial spikes of drug delivery.

In the case of medical and veterinary devices, it is desirable to coat the devices with biocompatible polymer coatings or other surface technologies to reduce inflammation, swelling, infection, hyperproliferation of adjacent tissues, foreign body response and/or pain. Such coatings and surface technologies to date have typically been non-biodegradable, due to the highly inflammatory and unpredicatable nature of the biodegradable polymer coatings described above. Devices coated with a non-biodegradable coating are disadvantageous because the polymers can fatigue over time and delaminate, which could have catastrophic results in certain situations, such as, e.g. in the case of a coated stent that suffers a delamination event as the stent cycles through many heartbeats in a coronary artery. Therefore, it is clear that devices coated with a coating that degrades leaving a bare device, such as, for example, a biodegradable polymer-coated stent, wherein the coating erodes and leaves a bare metal stent, is desirable. Other detrimental side effects associated with biocompatible polymer coatings and surface technologies include, for example, inflexibility, complexity, loading capacity and duration of delivery.

As such, it is clear that there remains a need in the art for medical devices, pharmaceutical compositions and methods of treatment comprising biodegradable polymers that avoid the disadvantages discussed above.

SUMMARY OF THE INVENTION

The present invention relates to medical devices, pharmaceutical compositions and methods of treatment comprising a polymer or polymers that are capable of breaking down (e.g., including, but not limited to, hydrolyzing) in the physiologic milieu to form an active agent or active agents under physiological conditions.

The present invention relates to medical devices comprising a polymer or polymers that are capable of breaking down (e.g., including, but not limited to, hydrolyzing) in the physiologic milieu to form an active agent or active agents under physiological conditions. In one embodiment, the present invention is related to medical devices comprising at least one polymer on all or a part of the surface of the device. In one embodiment, polymer comprises at least one active agent, wherein the active agent or agents are incorporated into the polymer backbone. In one embodiment, the polymer comprises at least one active agent incorporated into the polymer backbone, and further comprises at least one active agent that is not incorporated into the polymer backbone. The active agents can be the same or different.

In one embodiment, the medical device entirely comprises a polymer or polymers that are capable of breaking down (e.g., including, but not limited to, hydrolyzing) to form an active agent or active agents under physiological conditions.

The present invention also relates to pharmaceutical compositions and methods of treatment comprising a polymer or polymers that are capable of breaking down (e.g., including, but not limited to, hydrolyzing) in the to form an active agent or active agents under physiological conditions.

A more complete appreciation of the invention and other intended advantages can be readily obtained by reference to the following detailed description of embodiments of the invention and claims, which disclose the invention and the best modes which are presently contemplated for carrying them out.

BRIEF DESCRIPTION OF THE DRAWINGS

Other advantages of the present invention will be readily appreciated as the same becomes better understood by reference to the following detailed description when considered in connection with the accompanying drawing wherein:

FIG. 1 is an illustration showing Southern Research's continuous microencapsulation process whereby a drug, polymer and polymer solvent dispersion is added to an mechanically agitated water/surfactant mixture to form an emulsion of microdroplets which is then extracted with water to remove solvent and form hardened microcapsules or microspheres for collection by centrifugation, filtration or the like.

FIG. 5 is a chart showing hardness of coatings of polymerized salicylic acid on stainless steel, as measured in the ASTM test for pencil hardness.

FIG. 6 is a chart showing flexibility of coatings of polymerized salicylic acid on stainless steel, as measured in the ASTM test using a conical mandrel.

FIG. 7 is a chart showing adhesion between coatings of polymerized salicylic acid and stainless steel, as measured in the ASTM test for adhesion.

FIG. 10 is a chart showing the glass transition temperature, tensile modulus, yield strength, and elongation at failure of polymerized salicylic acid.

FIG. 12 is a chart showing changes in molecular weight, hardness, flexibility, and adhesion for coatings of polymerized salicylic acid on stainless steel treated with E beam or gamma irradiation relative to similar untreated coatings.

FIG. 21 is a chart showing the thermoanalysis of poly-salicylic anhydride polymer (PolyAspirin I) and of poly-diflunisal anhydride polymer (PolyAspirin II), including $T_g$, ultimate stress, ultimate elongation and toughness.

FIG. 22 is a chart showing hardness, flexibility and adhesion properties of poly-salicylic anhydride polymer (PolyAspirin I) and of poly-diflunisal anhydride polymer (PolyAspirin II).

FIG. 23 is a chart showing hardness, flexibility and adhesion properties of poly-diflunisal anhydride polymer (PolyAspirin II) and poly-diflunisal anhydride polymer admixed with paclitaxel.

FIG. 26 is a chart showing hardness, flexibility and adhesion properties of poly-salicylic anhydride polymer (PolyAspirin I) and of poly-diflunisal anhydride polymer (PolyAspirin II) with γ irradiation.

FIG. 27 is a chart showing hardness, flexibility and adhesion properties of poly-salicylic anhydride polymer (PolyAspirin I) and of poly-diflunisal anhydride polymer (PolyAspirin II) after E beam sterilization.

FIG. 33 shows a light microscopy photo of a 2P 316 RCA poorly deployed stent with severe malapposition; medical necrosis with moderate to severe fibrin deposition with hemorrhage can be seen.

FIG. 34 shows a light microscopy photo of a 2P 339 LAD stent exhibiting malapposition with minimal neointimal growth; the midsection is deployed over a branch vessel and there is necrosis with extensive fibrin and hemorrhage and giant cell reactions around the stent struts.

FIG. 35 shows a light microscopy photo of a 2P 339 LCx stent that is well expanded; concentric neointimal growth of smooth muscle and proteoglycans can be seen. Stent struts show moderate to sever fibrin deposition while inflammation is minimal.

FIG. 44 (a-b) is a scanning electon (SEM) micrograph of a polymer (PX184-55-80) coated stent according to the present invention.

FIG. 45 (a-b) is a scanning electon (SEM) micrograph of a polymer (PX990-63-57) coated stent according to the present invention.

FIG. 46 (a-b) is a scanning electon (SEM) micrograph of a polymer (PX727-63-25) coated stent according to the present invention.

DETAILED DESCRIPTION OF THE INVENTION

Figure 2:
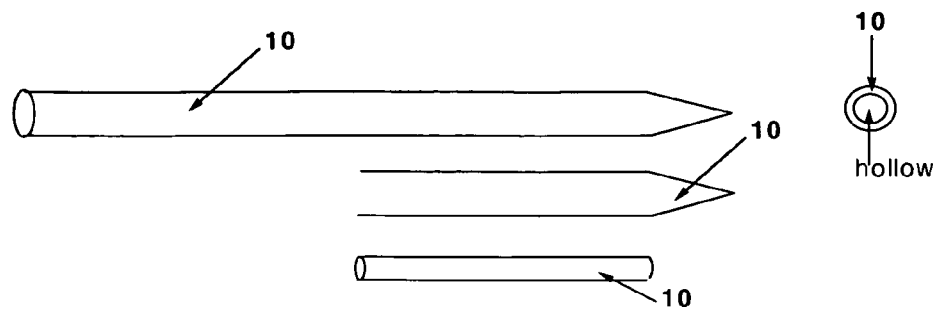
FIG. 2 is an illustration of several hollow needle-type carriers 12 for use in the invention.

The present invention relates to medical devices, pharmaceutical compositions and methods of treatment comprising a polymer or polymers that are capable of breaking down (e.g., including, but not limited to, hydrolyzing) in the to form an active agent or active agents under physiological conditions.

The present invention relates to medical devices comprising a polymer or polymers that are capable of breaking down (e.g., including, but not limited to, hydrolyzing) in the to form an active agent or active agents under physiological conditions. In one embodiment, the medical device comprises a polymer comprising at least one active agent, wherein the active agent or agents are incorporated into the polymer backbone. In one embodiment, the polymer comprises at least one active agent incorporated into the polymer backbone, and further comprises at least one active agent that is not incorporated into the polymer backbone. The active agents can be the same or different.

In one embodiment, the present invention is related to medical devices comprising at least one polymer on all or a part of the surface of the device. Such medical devices can be used, for example, to deliver an active agent to the site of the device, such as, e.g., an active agent or agents that would reduce or eliminate an adverse physiological condition associated with the use of the device. In one embodiment, the medical device entirely comprises a polymer or polymers that are capable of breaking down (e.g., including, but not limited to, hydrolyzing) in the to form an active agent or active agents under physiological conditions.

The present invention also relates to pharmaceutical compositions and methods of treatment comprising a polymer or polymers that are capable of breaking down (e.g., including, but not limited to, hydrolyzing) in the to form an active agent or active agents under physiological conditions. In one embodiment, polymer comprises at least one active agent, wherein the active agent or agents are incorporated into the polymer backbone. In one embodiment, the polymer comprises at least one active agent incorporated into the polymer backbone, and further comprises at least one active agent that is not incorporated into the polymer backbone. The active agents can be the same or different.

The present invention provides a medical device having at least one surface, comprising a first polymer on all or a portion of the surface, wherein the polymer is capable of breaking down (e.g., including, but not limited to, hydrolyzing) in the to form a first active agent under physiological conditions. Devices comprising a polymer that is capable of breaking down (e.g., including, but not limited to, hydrolyzing) in the to form more than one active agent under physiologic conditions are also provided.

The present invention further provides a medical device having at least one surface comprising a first polymer on all or a portion of the surface, wherein the polymer comprises at least one active agent, wherein the active agent or agents are incorporated into the polymer backbone.

The present invention also provides a medical device having at least one surface, comprising a first polymer and a second polymer on all or a portion of the surface. The first polymer is capable of breaking down (e.g., including, but not limited to, hydrolyzing) in the physiologic milieu to form a first active agent, and the second polymer is capable of breaking down (e.g., including, but not limited to, hydrolyzing) in the physiologic milieu to form a second active agent.

The present invention further provides a medical device having at least one surface, comprising a first polymer and a second polymer on all or a portion of the surface. The first polymer is capable of breaking down (e.g., including, but not limited to, hydrolyzing) in the physiologic milieu to form a first active agent, and the second polymer is capable of breaking down (e.g., including, but not limited to, hydrolyzing) in the physiologic milieu to form a second active agent, wherein the first and second active agents can combine in vivo to form a third active agent.

The present invention also provides a stent having at least one surface, comprising a first polymer on all or a portion of the surface, wherein the polymer is capable of breaking down (e.g., including, but not limited to, hydrolyzing) in the to form a first active agent under physiological conditions. In one embodiment, the stent comprises a polymer that comprises at least one active agent, wherein the active agent or agents are incorporated into the polymer backbone.

A method for delivering an active agent to an interior surface of a vein or an artery is also provided.

The polymers, medical devices, pharmaceutical compositions and methods of treatment provided herein can be designed to reflect advantages such as, e.g., the ability to deliver a high potency or concentration of drug by weight if desired; a near "zero-order" drug release over short or long periods if desired; ease of fabrication into coatings, fibers, microspheres, pellets, etc.; little or no evidence of a "burst effect" or initial spike of drug; predictable breakdown products; multiple routes of administration; and localized delivery for improved efficacy and reduced side-effects. Furthermore, the polymers, medical devices, pharmaceutical compositions and methods of treatment provided herein can be designed such that they do not induce an inflammatory response when administered to or implanted within a host.

An advantage of the present invention is that it can be used for controlling the onset and progression of adverse physiological conditions at the site of a medical device or method of treatment. A directed application of pharmaceutical treatment circumvents the need for a general (i.e., "whole-body" or oral) administration of the necessary therapeutics. Accordingly, such directed application of therapeutics provides faster, more targeted relief of the adverse conditions while minimizing side effects of the administration of the therapeutics.

While the present invention may be embodied in many different forms, several specific embodiments are discussed herein with the understanding that the present disclosure is to be considered only as an exemplification of the principles of the invention, and it is not intended to limit the invention to the embodiments illustrated.

DEFINITIONS

The following definitions are used, unless otherwise described:

The article "a" and "an" as used herein refers to one or to more than one (i.e. at least one) of the grammatical object of the article. By way of example, "an element" means one element or more than one element.

As used herein, "active agent" refers to a substance that has a physiological effect when present in a living system. A "physiological effect" can be, for example, any effect on the functioning of an organism, such as, e.g., alteration of normal function, alteration of abnormal function, and/or restoration to normal function. A physiological effect may include, but is not limited to, binding to a biomolecule (i.e., DNA, protein, carbohydrate, lipid, etc.), inhibition of enzyme activity, and sequestration of small molecule cofactors (i.e., metal ions, amino acids, etc.). An active agent can be a drug or therapeutic, for example, a compound or precursor of a compound used to treat a specific disease or medical condition As used herein, "administering an active agent near the site," means applying the agent proximal to the site, so that the agent can produce the desired or stated therapeutic effect (e.g., reduce bone resorption at the site).

Alkyl, alkoxy, etc. denote both straight and branched groups; but reference to an individual radical such as "propyl" embraces only the straight chain radical, a branched chain isomer such as "isopropyl" being specifically referred to.

The term "amino acid," comprises the residues of the natural amino acids (e.g. Ala, Arg, Asn, Asp, Cys, Glu, Gln, Gly, His, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1$-$C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & Sons, Inc., and references cited therein).

As used herein, an agent is "appended" to a polymer when the agent is bonded to the polymer as a side chain or side group, but is not part of the polymer backbone. Preferably, the agent is bonded to the polymer through a linkage that is suitable to release the agent when the polymer is administered according to the methods of the invention. For example, the agent can conveniently be linked to a polymer through a hydrolyzable linkage such as an anhydride or ester linkage.

Aryl denotes a phenyl radical or an ortho-fused bicyclic carbocyclic radical having about nine to ten ring atoms in which at least one ring is aromatic.

As used herein, an agent or functional group is "associated" with the polymer by direct, linear (i.e., chemically bonded) integration into the polymer backbone, chemical bonding to the polymer backbone as a side chain or side group, but not as part of the polymer backbone structure, electrostatic bonding to the polymer backbone, linkage to the polymer backbone by a linking group, pendent (i.e., an offshoot of the polymer backbone, neither oligomeric nor polymeric) attachment to the polymer backbone, or bonding to one or both ends of the polymer chain. The association used will depend on the functional characteristics (e.g., number and type of reactive groups) of the functional group.

A substance is said to be "biocompatible" when it has the properties of being compatible with a living system, is not toxic to the living system, and does not cause an immunological reaction in the living system.

A substance is said to be "biodegradable" when it is capable of being broken down into components smaller than its original size and structure when it is present in a living system.

As used herein, the term "dispersed through the polymer matrix" means that an therapeutic agent is located within the matrix of a polymer such that it can be released in a controlled fashion within the body. Preferably, the polymer matrix comprises a biodegradable polymer.

As used herein, the term "dissociate" indicates that a substance is broken into smaller parts. The smaller, dissociated parts of the original undissociated whole may be chemically identical to the undissociated whole or they may be chemically dissimilar to the undissociated whole. Chemical dissimilar dissociation products may be heterogeneous or homogeneous with respect to either or both of chemical properties and size. Dissociation products may also have the property of being able to recombine and create the original undissociated whole, or they may be permanently dissociated. Dissociation may occur spontaneously, as an inherent property of the undissociated whole, or dissociation may occur as a result of a physical or chemical process, such as hydrolysis of the undissociated whole.

The term ester linkage means —OC(=O)— or —C(=O)O—; the term thioester linkage means —SC(=O)— or —C(=O)S—; and the term amide linkage means —N(R)C(=O)— or —C(=O)N(R)—, wherein each R is a suitable organic radical, such as, for example, hydrogen, $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$alkyl, or heteroaryl$(C_1-C_6)$alkyl. The term urethane or carbamate linkage means —OC(=O)N(R)— or —N(R)C(=O)O—, wherein each R is a suitable organic radical, such as, for example, hydrogen, $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$alkyl, or heteroaryl$(C_1-C_6)$alkyl, and the term carbonate linkage means —OC(=O)O—.

The term "formed into" includes within its meaning that a polymer, compound and/or composition of the invention can be physically configured into various shapes, geometries, structures and configurations including, but not limited to, a film, fiber, rod, coil, corkscrew, hook, cone, pellet, tablet, tube (smooth or fluted), disc, membrane, microparticle, nanoparticle, "biobullet" (i.e., bullet shaped), seed (i.e., bullet shaped or targeted seeds), etc.

A "functional group" as used in the present invention is a chemical moiety that can be incorporated into a polymer, e.g., into an ester, thioester, urethane, carbamate, carbonate or amide linkage of a polymer (as discussed in detail below), such that, upon hydrolysis of the polymer or by enzymatic action (for example, by action of one or more esterases) on the polymer, the therapeutic agent is obtained. These groups can independently be a hydroxy group (—OH), a mercapto group (—SW), an amine group (—NHR), or a carboxylic acid (—COOH).

Halo is fluoro, chloro, bromo, or iodo.

As used herein, the term "healing" means the repair of a defect or non-normal condition or state. Healing can be the restoration to normal health or the process of a return to health.

Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_6)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

As used herein, the term "hard tissue" includes tissue that has become mineralized, such as, for example, bone, cartilage, or both.

The term "host" includes animals and plants, such as, e.g., a mammal, including a human. A host can also be a "patient."

For purposes of the present invention, by "low molecular weight drug" it is meant to include any compound with one carboxylic acid group and at least one amine, thiol, alcohol or phenol group within its structure, wherein the compound has a demonstrated pharmacological activity and a molecular weight of approximately 1000 daltons or less.

A "medical device" is a therapeutic device, such as, e.g., a "medical implant," that is used specifically for a medically related purpose. For example, a bone screw is both a medical device and a medical implant.

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

As used herein, "physiological conditions" are the conditions in a physiological system or environment, such as, e.g., within a mammal, such as a human. The physiological conditions can be "normal physiological conditions" such as conditions found in a normal, healthy patient, or "abnormal physiological conditions" such as conditions found in an unhealthy, sick, or injured patient. Physiological conditions can be found, for example, inside a mammal, or on the surface of a mammal, such as, e.g., on the mammal's skin or hair.

As used in the present invention, a "sleeve" is a physical conformation of a substance in which the substance sits adjacent to and fits around the outside of a separate substance, such as, e.g., a medical or therapeutic device. For example, a plastic coating surrounding a metal rod can be considered to be a sleeve around that metal rod. For the purpose of the present invention, a sleeve may also sit adjacent to a separate substance without completely enclosing the outer surface of the separate substance. In the present invention, a sleeve may be used to describe a substance that is formed into, for example, a coating, a film, a sheath, a wrap, a tube, a cuff, or a formed gel partially or wholly surrounding separate substance, such as, for example, a medical device.

As used herein, a substance is said to be solid when it has three dimensions and has the properties of a solid, i.e., it is not a liquid or gas. For example, a piece of paper, a metal rod, and steel needle are all considered to be solids as the term is used in the present invention. As used herein, a substance is a "semi-solid" when it has properties of a solid, but also has some of the properties of a liquid, i.e., it is easily deformable by physical or chemical action. For example, gel and clay are semi-solids according to the use of the term in the present invention.

A "therapeutic agent" is an "active agent" which aids in the prevention or treatment of an undesired occurrence or condition in a living system A "therapeutic device" is defined herein as any device that aids in the prevention or treatment of an undesired occurrence or condition in a living system. A therapeutic device that is either temporarily or permanently placed either partially or wholly inside a living system may also be referred to as a "therapeutic implant." As used herein, a functional therapeutic device may be made of more than one therapeutic device.

As used herein, administering an agent "to or near the tissue" means administering the agent so that it is in direct contact with the tissue or administering the agent to a location proximal to tissue, so that the agent can produce the desired or stated therapeutic effect.

A "veterinary device" is a therapeutic device that is used specifically for a medically related purpose in an animal.

Polymers

A polymer of the invention can be any polymer suitable for delivering an active agent to the patient, such as, for example, a biocompatible and biodegradable polymer that is capable of releasing at least one active agent upon degradation and/or hydrolysis of the polymer under physiological conditions.

Suitable polymers include, for example, polymers that have a polymeric backbone linking an active agent or agents into polymeric drug delivery systems. Such polymers uniquely incorporate the active agent or agents as a repeating structural component of the polymer backbone, which is developed using hydrolysable bonds such as esters, thioesters, amides, urethanes, carbamates and carbonates as opposed to radical or aliphatic bonds. Once placed in the body of a host, such as, e.g., a mammal, such as, e.g., a human, the polymer breaks down over time and the active agent is released. In one embodiment, a suitable polymer degrades over a controlled period of time to produce relatively high, localized levels of the active agent or agents, allowing for enhanced therapeutic effects while minimizing side effects compared to the systemic delivery of drugs.

In one embodiment, a suitable polymer is biocompatible, biodegradable, and demonstrates favorable solubility and processability, as well as degradation properties suitable for the desired use. In one embodiment of the invention, the active agent is released over time as the polymer hydrolyzes under physiological conditions, providing for an extended-release formulation that provides a consistent source of the therapeutic substance for an extended period of time.

Suitable polymers for use in the present invention include, for example, polyesters, such as, e.g., poly(ester-esters) and poly(ester-carbonates); polyamides; and polyanhydrides, such as poly(anhydride-esters) and poly(azo-anhydrides), and are described in, e.g., e.g., U.S. Pat. Nos. 6,328,988; 6,365,146; 6,468,519; 6,486,214; 6,497,895; 6,602,915; 6,613,807; 4,916,204; and 4,868,265; U.S. Published Patent Applns. 2002/0071822 A1; 2002/0106345 A1; 2003/0035787 A1; 2003/0059469 A1; 2003/0104614 A1; 2003/0170202 A1; U.S. patent application Ser. Nos. 09/508,217; 10/368,288; 10/622,072; 10/646,336; 10/647,701; and International Patent Applns. WO 99/12990; WO 01/28492; WO 01/41753; WO 01/58502; WO 02/09767; WO 02/09768; WO 02/09769; WO 03/005959; WO 03/046034; WO 03/065928; and WO 03/072020; and Erdmann, L., Uhrich, K. E., *Biomaterials*, 21: 1941-1946 (2000), incorporated herein by reference. The polymer of the invention can be a polyanhydride. Preferably, the polyanhydride backbone has one or more groups that will provide an active compound upon hydrolysis or enzymatic degradation of the polymer.

In one embodiment, the polymer comprises one or more units of Formula (I) in the backbone:

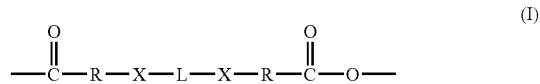

wherein each R is a group that will provide a therapeutically active compound upon hydrolysis of the polymer; each X is independently an amide linkage, a thioester linkage, or an ester linkage; and L is a linking group. The polymer can comprise one or more species of L.

The polyanhydrides of Formula I serve as the polymer backbone of polymeric drug delivery systems comprising these low molecular weight drugs. Such polymeric drug delivery systems provide an effective means to deliver drugs in a controlled fashion to any site of a host, such as an animal or a plant.

In one embodiment, the polyanhydride of Formula I links molecules of a low molecular weight drug or drugs containing within their structure one carboxylic acid group and at least one amine, thiol, alcohol or phenol group.

In one embodiment of the invention, the polymer is an aromatic polyanhydride having a repeating unit with the structure of Formula I in which each R and X is independently selected to provide aromatic polyanhydrides that hydrolyze to form a salicylic acid or salicylic acid derivative. Examples of appropriate salicylates include, but are not limited to, diflunisal, diflucan, thymotic acid, 4,4-sulfinyidinailine, 4-sulfanilamidosalicylic acid, sulfanilic acid, sulfanilylbenzylamine, sulfaloxic acid, succisulfone, salicylsulfuric acid, salsallate, salicylic alcohol, salicylic acid, orthocaine, mesalamine, gentisic acid, enfenamic acid, cresotic acid, aminosalicylic acid, aminophenylacetic acid, acetylsalicylic acid, and the like. The identification of R and X moieties that provide aromatic polyanhydrides that hydrolyze to form such therapeutically useful salicylates can be readily determined by those of ordinary skill in the art without undue experimentation.

In one embodiment, the active agent is salicylic acid.

In one embodiment, the polymer comprises a repeating unit with the structure of Formula (II):

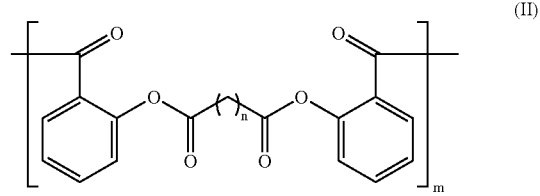

n can be any suitable number of carbon atoms, such as, for example, an even number of carbon atoms. In one embodiment, the active agent is salicylic acid, and L is a dicarboxylic acid hydrocarbon chain with an even number of carbon atoms. A suitable even number of carbon atoms includes any even number of carbon atoms that will result in a functional polymer, e.g., about 2 to about 20 carbon atoms, about 2 to about 18 carbon atoms, about 4 to about 16 carbon atoms, about 4 to about 14 carbon atoms, about 6 to 16 carbon atoms, about 8 to 12 carbon atoms or about 6 to about 10 carbon atoms.

Further, the nature of the linking group L in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

The linking group may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol, polyvinyl alcohol or polyvinyl pyrrolidone.

The linking group may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The linking group may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

The linking group may be a segment that undergoes thermoreversible gellation, such as Pluronic F127 and poly(N-isopropyl acrylamide). It may incorporate structurally-reinforcing segments, such as polyetherurethane, polyesterurethane, etc.

The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a peptide or an amino acid. The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms; or a divalent, branched or unbranched, hydrocarbon chain, having from 3 to 15 carbon atoms; or a divalent, branched or unbranched, hydrocarbon chain, having from 6 to 10 carbon atoms; or a divalent hydrocarbon chain having 7, 8, or 9 carbon atoms; or a divalent hydrocarbon chain having 8 carbon atoms.

m can be any suitable number of repeating units, including, e.g., a number of repeating units that results in a polymer with a molecular weight of about 1,500 daltons to about 1,000,000 daltons; about 1500 daltons to about 85,000 daltons, about 1500 daltons to about 75,000 daltons, about 1500 daltons to about 60,000 daltons, about 1500 daltons to about 50,000 daltons, about 1500 daltons to about 35,000 daltons, about 1500 daltons to about 20,000 daltons, about 1500 daltons to about 15,000 daltons, or about 1500 daltons to about 10,000 daltons, calculated by Gel Permeation Chromatography (GPC) relative to narrow molecular weight polystyrene standards.

Further, the polymers of the invention can have an average molecular weight of about 1500 daltons to about 1,000,000 daltons. The compounds that form the R group contained within the polymer structure can have one carboxylic acid group and at least one amine, thiol, alcohol or phenol group. Thus, when R is the residue of a therapeutic agent (drug), these polymers can function as drug delivery systems, which provide an effective means to deliver drugs in a controlled fashion as a function of polymer degradation to any site of a host.

Polyanhydride materials have been extensively studied; for example, see U.S. Pat. Nos. 4,757,128, 4,997,904, 4,888,176, 4,857,311, and 5,264,540, as well as International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. For example, higher molecular weight polyanhydrides typically have greater mechanical strength and higher stability. Further, higher molecular weight polyanhydrides can be made into harder and thicker coatings. Accordingly, the invention provides a polymer comprising a backbone that has a plurality of anhydride bonds, wherein the polymer has an average molecular weight of at least about 120,000 daltons.

Preferably, the polymers of the invention have an average molecular weight of at least about 130,000 daltons. Another specific polymer has an average molecular weight of at least about 140,000 daltons. Another specific polymer has an average molecular weight of at least about 150,000 daltons. Another specific polymer has an average molecular weight of at least about 175,000 daltons. Another specific polymer has an average molecular weight of at least about 200,000 daltons. Even more preferable is a polymer has an average molecular weight of at least about 300,000 daltons. Another specific polymer has an average molecular weight of at least about 500,000 daltons. Another specific polymer has an average molecular weight of at least about 600,000 daltons. Another specific polymer has an average molecular weight of at least about 750,000 daltons.

Figure 11:
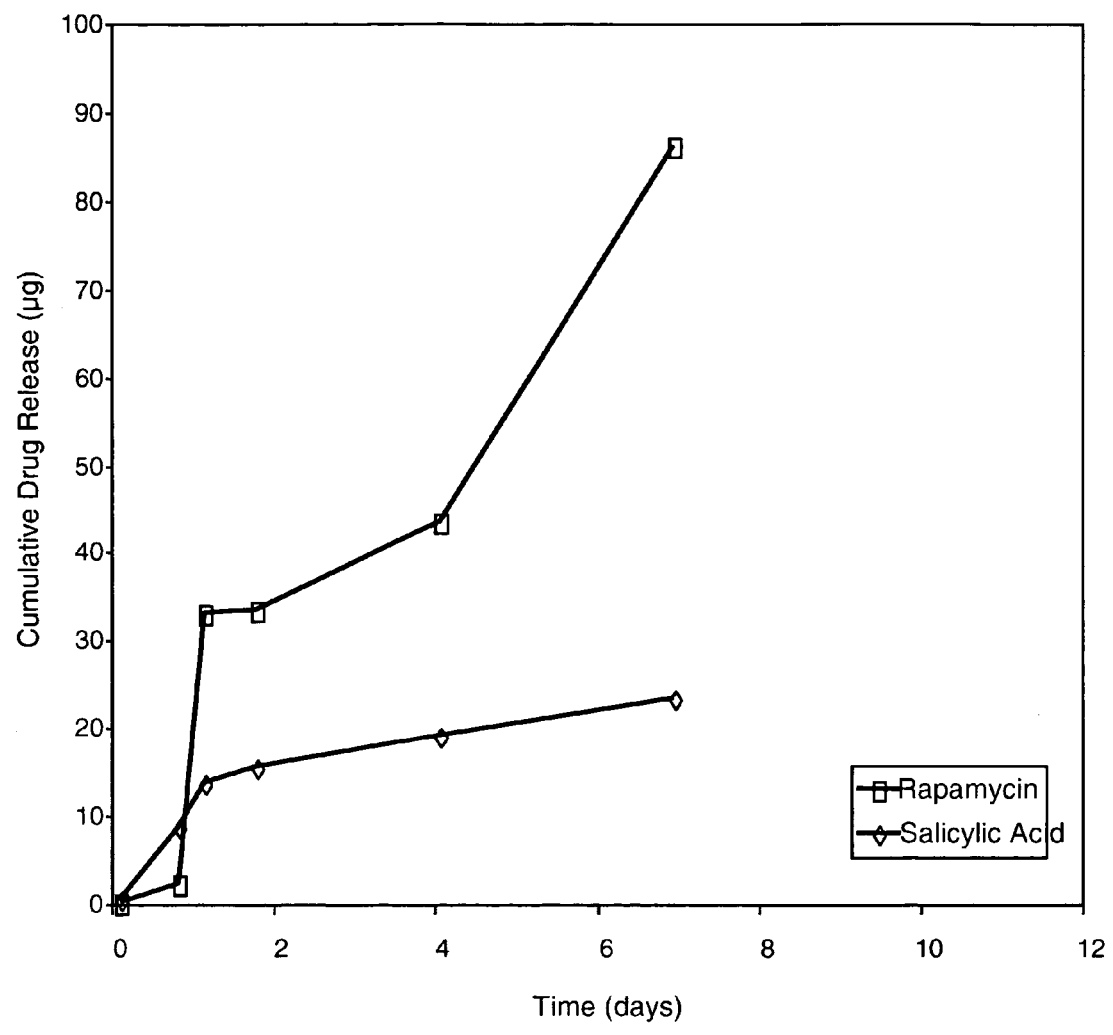
FIG. 11 is a graph showing the cumulative masses in a bathing solution of PBS with 25% ethanol resulting from simultaneous generation of salicylic acid by the bioerosion of a coating of polymerized salicylic acid and release of sirolimus from that coating.
Figure 28:
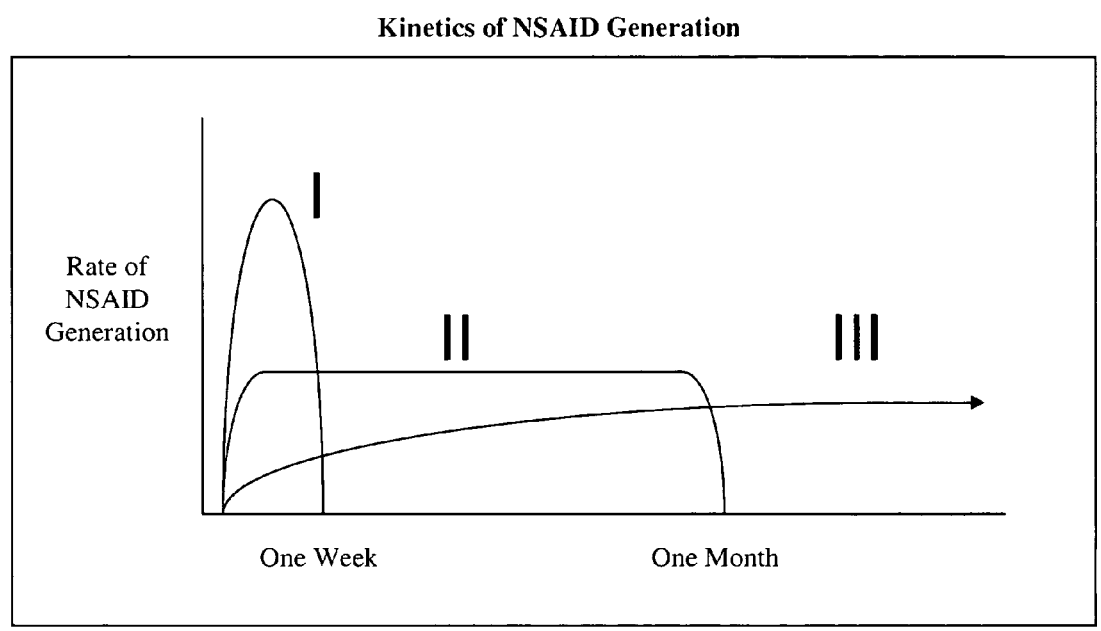
FIG. 28 is a graph illustrating the kinetics of NSAID generation for PolyAspirin I (I), PolyAspirin II (II), and PolyAspirin III (III).
Figure 29:
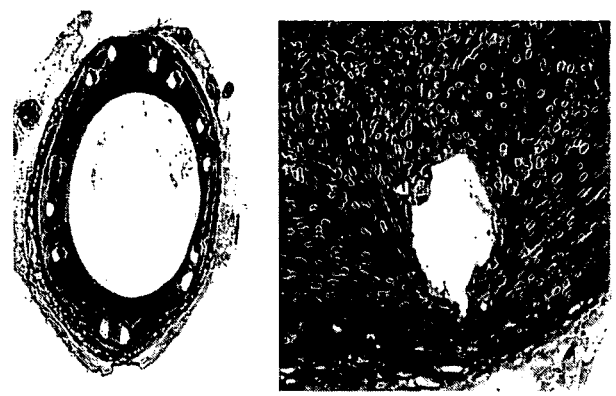
FIG. 29 shows a light microscopy photo of a 2P 315 LAD well deployed stent with concentric neointimal growth consisting of smooth muscle cell growth with proteoglycans.
Figure 30:
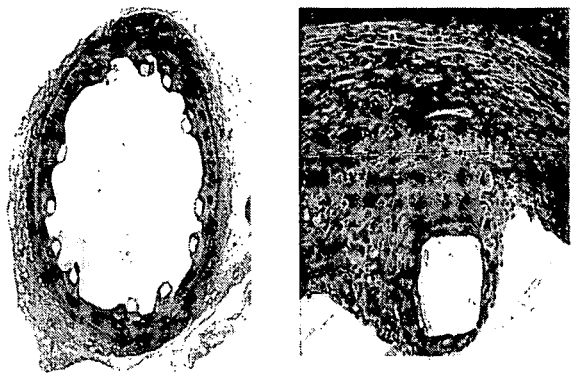
FIG. 30 shows a light microscopy photo of a 2P 315 LCx deployed stent; extensive malapposition of the stent struts with underlying medial necrosis can be seen; the distal sections are worse. There is moderate to severe platlet/fibrin deposition around stent struts with inflammation and hemorrhage.
Figure 31:
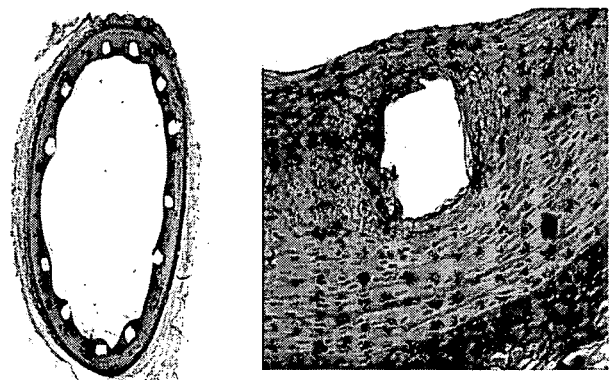
FIG. 31 shows a light microscopy photo of a 2P 315 RCA well deployed stent with concentric neointimal growth consisting of smooth muscle cells, collagen, and proteoglycans.
Figure 32:
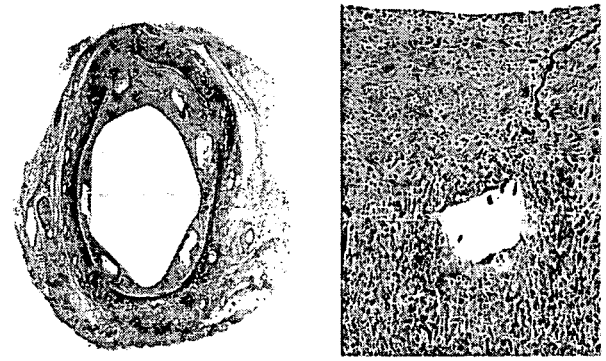
FIG. 32 shows a light microscopy photo of a 2P 316 LAD stent exhibiting concentric noeintimal growth with granulomas around stent struts. Mild to moderate fibrin accumulation can be seen.
Figure 36:
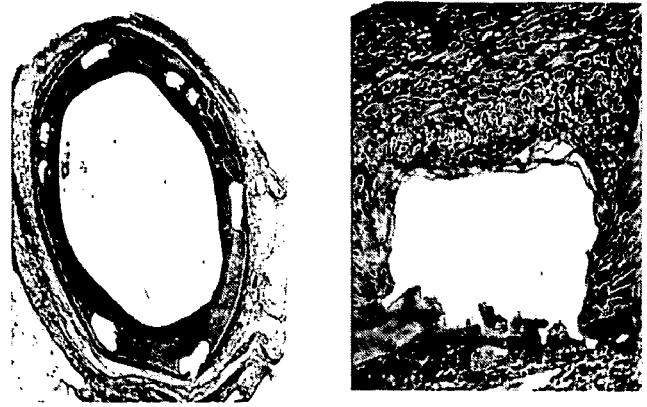
FIG. 36 shows a light microscopy photo of a 2P 339 RCA stent that is well deployed and displays concentric neointimal growth consisting of smooth muscle cells and proteoglycans.
Figure 37:
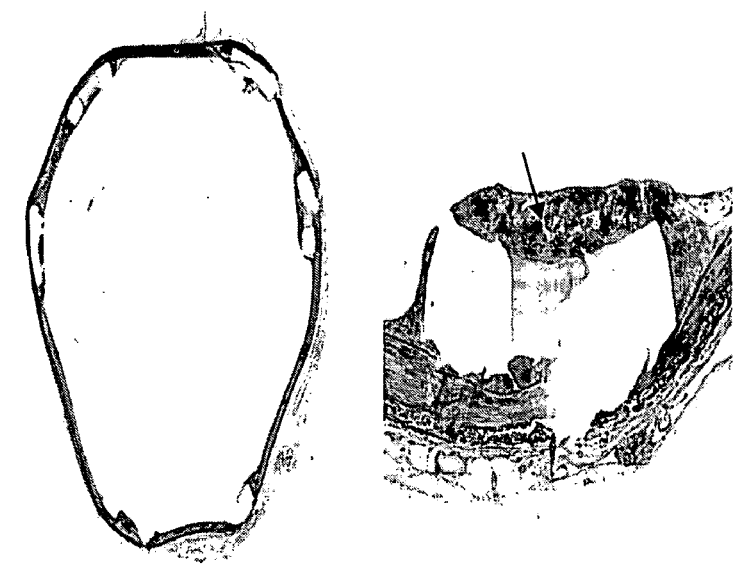
FIG. 37 shows a light microscopy photo of a control bare stent harvested at 7 days; the struts are well expanded and the lumen is widely patent. The high power view on the right shows a neointima of mostly fibrin (arrow) with a few smooth muscle and inflammatory cells.
Figure 38:
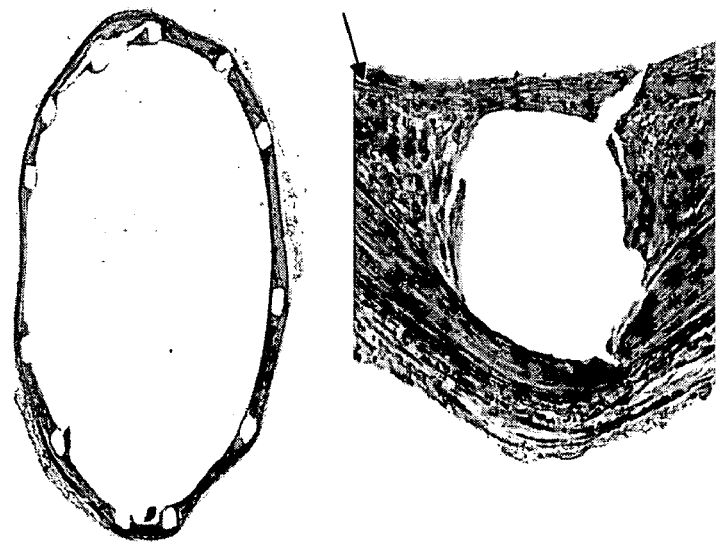
FIG. 38 shows a light microscopy photo of a rabbit iliac artery stent coated with PolyAspirin I (thin coating). The struts are well expanded and the lumen is widely patent. The high power view on the right shows a neointima consisting of fibrin (arrow), some smooth cells, and proteoglycan.
Figure 39:
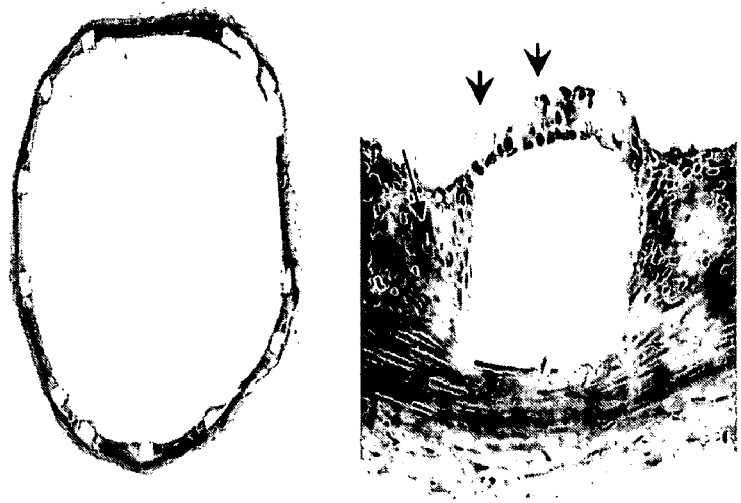
FIG. 39 shows a light microscopy photo of a rabbit iliac artery stent coated with a PolyAspirin I (thick coating). The struts are well expanded and the lumen is widely patent. The high power view shows a neointima consisting of fibrin, smooth muscle cells, proteoglycan and acute and chronic inflammatory cells.
Figure 40:
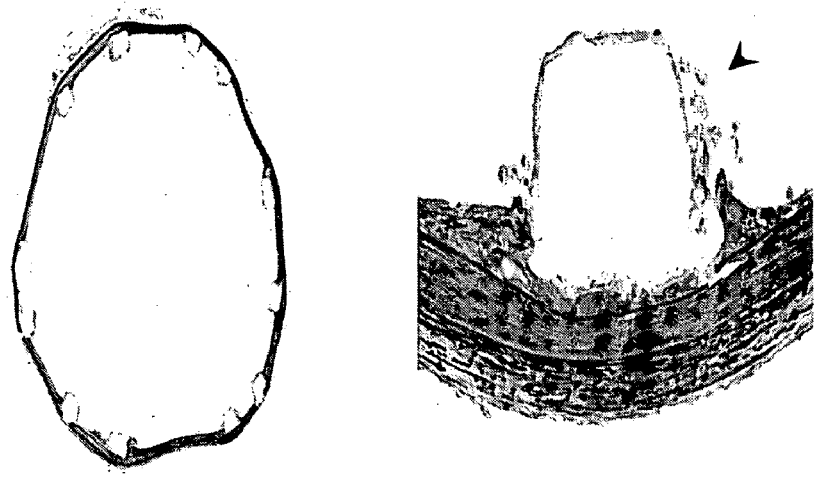
FIG. 40 shows a light microscopy photo of a rabbit iliac artery stent coated with PolyAspirin II. The struts are well expanded and the lumen is widely patent. A thin neointima is barely covering a stent strut and a few inflammatory cells and smooth muscle cells can be seen at the periphery of the strut.
Figure 41:
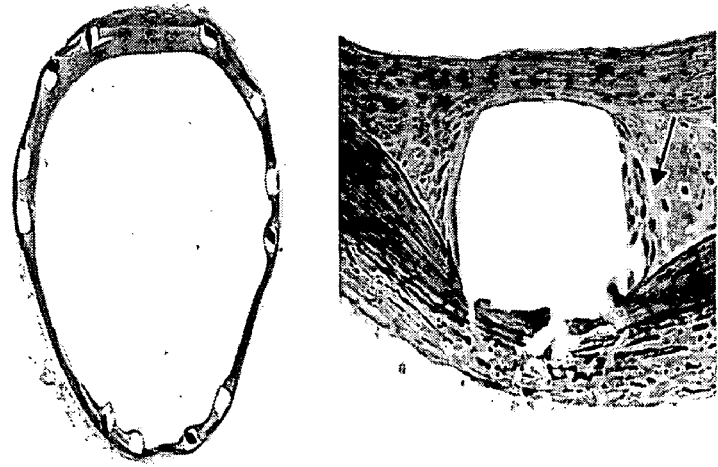
FIG. 41 shows a light microscopy photo of a control bare steel stent deployed in the rabbit iliac artery for 28 days. The struts are well expanded and the lumen is widely patent. The neointimal response is nominal and healing is near complete. The high power view shows a thickened neointima consisting mostly of smooth muscle cells and proteoglycans.
Figure 42:
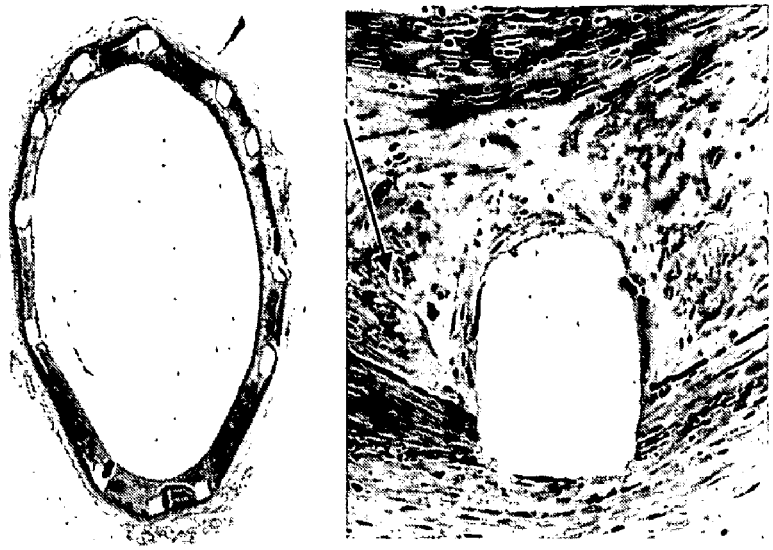
FIG. 42 shows a light microscopy photo of a stainless steel stent loaded with PolyAspirin I deployed in the rabbit iliac artery for 28 days. The struts are well expanded and the lumen is widely patent. The neointimal response is nominal and healing is near complete. The high power view shows a thickened neointima consisting mostly of smooth muscle cells and prteoglycans.
Figure 43:
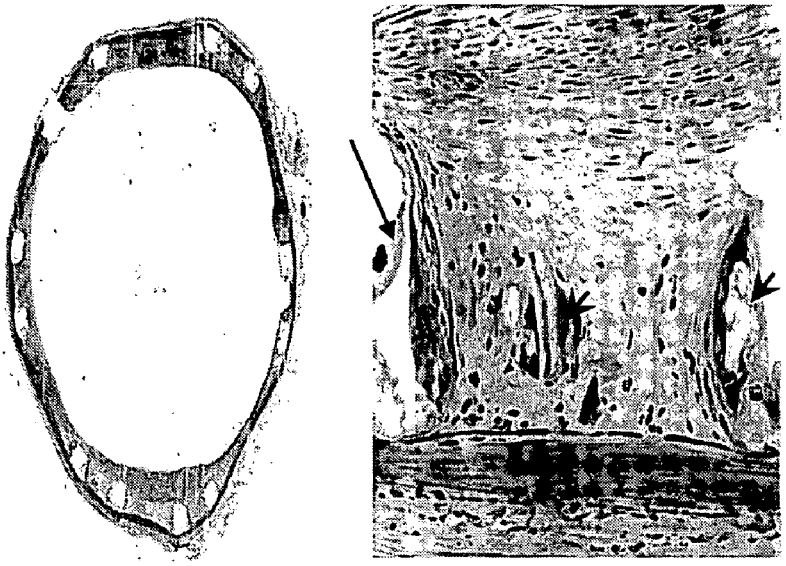
FIG. 43 shows a light microscopy photo of a stainless steel stent coated with PolyAspirin II deployed in the rabbit iliac artery for 28 days. The struts are well expanded and the lumen is widely patent. A collection of giant cells containing fragments of polymer grayish staining with foamy appearance and a polymer fragment is seen around a stent strut. The neointima is well healed consisting mostly of smooth muscle cells and proteoglycans.

In one embodiment, the polymer comprises a repeating unit with the structure of FIG. 11, wherein the polymer breaks down relatively quickly, e.g., over a period of days, into salicylic acid as demonstrated in FIG. 28.

In one embodiment, the active agent is diflunisal.

In one embodiment, the polymer comprises a repeating unit with the structure of Formula (III):

mer (e.g. for branching, for cross linking, for appending other molecules (e.g. another biologically active compound) to the polymer, for changing the solubility of the polymer, or for effecting the biodistribution of the polymer).

The linking group may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol, polyvinyl alcohol or polyvinyl pyrrolidone.

The linking group may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The linking group may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS),

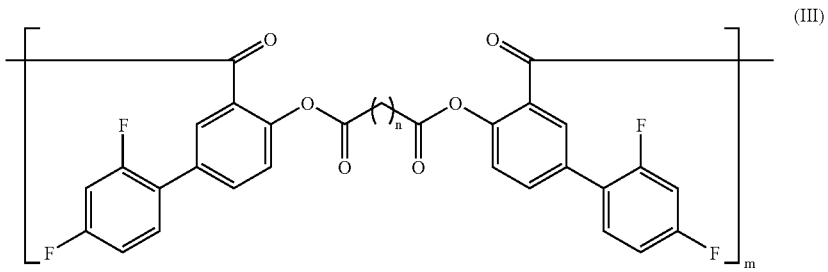

n can be any suitable number of carbon atoms, such as, for example, an even number of carbon atoms. In one embodiment, the active agent is diflunisal, and L is a dicarboxylic acid hydrocarbon chain with an even number of carbon atoms. A suitable even number of carbon atoms includes any even number of carbon atoms that will result in a functional polymer, e.g., about 2 to about 20 carbon atoms, about 2 to about 18 carbon atoms, about 4 to about 16 carbon atoms, about 4 to about 14 carbon atoms, about 6 to 16 carbon atoms, about 8 to 12 carbon atoms, or about 6 to about 10 carbon atoms.

Further, the nature of the linking group L in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the poly-hydroxy groups from poly(vinyl alcohol), polysaccharides and poly(alginates), and amino groups from poly(L-lysine), poly(2,2-dimethylaminoethyl methacrylate) and poly(amino acids).

The linking group may be a segment that undergoes thermoreversible>gellation, such as Pluronic F127 and poly (N-isopropyl acrylamide). It may incorporate structurally-reinforcing segments, such as polyetherurethane, polyesterurethane, etc.

The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a peptide or an amino acid. The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms; or a divalent, branched or unbranched, hydrocarbon chain, having from 3 to 15 carbon atoms; or a divalent, branched or unbranched, hydrocarbon chain, having from 6 to 10 carbon atoms; or a divalent hydrocarbon chain having 7, 8, or 9 carbon atoms; or a divalent hydrocarbon chain having 8 carbon atoms.

m can be any suitable number of repeating units, including, e.g., a number of repeating units that results in a polymer with a molecular weight of about 1,500 daltons to about 1,000,000 daltons; about 1500 daltons to about 85,000 daltons, about 1500 daltons to about 75,000 daltons, about 1500 daltons to about 60,000 daltons, about 1500 daltons to about 50,000 daltons, about 1500 daltons to about 35,000 daltons, about 1500 daltons to about 20,000 daltons, about 1500 daltons to about 15,000 daltons, or about 1500 daltons to about 10,000 daltons, calculated by Gel Permeation Chromatography (GPC) relative to narrow molecular weight polystyrene standards.

Further, the polymers of the invention can have an average molecular weight of about 1500 daltons to about 1,000,000 daltons. The compounds that form the R group contained within the polymer structure can have one carboxylic acid group and at least one amine, thiol, alcohol or phenol group. Thus, when R is the residue of a therapeutic agent (drug), these polymers can function as drug delivery systems, which provide an effective means to deliver drugs in a controlled fashion as a function of polymer degradation to any site of a host.

Polyanhydride materials have been extensively studied; for example, see U.S. Pat. Nos. 4,757,128, 4,997,904, 4,888,176, 4,857,311, and 5,264,540, as well as International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. For example, higher molecular weight polyanhydrides typically have greater mechanical strength and higher stability. Further, higher molecular weight polyanhydrides can be made into harder and thicker coatings. Accordingly, the invention provides a polymer comprising a backbone that has a plurality of anhydride bonds, wherein the polymer has an average molecular weight of at least about 120,000 daltons.

Preferably, the polymers of the invention have an average molecular weight of at least about 130,000 daltons. Another specific polymer has an average molecular weight of at least about 140,000 daltons. Another specific polymer has an average molecular weight of at least about 150,000 daltons. Another specific polymer has an average molecular weight of at least about 175,000 daltons. Another specific polymer has an average molecular weight of at least about 200,000 daltons. Even more preferable is a polymer has an average molecular weight of at least about 300,000 daltons. Another specific polymer has an average molecular weight of at least about 500,000 daltons. Another specific polymer has an average molecular weight of at least about 600,000 daltons. Another specific polymer has an average molecular weight of at least about 750,000 daltons.

In one embodiment, the polymer comprises a repeating unit with the structure of Figure III, wherein the polymer breaks down into diflunisal over a period of weeks as demonstrated in FIG. 28.

The polymer can be a polyester or a polyamide. In one embodiment, the polymer is comprised of compounds containing at least two free alcohol or phenol groups or at least two free amine groups available for reactions which co-polymerize with carboxylic acid groups or bis(acyl) chlorides.

For example, a polymer of the invention can comprise one or more units of Formula (IV)

$$—R_1\text{-A-L-A-} \qquad (IV)$$

wherein $R_1$ is group that will provide a active compound upon hydrolysis or enzymatic degradation of the polymer; each A is independently an amide linkage, a thioester linkage, or an ester linkage; and L is a linking group.

A polymer of the invention can also be a polymer that comprises one or more units of Formula (V) in the backbone:

$$—R_2\text{-A-L-A-}R_3\text{-A-L-A-} \qquad (V)$$

wherein: $R_2$ and $R_3$ are each independently a group that will yield a active compound upon hydrolysis or enzymatic degradation of the polymer; each A is independently an amide, thioester, or ester linkage; and each L is independently a linking group. Such a polymer, wherein $R_2$ and $R_3$ are groups that will yield differing active compounds upon hydrolysis or enzymatic degradation of the polymer, are particularly useful for the administration of a combination of two therapeutic agents to an animal.

Another exemplary polymer of the invention is a co-polymer that comprises one or more units of Formula (VI) in the backbone:

$$—R\text{-A-}L_2\text{-A-R-A-}L_3\text{-A-} \qquad (VI)$$

wherein: $L_2$ and $L_3$ are each independently a linking group; each A is independently an amide, thioester, or ester linkage; and each R is independently a group that will yield a active compound upon hydrolysis or enzymatic degradation of the polymer. Such a polymer, wherein $L_2$ and $L_3$ are linking groups that impart different physical properties to the polymer, are particularly useful for customizing the physical characteristics of the polymer for a specific application.

In one embodiment, the active agent is salicylic acid.
In one embodiment, the polymer is a poly(ester-ester).

In one embodiment, the polymer comprises a repeating unit with the structure of Formula (VII):

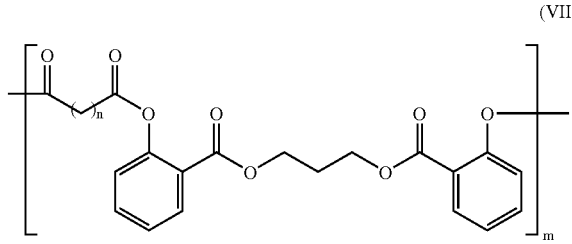

(VII)

n can be any suitable number of carbon atoms, such as, for example, an even number of carbon atoms. A suitable even number of carbon atoms includes any even number of carbon atoms that will result in a functional polymer, e.g., about 2 to about 20 carbon atoms, about 2 to about 18 carbon atoms, about 4 to about 16 carbon atoms, about 4 to about 14 carbon atoms, about 6 to 16 carbon atoms, about 8 to 12 carbon atoms, or about 6 to about 10 carbon atoms.

Further, the nature of the linking group L in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

The linking group may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol, polyvinyl alcohol or polyvinyl pyrrolidone.

The linking group may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The linking group may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

The linking group may be a segment that undergoes thermoreversible gellation, such as Pluronic F127 and poly(N-isopropyl acrylamide). It may incorporate structurally-reinforcing segments, such as polyetherurethane, polyesterurethane, etc.

The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

The linking group may be a peptide or an amino acid. The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms; or a divalent, branched or unbranched, hydrocarbon chain, having from 3 to 15 carbon atoms; or a divalent, branched or unbranched, hydrocarbon chain, having from 6 to 10 carbon atoms, or a divalent hydrocarbon chain having 7, 8, or 9 carbon atoms; or a divalent hydrocarbon chain having 8 carbon atoms.

m can be any suitable number of repeating units, including, e.g., a number of repeating units that results in a polymer with a molecular weight of about 1,500 daltons to about 1,000,000 daltons; about 1500 daltons to about 85,000 daltons, about 1500 daltons to about 75,000 daltons, about 1500 daltons to about 60,000 daltons, about 1500 daltons to about 50,000 daltons, about 1500 daltons to about 35,000 daltons, about 1500 daltons to about 20,000 daltons, about 1500 daltons to about 15,000 daltons, or about 1500 daltons to about 10,000 daltons, calculated by Gel Permeation Chromatography (GPC) relative to narrow molecular weight polystyrene standards.

Further, the polymers of the invention can have an average molecular weight of about 1500 daltons to about 1,000,000 daltons. The compounds that form the R group contained within the polymer structure can have one carboxylic acid group and at least one amine, thiol, alcohol or phenol group. Thus, when R is the residue of a therapeutic agent (drug), these polymers can function as drug delivery systems, which provide an effective means to deliver drugs in a controlled fashion as a function of polymer degradation to any site of a host.

Polyanhydride materials have been extensively studied; for example, see U.S. Pat. Nos. 4,757,128, 4,997,904, 4,888,176, 4,857,311, and 5,264,540, as well as International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. For example, higher molecular weight polyanhydrides typically have greater mechanical strength and higher stability. Further, higher molecular weight polyanhydrides can be made into harder and thicker coatings. Accordingly, the invention provides a polymer comprising a backbone that has a plurality of anhydride bonds, wherein the polymer has an average molecular weight of at least about 120,000 daltons.

Preferably, the polymers of the invention have an average molecular weight of at least about 130,000 daltons. Another specific polymer has an average molecular weight of at least about 140,000 daltons. Another specific polymer has an average molecular weight of at least about 150,000 daltons. Another specific polymer has an average molecular weight of at least about 175,000 daltons. Another specific polymer has an average molecular weight of at least about 200,000 daltons. Even more preferable is a polymer has an average molecular weight of at least about 300,000 daltons. Another specific polymer has an average molecular weight of at least about 500,000 daltons. Another specific polymer has an average molecular weight of at least about 600,000 daltons. Another specific polymer has an average molecular weight of at least about 750,000 daltons.

In one embodiment, the polymer comprises a repeating unit with the structure of Figure VII, and the polymer breaks down over a period of months into salicylic acid as demonstrated in FIG. 28.

Another exemplary polymer of the invention is a co-polymer that comprises one or more units of Formula (IX) in the backbone:

wherein: L is a linking group; each A is independently an amide, thioester, carbonate, carbamate, urethane or ester linkage; and each R is independently a group that will yield a active compound upon hydrolysis or enzymatic degradation of the polymer.

In one embodiment, the active agent is salicylic acid.

In one embodiment, the polymer is a poly(ester-carbonate).

In one embodiment, the polymer comprises a repeating unit with the structure of Formula (X):

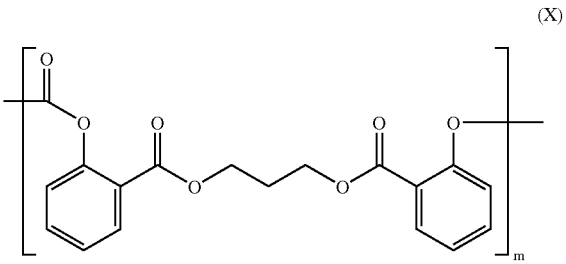

n can be any suitable number of carbon atoms, such as, for example, an even number of carbon atoms. A suitable even number of carbon atoms includes any even number of carbon atoms that will result in a functional polymer, e.g., about 2 to about 20 carbon atoms, about 2 to about 18 carbon atoms, about 4 to about 16 carbon atoms, about 4 to about 14 carbon atoms, about 6 to 16 carbon atoms, about 8 to 12 carbon atoms, or about 6 to about 10 carbon atoms.

Further, the nature of the linking group L in a polymer of the invention is not critical provided the polymer of the invention possesses acceptable mechanical properties and release kinetics for the selected therapeutic application. The linking group L is typically a divalent organic radical having a molecular weight of from about 25 daltons to about 400 daltons. More preferably, L has a molecular weight of from about 40 daltons to about 200 daltons.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

The linking group may incorporate other hydrolytically biodegradable groups such as alpha-ester (lactate, glycolate), e-caprolactone, ortho-ester, or enzymatically biodegradable groups such as amino acids. It may be a water-soluble, non-biodegradable segment such as a polyethylene glycol, polyvinyl alcohol or polyvinyl pyrrolidone.

The linking group may be a water-insoluble, non-biodegradable segment such as polypropylene glycol, polyetherurethane, or poly(n-alkyl ether). It may be an amorphous or semicrystalline biodegradable polymer, such as poly(d,l-lactide), poly(trimethylene carbonate), poly(dioxanone), polyanhydride poly(orthoester) poly(glycolide), poly(l-lactide) poly(e-caprolactone) and copolymers of e-caprolactone, glycolide, trimethylene carbonate, dioxanone, d,l-lactide, l-lactide and d-lactide The linking group may have surfactant properties, such as a Pluronic block copolymer with polyethylene glycol and polypropylene glycol blocks. It may have polar or charged moieties, including carboxylic acid groups from poly(acrylic acid) and poly(alginates), sulfonic acid groups from poly(2-acrylamido-2-methyl-propanesulfonic acid) (AMPS), hydroxy groups from poly(vinyl alcohol), polysaccharides and poly(alginates), and amino groups from poly(L-lysine), poly(2,2-dimethylaminoethyl methacrylate) and poly(amino acids).

The linking group may be a segment that undergoes thermoreversible gellation, such as Pluronic F127 and poly (N-isopropyl acrylamide). It may incorporate structurally-reinforcing segments, such as polyetherurethane, polyesterurethane, etc.

The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a peptide or an amino acid. The linking group may be a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C.sub.1-C.sub.6)alkoxy, (C.sub.3-C.sub.6)cycloalkyl, (C.sub.1-C.sub.6)alkanoyl, (C.sub.1-C.sub.6)alkanoyloxy, (C.sub.1-C.sub.6)alkoxycarbonyl, (C.sub.1-C.sub.6)alkylthio, azido, cyano, nitro, halo, hydroxy, oxo, carboxy, aryl, aryloxy, heteroaryl, and heteroaryloxy.

The linking group may be a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—); or a divalent, branched or unbranched, saturated or unsaturated, hydrocarbon chain, having from 3 to 15 carbon atoms; or a divalent, branched or unbranched, hydrocarbon chain, having from 3 to 15 carbon atoms; or a divalent, branched or unbranched, hydrocarbon chain, having from 6 to 10 carbon atoms; or a divalent hydrocarbon chain having 7, 8, or 9 carbon atoms; or a divalent hydrocarbon chain having 8 carbon atoms.

m can be any suitable number of repeating units, including, e.g., a number of repeating units that results in a polymer with a molecular weight of about 1,500 daltons to about 1,000,000 daltons; about 1500 daltons to about 85,000 daltons, about 1500 daltons to about 75,000 daltons, about 1500 daltons to about 60,000 daltons, about 1500 daltons to about 50,000 daltons, about 1500 daltons to about 35,000 daltons, about 1500 daltons to about 20,000 daltons, about 1500 daltons to about 15,000 daltons, or about 1500 daltons to about 10,000 daltons, calculated by Gel Permeation Chromatography (GPC) relative to narrow molecular weight polystyrene standards.

Further, the polymers of the invention can have an average molecular weight of about 1500 daltons to about 1,000,000 daltons. The compounds that form the R group contained within the polymer structure can have one carboxylic acid group and at least one amine, thiol, alcohol or phenol group. Thus, when R is the residue of a therapeutic agent (drug), these polymers can function as drug delivery systems, which provide an effective means to deliver drugs in a controlled fashion as a function of polymer degradation to any site of a host.

Polyanhydride materials have been extensively studied; for example, see U.S. Pat. Nos. 4,757,128, 4,997,904, 4,888,176, 4,857,311, and 5,264,540, as well as International Patent Application Publication Numbers WO 99/12990, WO 02/09769, and WO 02/09767. Applicants have discovered that anhydride polymers having high average molecular weights possess unexpected and advantageous properties that polymers having lower average molecular weights do not possess. For example, higher molecular weight polyanhydrides typically have greater mechanical strength and higher stability. Further, higher molecular weight polyanhydrides can be made into harder and thicker coatings. Accordingly, the invention provides a polymer comprising a backbone that has a plurality of anhydride bonds, wherein the polymer has an average molecular weight of at least about 120,000 daltons.

Preferably, the polymers of the invention have an average molecular weight of at least about 130,000 daltons. Another specific polymer has an average molecular weight of at least about 140,000 daltons. Another specific polymer has an average molecular weight of at least about 150,000 daltons. Another specific polymer has an average molecular weight of at least about 175,000 daltons. Another specific polymer has an average molecular weight of at least about 200,000 daltons. Even more preferable is a polymer has an average molecular weight of at least about 300,000 daltons. Another specific polymer has an average molecular weight of at least about 500,000 daltons. Another specific polymer has an average molecular weight of at least about 600,000 daltons. Another specific polymer has an average molecular weight of at least about 750,000 daltons.

In one embodiment, the polymer comprises a repeating unit with the structure of Figure X, and the polymer breaks down over a period of months into salicylic acid as demonstrated in FIG. 28.

The polymer can be a polyazo.

In one embodiment, the polymer comprises one or more monomer units of formula (XI):

-A-R$^1$—N=N—R$^1$-(A-L)$_n$-     (XI)

and will have formula (XII)

-(A-R$^1$—N=N—R$^1$-(A-L)$_n$)$_x$-     (XII)

wherein each R$^1$—N is a group that will provide a biologically active compound upon hydrolysis of the polymer; each A is an anhydride, an amide linkage, a thioester linkage, or an ester linkage; and L is a linking group; where n is 0 or 1 and x represents the number of repeating groups (e.g. x can be an integer from 2 to about 100, preferably from 2 to about 50, and more preferably, from 5 to 50). Suitable monomers are polymerized to provide the polyazo compounds.

In one embodiment, the polyazo compound is a compound containing at least one free amine group to form the azo group and at least one free carboxylic acid group, alcohol group or amine group available for reactions which can self-polymerize or co-polymerize with carboxylic acid groups or bis(acyl) chlorides.

In one embodiment, the polymer comprises an active agent incorporated in a poly(azo-anhydride).

In one embodiment, the polymer comprises a polymeric drug delivery system for oral delivery of a drug comprising a poly(azo-anyydride) where the drug is 5-ASA or 4-ASA.

In one embodiment, the polymer has two, or three, or more than three, different R groups that will each provide a different active agent upon hydrolysis of the polymer. Such polymers are particularly useful for the administration of a combination of two or more active agents to a host, such as an animal or plant.

In one embodiment, the polymer is a homopolymer. In another embodiment, the polymer is prepared as a copolymer.

In one embodiment, the polymer comprises a non-steroidal anti-inflammatory agent (NSAID), such as, e.g., salicylic acid and/or diflunisal. Such polymers include for example, polymers comprising repeating units of Formula II, Formula III, Formula VII and/or Formula X. NSAIDs are thought to block the fever, swelling, redness and pain associated with inflammation.

In one embodiment, the polymer is combined with an active agent or agents. The active agent can be combined with the polymer in any suitable manner, such as, e.g., by physically admixing, embedding or dispersing the active agent in the polymer matrix. In one embodiment, the active agent is attached directly to the backbone, chemically linked to the backbone through a linker or spacer molecule, directly or indirectly chemically linked to a chemical group attached to the backbone of the polymer and/or electrostatically attached to the polymer or the polymer backbone. In one embodiment, the active agents can be attached to repeating units of the polymers of the present invention by covalent bonds linked to an Ar ring or an R organic moiety, providing for sustained release of the active agent or it may merely reside in the unoccupied spaces present in the polymer. In another embodiment, the active agent forms a salt with the polymer or the polymer backbone. In one embodiment, the active agent is located in the unoccupied spaces present in a polymer and is present as a homogeneous functional group or it may be incorporated into a salt, micelle, liposome, or heterogeneous aggregate.

In one embodiment, the polymer first comprises a polymer backbone that comprises one or more groups that will provide an active compound or compounds upon hydrolysis or enzymatic degradation of the polymer and, second, an active agent is also physically admixed, embedded or dispersed in the polymer matrix.

In one embodiment, the polymer first comprises a repeating unit with the structure of Formula (III) and, second, diflunisal is also physically admixed, embedded or dispersed in the polymer matrix.

Polymers of the invention preferably have average molecular weights of about 1,500 daltons up to about 100,000 daltons, calculated by Gel Permeation Chromatography (GPC) relative to narrow molecular weight polystyrene standards. IN one embodiment, the polymers have average molecular weights of about 1500 daltons, up to about 35,000 daltons, or up to about 50,000 daltons calculated by Gel Permeation Chromatography (GPC) relative to narrow molecular weight polystyrene standards.

The polymers of the invention can be prepared by any suitable method known in the art, such as, e.g., methods described in International Patent Application WO 99/12990; U.S. patent application Ser. No. 09/917,231; 09/917,194; 09/508,217; 09/422,294; 09/732,516; 60/220,707; 60/261,337; 60/058,328; and 60/220,998; and Conix, Macromol. Synth., 2, 95-99 (1966).

In one embodiment, the polymer is formulated such that it will be released over an extended period of time when administered according to the methods of the invention. For example, the polymer can conveniently be formulated so that it will be released over a period of at least about 2, about 5, about 7, about 10, about 20, about 40, about 60, about 80, about 100, about 120, about 140, about 160, about 180, about 200, about 220, about 240, about 260, about 280, about 300, about 320, about 340, or about 360 days. In one embodiment, the polymer is formulated so that it is released over at least about 5 or about 10 days. In another embodiment, the polymer is formulated so that it is released over at least about 3 months, about 6 months or about 12 months. The polymer can also be formulated so that it is released over a period of about 30 to about 90 days. In another embodiment, the active agent is disassociated from the polymer over a period of about 2 days to about 2 years. For the treatment of hard tissue, in one embodiment, the polymer is formulated so that it is released over a period of about 30 to about 90 days. For the treatment of soft tissue, in one embodiment, the polymer is formulated so that it is released over a period of about 1 to about 30 days, more preferably about 2 to about 25 days. In another embodiment, the polymer is formulated such that it will be released over about 1 to 2 years.

In one embodiment, a suitable polymer has, for example, properties compatible with the therapeutic requirements of the treatment, such as the dosage of drug delivered, the pharmacokinetics, rate of generation, elution or release, and duration of release, elution or generation of the drug, the solubility of the drug and its binding to other biological molecules and components, and the interaction between the drug and other drugs administered systemically or locally. In one embodiment, a suitable polymer also has properties compatible with the physical, chemical, and biological requirements for matching the coating with the surface and bulk of a medical or veterinary device itself, such as the ability of the coating to adhere to the surface of the implanted medical device (during processing/coating as well as during implantation), the stability of the coating on the device, the ability of the coating to be applied reproducibly and reliably to the surface of the device, the ability to coat non-planar, porous, and textured geometries, the ability to fill voids in the device designed as reservoirs for active agents, and the ability of the coating to withstand mechanical (e.g., tensile, compressive, torsional, and shear) and frictional forces generated during processing and application of the coating as well as during the use, implantation, and subsequent tissue response of the implanted medical or veterinary device.

Linking Group (L)

In one embodiment, the polymer of the invention comprises a linking group or groups. In one embodiment, the polymer of the invention comprises backbones wherein active compounds and linking groups (L) are bonded together through ester linkages, thioester linkages, amide linkages, urethane linkages, carbamate linkages, carbonate linkages and others, or a mixture thereof. These linkages form biodegradable bonds that are hydrolyzed, broken by proteolytic process, or broken by other biological of biochemical processes when placed in contact with body tissues or fluids to provide the active compounds.

In one embodiment, the linking group or groups is selected to impart to the polymer one or more desirable physical, chemical, and/or biological properties. Desirable properties include, but are not limited to, adhesion to metallic, polymeric, ceramic or glassy surfaces on implantable medical and veterinary devices to allow formation of a coating that can withstand handling, implantation, and exposure to body tissues and/or fluids post-implantation; sufficient mechanical strength, flexibility, and ability to withstand without failure application of mechanical stress without failure; minimal stickiness on the surface of the resulting coating to minimize adhesion to vehicles used in the delivery or implantation of the medical or veterinary device in the body of a human or animal; and the ability to sterilize the coating and the associated medical or veterinary device by the application of gamma irradiation, electron beam (E beam), treatment with ethylene oxide, or other chemical or physical treatments providing sterilization. Suitable linking groups are described in, e.g., e.g., U.S. Pat. Nos. 6,613,807; 6,328,988; 6,365,146; 6,468,519; 6,486,214; 6,497,895; 6,602,915; 6,613,807; U.S. Published Patent Applns. 2002/0071822 A1; 2002/0106345 A1; 2003/0035787 A1; 2003/0059469 A1; 2003/0104614 A1; 2003/0170202 A1; U.S. patent application Ser. Nos. 09/508,217; 10/368,288; 10/622,072; 10/646,336; 10/647, 701; and International Patent Applns. WO 99/12990; WO 01/28492; WO 01/41753; WO 01/58502; WO 02/09767; WO 02/09768; WO 02/09769, WO 03/005959; WO 03/046034; WO 03/065928; and WO 03/072020.

The nature of the linking group (L) in a polymer of the invention can be manipulated to provide the polymer of the invention with one or more desirable physical, chemical, and/or biological properties, such as, e.g., mechanical and thermal properties; adhesiveness; wettability; hardness; drug generation, and release kinetics and solubility; and tissue compatibility and response for the selected therapeutic application. The linking group L is typically a divalent organic radical having a molecular weight of from about 25 daltons to about 400 daltons. In one embodiment, L has a molecular weight of from about 40 daltons to about 200 daltons.

The mechanical and degradation properties (e.g., hydrolytic properties) of polymers comprising one or more active compounds can be controlled by incorporating and/or modifying a linking group (L) in the polymer backbone. In one embodiment, the selection of the molecular weight and chemical composition of the linking group may affect the glass transition temperature, and accordingly, the mechanical properties of the therapeutic polymers and coatings of the therapeutic polymers at body temperatures. The higher the molecular weight, the greater the toughness of the material in terms of elasticity and tear strength will be.

The linking group L typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking) for appending other molecules (e.g. another active compound) to the polymer, for changing the solubility of the polymer, or for effecting the biodistribution of the polymer.

In one embodiment, the linker has two or more functional groups. These groups can independently be a hydroxy group (—OH), a mercapto group (—SH), an amine group (—NHR), and a carboxylic acid (—COOH), as well as others. These functionalities form biodegradable bonds with the drug to be polymerized that are hydrolyzed, broken by proteolytic process, or broken by other biological of biochemical processes when placed in contact with body tissues or fluids.

In one embodiment, L is an amino acid or a peptide.

In one embodiment, L is a divalent, branched or unbranched, saturated or unsaturated, hydrocarbon chain, having from about 3 to about 15 carbon atoms; from about 6 to about 12 carbon atoms; or having about 7, about 8, about 9, or about 10 carbon atoms.

In one embodiment, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—).

In one embodiment, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

In one embodiment, L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

In one embodiment, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In one embodiment, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of ($C_1$-$C_6$) alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo, carboxy, aryl, aryloxy, heteroaryl, and heteroaryloxy.

In one embodiment, L is a dicarboxylic acid hydrocarbon chain with an even number of carbon atoms. The polymer may comprise one or more species of L. More preferably, L is a dicarboxylic acid hydrocarbon chain with between 4 and 14 carbon atoms, and more preferably between 6 and 10 carbon atoms. Such a linker can be used with any suitable active agent, such as, e.g., salicylic acid or a derivative.

In one embodiment, L is a dicarboxylic acid hydrocarbon chain with an even number of carbon atoms. The polymer may comprise one or more species of L. More preferably, the specific value for L is a dicarboxylic acid hydrocarbon chain with between 6 and 16 carbon atoms, and more preferably between 8 and 12 carbon atoms. Such a linker is appropriate for use with any suitable active agent, such as active agents listed herein, e.g., diflunisal.

Active Agents

Any suitable active agent can be employed in the polymers of the invention. In one embodiment, the active agents that can be incorporated into the polymers of the invention possess at least two functional groups that can each be incorporated into an ester, thioester, urethane, carbamate, carbonate or amide linkage of a polymer, such that, upon hydrolysis or enzymatic degradation of the polymer, the active agent is obtained.

In one embodiment, the functional groups can independently be a hydroxy group (—OH), a mercapto group (—SH), an amine group (—NHR), or a carboxylic acid (—COOH). These functionalities form biodegradable bonds with the drug to be polymerized that are hydrolyzed, broken by proteolytic process, or broken by other biological of biochemical processes when placed in contact with body tissues or fluids.

An active agent can also comprise other functional groups (including hydroxy groups, mercapto groups, amine groups, and carboxylic acids, as well as others) that can be used to modify the properties of the polymer (e.g. for branching, for cross linking, for appending other molecules (e.g. another active compound) to the polymer, for changing the solubility of the polymer, or for effecting the biodistribution of the polymer). One skilled in the art can readily select active agents that possess the necessary functional groups for incorporation into the polymers of the invention from these lists.

An active agent can be a therapeutic agent. Therapeutic agents that can be incorporated into the polymers of the invention include, e.g., suitably functionalized analgesics, anesthetics, antiacne agents, antibiotics, anticholinergics, anticoagulants, anticonvulsants, antidiabetic agents, antidyskinetics, antifibrotic agents, antifungal agents, antiglaucoma agents, anti-infectives, anti-inflammatory compounds, antimicrobial compounds, antineoplastics, anti-Parkinson's agents, antiosteoporotics, antiseptics, antisporatics, antithrombotics, antiviral compounds, bacteriostatic compounds, bone resorption inhibitors, calcium regulators, cardioprotective agents, cardiovascular agents, central nervous system stimulants, cholinesterase inhibitors, contraceptives, deodorants, disinfectants, dopamine receptor agonists, erectile dysfunction agents, fertility agents, gastrointestinal agents, gout agents, hormones, hypnotics, immunomodulators, immunosuppressives, keratolytics, migraine agents, motion sickness agents, muscle relaxants, nucleoside analogs, obesity agents, opthalmic agents, osteoporosis agents, parasympatholytics, parasympathomimetics, prostaglandins, psychotherapeutic agents, respiratory agents, sclerosing agents, sedatives, skin and mucous membrane agents, smoking cessation agents, sympatholytics, ultraviolet screening agents, urinary tract agents, vaginal agents, and vasodilators. (see Physicians' Desk Reference, 55 ed., 2001, Medical Economics Company, Inc., Montvale, N.J., pages 201-202). Suitable active agents can be found, for example, in: Physician's Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J.

Examples of suitable active agents include, e.g., 2-p-sulfanilyanilinoethanol; 3-amino-4-hydroxybutyric acid; 4,4'-sulfinyldianiline; 4-sulfanilamidosalicylic acid; 6-azauridine; 6-diazo-5-oxo-L-norleucine; 6-mercaptopurine; aceclofenac; acediasulfone; acetosulfone; aclacinomycin(s); acriflavine; acyclovir; albuterol; alendronate; alminoprofen; amfenac; amicarbilide; amikacin; aminoquinuride; amiprilose; amoxicillin; amphotericin B; ampicillin; ancitabine; anthramycin; apalcillin; apicycline; apramycin; arbekacin; argatroban; arsphenamine; aspoxicillin; atorvastatin; azacitadine; azaserine; azidamfenicol; azithromycin; aztreonam; bacitracin; bambermycin(s); benazepril; bialamicol; biapenem; bleomycin(s); brodimoprim; bromfenac; bromosaligenin; bucillamine; budesonide; bumadizon; buprenorphine; butethamine; butirosin; butorphanol; candicidin(s); capecitabine; capreomycin; captopril; carbenicillin; carbomycin; carboplatin; carprofen; carubicin; carumonam; carzinophillin A; cefaclor; cefadroxil; cefamandole; cefatrizine; cefbuperazone; cefclidin; cefdinir; cefditoren; cefepime; cefetamet; cefixime; cefinenoxime; cefminox; cefodizime; cefonicid; cefoperazone; ceforanide; cefotaxime; cefotetan; cefotiam; cefozopran; cefpimizole; cefpiramide; cefpirome; cefprozil; cefroxadine; ceftazidime; cefteram; ceftibuten; ceftriaxone; cefuzonam; cephalexin; cephaloglycin; cephalosporin C; cephradine; chloramphenicol; chloroazodin; chloroazodin; chlorozotocin; chlorphenesin; chlortetracycline; chromomycin(s); cilastatin; ciprofloxacin; cladribine; clarithromycin; clinafloxacin; clindamycin; clomocycline; colistin; coumetarol; cyclacillin; cyclosporin; cytarabine; dapsone; daunorubicin; demeclocycline; denopterin; dermostatin(s); diathymosulfone; dibekacin; diclofenac; dicoumarol; diflunisal; dihydrostreptomycin; dirithromycin; ditazol; docetaxel; dopamine; doxifluridine; doxorubicin; doxycycline; edatrexate; eflornithine; elliptinium; enalapril; enfenamic acid; enocitabine; enoxacin; enviomycin; epicillin; epirubicin; erythromycin; ethyl biscoumacetate; ethylidene; etodolac; etofenamate; etoposide; famotidine; fenalcomine; fendosal; fepradinol; filipin; flomoxef; floxuridine; fludarabine phosphate; flufenamic acid; fluvastatin; fortimicin(s); fungichromin; gemcitabine; gentamicin(s); gentisic acid; glucamethacin; glucosulfone; glycol salicylate; gramicidin S; gramicidin(s); grepafloxacin; guamecycline; gusperimus; hetacillin; hydroxytetracaine; idarubicin; iloprost; imipenem; indinavir; isepamicin; josamycin; kanamycin(s); lamifiban; lamivudine; leucomycin(s); leuprolide; lincomycin; lisinopril; lisinpril; lomefloxacin; lucensomycin; lymecycline; mannomustine; meclocycline; meclofenamic acid; mefenamic acid; melphalan; menogaril; mepartricin; meropenem; mesalamine; metformin; methacycline; methotrexate; methsalamine; metoprolol; micronomicin; midecamycin(s); minocycline; mitobronitol; mitolactol; mitomycin C; mitoxantrone; mopidamol; morphine; moxalactam; mupirocin; mycophenolic acid; nadifloxacin; naepaine; nalbuphine; natamycin; neomycin; netilmicin; niflumic acid; nizatidine; nogalamycin; norfloxacin; nystatin; oleandomycin; oligomycin(s); olivomycin(s); olsalazine; orthocaine; oxaceprol; oxymorphone; oxytetracycline; paclitaxel; panipenem; paromomycin; pazufloxacin; penicillin N; pentostatin; peplomycin; perimycin A; phenamidine; pipacycline; pipemidic acid; pirarubicin; piridocaine; piritrexim; plicamycin; podophyllinic acid 2-ethylhydrazine; polymyxin; pravastatin; prednimustine; primycin; procarbazine; procodazole; p-sulfanilylbenzylamine; pteropterin; puromycin; quinacillin; quinapril; ranimustine; ranitidine; ribostamycin; rifamide; rifampin; rifamycin SV; rifapentine; rifaximin; ristocetin; ritipenem; rokitamycin; rolitetracycline; romurtide; rosaramycin; roxithromycin; S-adenosylmethionine; salazosulfadimidine; salicyl alcohol; salicylic acid; salmeterol; salsalate; sancycline; sirolimus (rapamycin); sisomicin; solasulfone; sparfloxacin; spectinomycin; spiramycin; streptomycin; streptonigrin; streptozocin; succisulfone; sulfachrysoidine; sulfaloxic acid; sulfamidochrysoidine; sulfanilic acid; sulfasalazine; sulfoxone; tacrolimus; taprostene; teicoplanin; temafloxacin; temocillin; teniposide; tetracycline; tetroxoprim; thiamiprine; thiamphenicol; thiazolsulfone; thioguanine; thiostrepton; ticarcillin; tigemonam; tioclomarol; tirofiban; tobramycin; tolfenamic acid; Tomudex7 (N-[[5-[[(1,4-Dihydro-2-methyl-4-oxo-6-quinazolinyl)methyl]methylamino]-2-thienyl]carbonyl]-L-glutamic acid), topotecan; tosufloxacin; trimethoprim; trimetrexate; trospectomycin; trovafloxacin; tuberactinomycin; tubercidin; ubenimex; vancomycin; vinblastine; vincristine; vindesine;

vinorelbine; xinafoate; zidovudine; zorubicin; and any enantiomers, derivatives, bases, salts or mixtures thereof.

In one embodiment, the active agent is a nonsteroidal anti-inflammatory drug, for example, a nonsteroidal anti-inflammatory drug as described in U.S. patent application Ser. No. 09/732,516, filed 7 Dec. 2000), 3-amino-4-hydroxybutyric acid, aceclofenac, alminoprofen, amfenac, bromfenac, bromosaligenin, bumadizon, carprofen, diclofenac, diflunisal, ditazol, enfenamic acid, etodolac, etofenamate, fendosal, fepradinol, flufenamic acid, gentisic acid, glucamethacin, glycol salicylate, meclofenamic acid, mefenamic acid, mesalamine, niflumic acid, olsalazine, oxaceprol, S-adenosylmethionine, salicylic acid, salsalate, sulfasalazine, tolfenamic acid and the like.

In one embodiment, the active agent is an anti-bacterial, for example, 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clomocycline, colistin, cyclacillin, dapsone, demeclocycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, vancomycin and the like.

In one embodiment, the active agent is an anti-fungal, for example, amphotericin B, azaserine, candicidin(s), chlorphenesin, dermostatin(s), filipin, fungichromin, lucensomycin, mepartricin, natamycin, nystatin, oligomycin(s), perimycin A, tubercidin and the like.

In one embodiment, the active agent is an anti-cancer (e.g., carcinomas, sarcomas, leukemias and cancers derived from cells of the nervous system), including anti-neoplastic, for example, 6-azauridine, 6-diazo-5-oxo-L-norleucine, 6-mercaptopurine, aclacinomycin(s), ancitabine, anthramycin, azacitadine, azaserine, bleomycin(s), capecitabine, carubicin, carzinophillin A, chlorozotocin, chromomycin(s), cladribine, cytarabine, daunorubicin, denopterin, docetaxel, doxifluridine, doxorubicin, edatrexate, eflornithine, elliptinium, enocitabine, epirubicin, etoposide, floxuridine, fludarabine, gemcitabine, idarubicin, mannomustine, melphalan, menogaril, methotrexate, mitobronitol, mitolactol, mitomycin C, mitoxantrone, mopidamol, mycophenolic acid, nogalamycin, olivomycin(s), paclitaxel, pentostatin, peplomycin, pirarubicin, piritrexim, plicamycin, podophyllinic acid 2-ethylhydrazine, prednimustine, procarbazine, pteropterin, puromycin, ranimustine, streptonigrin, streptozocin, teniposide, thiamiprine, thioguanine, Tomudex7 (N-[[5-[[(1,4-Dihydro-2-methyl-4-oxo-6-quinazolinyl)methyl]methylamino]-2-thienyl]carbonyl]-L-glutamic acid), toptecan, trimetrexate, tubercidin, ubenimex, vinblastine, vindesine, vinorelbine, zorubicin and the like.

In one embodiment, the active agent is an anti-thrombotic, for example, argatroban, coumetarol, dicoumarol, ethyl biscoumacetate, ethylidene dicoumarol, iloprost, lamifiban, taprostene, tioclomarol, tirofiban and the like.

In one embodiment, the active agent is an immunosuppressive, for example, 6-mercaptopurine, amiprilose, bucillamine, gusperimus, mycophenolic acid, procodazole, romurtide, sirolimus (rapamycin), tacrolimus, ubenimex and the like.

In one embodiment, the active agent is a general or local anesthetic, for example, butethamine, fenalcomine, hydroxytetracaine, naepaine, orthocaine, piridocaine, salicyl alcohol and the like.

In one embodiment, the active agent is a low molecular weight drug suitable for linkage into degradable copolymers via a polyanhydride. Such low molecular weight drugs typically have a relatively low molecular weights of approximately 1,000 daltons or less. The drug also contains within its molecular structure one carboxylic acid group and at least one carboxylic acid (—COOH), amine (—NHR), thiol (—SH), alcohol (—OH) or phenol (Ph-OH) group. Suitable examples of low molecular weight drugs with the required functional groups within their structure can be found in almost all classes of drugs including, but not limited to, analgesics, anesthetics, antiacne agents, antibiotics, synthetic antibacterial agents, anticholinergics, anticoagulants, antidyskinetics, antifibrotics, antifungal agents, antiglaucoma agents, anti-inflammatory agents, antineoplastics, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents.

Medical Devices, Compositions and Therapeutic Methods

The biocompatible, biodegradable polymers of the invention are useful in a variety of applications where delivery of an active agent or agents is desired.

In one embodiment, the polymers described herein can be used to form, coat or otherwise treat medical devices.

The medical device of the invention can be any suitable medical device, such as, for example, a medical device that is implanted into a patient. In one embodiment of the invention, polymers of the invention are used to form or coat shaped articles such as vascular grafts and stents, bone plates, sutures, wound closing staples, surgical meshes, dental implants, implantable sensors, implantable drug delivery devices, stents for tissue regeneration, and other articles suitable for implantation into a patient.

Suitable medical devices include, for example, stents, e.g., coronary vascular stents, peripheral vascular stents, urethral stents, biliary stents, stents used for supporting the lumen of other anatomical tubes, and stents used for other medical treatments; catheters, e.g., surgical catheters and urinary catheters; grafts; and orthopedic implants including, e.g., hip, knee and shoulder implants, internal and external fixation devices and spinal cages.

Medical devices useful with coverings of the present invention include, but are not limited to, a fixation device, catheters, drain tubes, intravenous tubes, tampon applicators, ventilator tubes, endoscopes, arthroscopes, needles, condoms, barrier devices, diagnostic devices (e.g., speculum), dental appliances, and surgical appliances. The above identified polymers, compounds and/or compositions including a active agent or compound, or drug molecule of the invention can be formed into a medical implant (e.g., medical, dental, and surgical implants) or applied or coated onto a medical implant. For example, in addition to the implants described above, implants for vascular, cardiovascular, coronary, peripheral vascular, orthopedic, dental, oro-maxillary, gastrointestinal, urogenital, ophthalmic, gynecological, pulmonary, surgical, physiological, metabolic, neurological, diagnostic and therapeutic uses, may be formed from or applied or coated with the above identified polymers, compounds and/or compositions. Such implants include, but are not limited to, stents, catheters, balloons, guidewires, grafts, sutures, meshes, joint prostheses, breast prostheses, fracture management devices, drug dosing devices, pacemakers, mechanical pumps, dental implants (e.g., dental, oro-maxillary, and alveolar), defibrillators, and filters. Suitable medical implants also include, but are not limited to:

the following Boston Scientific (Boston Scientific Corporation, Natick, Mass.) products: Polaris™, NIR® Elite OTW Stent System, NIR® Elite Monorail™ Stent System, Magic WALLSTENT® Stent System, Radius® Self Expanding Stent, NIR® Biliary Stent System, NIROYAL™ Biliary Stent System, WALLGRAFT® Endoprosthesis, WALLSTENT® Endoprosthesis, RX Plastic Biliary Stents, UroMax Ultra™ High Pressure Balloon Catheter, Passport™ Balloon on a Wire Catheter, Excelsior™ 1018™ Microcatheter, Spinnaker® Elite™ Flow-Directed Microcatheter, Guider Softip™ XF Guide Catheters, Sentry™ Balloon Catheters, Flexima™ APD™ Drainage Catheters with Twist Loc™ Hub, Vaxcel™ Chronic Dialysis Catheter, PASV® PICC Peripherally Inserted Central Catheters, Chilli® Cooled Ablation Catheters, and Constellation® Catheters;

the following Cordis (Cordis, a Johnson & Johnson Company, Piscataway, N.J.) products: BX Velocity™ Coronary Stents, Ninja FX™ Balloon Catheters, Raptor™ Balloon Catheters, NC Raptor™ Balloon Catheters, Predator™ Balloon Catheters, Titan Mega™ Balloon Catheters, Checkmate™ Brachytherapy Catheters, Infiniti™ Diagnostic Catheters, Cinemayre™ Diagnostic Catheters, SuperTorque Plus™ Diagnostic Catheters, and High Flow™ Diagnostic Catheters;

the following Medtronics (Medtronics, Inc., Minneapolis, Minn.) products: Aneurx Stentgraft, S7 Coronary Stents, S670 Coronary Stents, S660 Coronary Stents, BeStent 2 Coronary Stents, D1 Balloon Catheters, and D2 Balloon Catheters;

the following Avantec Vascular (Avantec Vascular, San Jose, Calif.) products: Duraflex™ Coronary Stent System, and Apollo™ Coronary Dilatation Catheter;

the following B. Braun (B. Braun Medical Ltd., Sheffield, England) products: Coroflex™ Coronary Stent, Cystofix™ Urogenital Catheters, and Urecath™ Urogenital Catheters;

the following Cook (Cook Group Inc., Bloomington, Ind.) products: V-Flex Plus™ Coronary Stent, and CR II® Coronary Stent;

the following Guidant (Guidant Corporation, Indianapolis, Ind.) products: Multilink Penta™ Coronary Stents, Multilink Pixel™ Coronary Stents, Multilink Ultra™ Coronary Stents, Multilink Tetra™ Coronary Stents, Multilink Tristar™ Coronary Stents, Ancure™ Stentgraft, Dynalink™ Biliary Stents, Rx Herculink™ Biliary Stents, Omnilink™ Biliary Stents, Megalink™ Biliary Stents, Rx Crosssail™ Balloon Dilatation Catheters, Rx Pauersail™ Balloon Dilatation Catheters, OTW Opensail™ Bailbon Dilatation Catheters, OTW Highsail™ Balloon Dilatation Catheters, Rx Esprit™ Balloon Dilatation Catheters, Rx Viatrac™ Peripheral Catheters, and OTW Viatrac™ Peripheral Catheters;

the following Ethicon (Ethicon, a Johnson & Johnson Company, Piscataway, N.J.) products: Vicryl™ (resorbable braided coated), Pronova™, and Panacryl™;

the following USS/DG Sutures (U.S. Surgical, a division of Tyco Healthcare Group LP, Norwalk, Conn.) products: Decon II™ (coated, braided synthetic, absorbable), PolySorb™ (coated, braided synthetic, absorbable), Dexon S™ (Uncoated, braided synthetic, absorbable), Gut sutures (absorbable), Biosyn™ (synthetic monofilament, absorbable), Maxon™ (synthetic monofilament, absorbable), Surgilon™ (braided nylon, non-absorbable), Ti-Cron™ (coated, braided polyester, non-absorbable), Surgidac™ (coated, braided polyester, non-absorbable), SofSilk™ (coated, braided silk, non-absorbable), Dermalon™ (nylon monofilament, non-absorbable), Monosof™ (nylon monofilament, non-absorbable), Novafil™ (polybutester monofilament, non-absorbable), Vascufil™ (coated polybutester monofilament, non-absorbable), Surgilene™ (polypropylene monofilament, non-absorbable), Surgipro™ (polypropylene monofilament, non-absorbable), Flexon™ (stainless steel monofilament, non-absorbable), SURGALLOY™ needle, and SURGALLOY™ OptiVis™ needle;

the following Surgical Dynamics (Surgical Dynamics, Inc., North Haven, Conn.) products: S*D*Sorb™ (suture anchor, Anchor Sew™ (suture anchor), S*D*Sorb E-Z Tac™ (bio-resorbable implant w/o sutures), S*D*Sorb Meniscal Stapler™ (delivers bio-absorbable repair implant), Ray Threaded Fusion Cage™ (spine), Aline™ (cervical plating system), SecureStrand™ (spinal reconstruction cable), and Spiral Radius 90D™ (spinal rod system);

the following Zimmer (Zimmer, Warsaw, Ind.) products: VerSys™ cemented stem hip system, VerSys Heritage™ Hip cemented stem hip system, VerSys™ LD/Fx cemented stem hip system, CPT™ Hip cemented stem hip system, VerSys™ Cemented Revision/Calcar cemented stem hip system, Mayo™ Hip porous stem hip system, VerSys™ Beaded MidCoat porous stem hip system, VerSys™ Beaded FullCoat Plus porous stem hip system, VerSys™ Fiber Metal MidCoat porous stem hip system, and VerSys™ Fiber Metal Taper porous stem hip system, VerSys™ LD/Fx press-fit hip system, VerSys™ Cemented Revision/Calcar revision stem hip system, ZMR™ hip revision stem hip system, Trilogy™ Cup acetabular cup hip system, ZCA™ cup acetabular cup hip system, Longevity™ polyethylene hip system, Calcicoat™ coating hip system, NexGen™ Implant knee system, NexGen™ Instruments knee system, NexGen™ Revision Instruments knee system, IM™ Instruments knee system, MICROMILL™ 5-in-1 Instruments knee system, Multi-Reference™ 4-in-1 knee system, V-STA™ Instruments knee system, CoonradlMorrey™ elbow, Bigliani/Flatow™ shoulder, Cable Ready™ Cable Grip System, Collagraft™ Bone Graft Matrix, Herbert™ Bone Screw, M/DN™ Intramedullary Fixation, Mini Magna-Fx™ Screw Fixation, Magna-Fx™ Screw Fixation, Periarticular™ Plating System, Versa-Fx™ Femoral Fixation system, Versa-Fix II™ Femoral Fixation System, and Trabecular™ Metal;

and the following Alza technologies (ALZA Corporation, Mountain View, Calif.) products: DUROS® Implant, OROS™ osmotic, D-TRANS™ transdermal, STEALTH™ liposomal, E-TRANS™ electrotransport, Macroflux™, and ALZAMER depot;

as well as those described in: Stuart, M., "Technology Strategies, Stent and Deliver," *Start-Up, Windhover's Review of Emerging Medical Ventures*, pp. 34-38, June 2000); van der Giessen, Willem J., et al. "Marked Inflammatory Sequelae to Implantation of Biodegradable and Nonbiodegradable Polymers in Porcine Coronary Arteries," *Circulation*, Vol. 94, No. 7, pp. 1690-1697 (Oct. 1, 1996); Gunn, J. et al., "Stent coatings and local drug delivery," *European Heart Journal*, 20, pp. 1693-1700 (1999);

European Patent Applications: 01301671, 00127666, 99302918, 95308988, 95306529, 95302858, 94115691, 99933575, 94922724, 97933150, 95308988, 91309923, 91906591, and 112119841;

PCT Publications: WO 00/187372, WO 00/170295, WO 00/145862, WO 00/143743, WO 00/044357, WO 00/009672, WO 99/03517, WO 99/00071, WO 98/58680, WO 98/34669, WO 98/23244, and WO 97/49434;

U.S. application Ser. Nos. 061,568, 346,263, 346,975, 325, 198, 797,743, 815,104, 538,301, 430,028, 306,785, and 429, 459; and U.S. Pat. Nos. 6,325,825, 6,325,790, 6,322,534, 6,315, 708, 6,293,959, 6,289,568, 6,273,913, 6,270,525, 6,270,521, 6,267,783, 6,267,777, 6,264,687, 6,258,116, 6,254,612, 6,245,100, 6,241,746, 6,238,409, 6,214,036, 6,210,407, 6,210,406, 6,210,362, 6,203,507, 6,198,974, 6,190,403, 6,190,393, 6,171,277, 6,171,275, 6,165,164, 6,162,243, 6,140,127, 6,134,463, 6,126,650, 6,123,699, 6,120,476, 6,120,457, 6,102,891, 6,096,012, 6,090,104, 6,068,644, 6,066,125, 6,064,905, 6,063,111, 6,063,080, 6,039,721, 6,039,699, 6,036,670, 6,033,393, 6,033,380, 6,027,473, 6,019,778, 6,017,363, 6,001,078, 5,997,570, 5,980,553, 5,971,955, 5,968,070, 5,964,757, 5,948,489, 5,948,191, 5,944,735, 5,944,691, 5,938,682, 5,938,603, 5,928,186, 5,925,301, 5,916,158, 5,911,732, 5,908,403, 5,902,282, 5,897,536, 5,897,529, 5,897,497, 5,895,406, 5,893,885, 5,891,108, 5,891,082, 5,882,347, 5,882,335, 5,879,282, RE36,104, 5,863,285, 5,853,393, 5,853,389, 5,851,464, 5,846,246, 5,846,199, 5,843,356, 5,843,076, 5,836,952, 5,836,875, 5,833,659, 5,830,189, 5,827,278, 5,824,173, 5,823,996, 5,820,613, 5,820,594, 5,811,814, 5,810,874, 5,810,785, 5,807,391, 5,807,350, 5,807,331, 5,803,083, 5,800,399, 5,797,948, 5,797,868, 5,795,322, 5,792,415, 5,792,300, 5,785,678, 5,783,227, 5,782,817, 5,782,239, 5,779,731, 5,779,730, 5,776,140, 5,772,590, 5,769,829, 5,759,179, 5,759,172, 5,746,764, 5,741,326, 5,741,324, 5,738,667, 5,736,094, 5,736,085, 5,735,831, 5,733,400, 5,733,299, 5,728,104, 5,728,079, 5,728,068, 5,720,775, 5,716,572, 5,713,876, 5,713,851, 5,713,849, 5,711,909, 5,709,653, 5,702,410, 5,700,242, 5,693,021, 5,690,645, 5,688,249, 5,683,368, 5,681,343, 5,674,198, 5,674,197, 5,669,880, 5,662,622, 5,658,263, 5,658,262, 5,653,736, 5,645,562, 5,643,279, 5,634,902, 5,632,763, 5,632,760, 5,628,313, 5,626,604, 5,626,136, 5,624,450, 5,620,649, 5,613,979, 5,613,948, 5,611,812, 5,607,422, 5,607,406, 5,601,539, 5,599,319, 5,599,310, 5,598,844, 5,593,412, 5,591,142, 5,588,961, 5,571,073, 5,569,220, 5,569,202, 5,569,199, 5,562,632, 5,562,631, 5,549,580, 5,549,119, 5,542,938, 5,538,510, 5,538,505, 5,533,969, 5,531,690, 5,520,655, 5,514,236, 5,514,108, 5,507,731, 5,507,726, 5,505,700, 5,501,341, 5,497,785, 5,497,601, 5,490,838, 5,489,270, 5,487,729, 5,480,392, 6,325,800, 6,312,404, 6,264,624, 6,238,402, 6,174,328, 6,165,127, 6,152,910, 6,146,389, 6,136,006, 6,120,454, 6,110,192, 6,096,009, 6,083,222, 6,071,308, 6,048,356, 6,042,577, 6,033,381, 6,032,061, 6,013,055, 6,010,480, 6,007,522, 5,968,092, 5,967,984, 5,957,941, 5,957,863, 5,954,740, 5,954,693, 5,938,645, 5,931,812, 5,928,247, 5,928,208, 5,921,971, 5,921,952, 5,919,164, 5,919,145, 5,868,719, 5,865,800, 5,860,974, 5,857,998, 5,843,089, 5,842,994, 5,836,951, 5,833,688, 5,827,313, 5,827,229, 5,800,391, 5,792,105, 5,766,237, 5,766,201, 5,759,175, 5,755,722, 5,755,685, 5,746,745, 5,715,832, 5,715,825, 5,704,913, 5,702,418, 5,697,906, 5,693,086, 5,693,014, 5,685,847, 5,683,448, 5,681,274, 5,665,115, 5,656,030, 5,637,086, 5,607,394, 5,599,324, 5,599,298, 5,597,377, 5,578,018, 5,562,619, 5,545,135, 5,544,660, 5,514,112, 5,512,051, 5,501,668, 5,489,271, 6,319,287, 6,287,278, 6,221,064, 6,113,613, 5,984,903, 5,910,132, 5,800,515, 5,797,878, 5,769,786, 5,630,802, 5,492,532, 5,322,518, 5,279,563, 5,213,115, 5,156,597, 5,135,525, 5,007,902, 4,994,036, 4,981,475, 4,951,686, 4,929,243, 4,917,668, 4,871,356, 6,322,582, 6,319,445, 6,309,202, 6,293,961, 6,254,616, 6,206,677, 6,205,748, 6,178,622, 6,156,056, 6,128,816, 6,120,527, 6,105,339, 6,081,981, 6,076,659, 6,058,821, 6,045,573, 6,035,916, 6,035,751, 6,029,805, 6,024,757, 6,022,360, 6,019,768, 6,015,042, 6,001,121, 5,987,855, 5,975,876, 5,970,686, 5,956,927, 5,951,587, RE36,289, 5,924,561, 5,906,273, 5,894,921, 5,891,166, 5,887,706, 5,871,502, 5,871,490, 5,855,156, 5,853,423, 5,843,574, 5,843,087, 5,833,055, 5,814,069, 5,813,303, 5,792,181, 5,788,063, 5,788,062, 5,776,150, 5,749,898, 5,732,816, 5,728,135, 5,709,067, 5,704,469, 5,695,138, 5,692,602, 5,683,416, 5,681,351, 5,675,961, 5,669,935, 5,667,155, 5,655,652, 5,628,395, 5,623,810, 5,601,185, 5,571,469, 5,555,976, 5,545,180, 5,529,175, 5,500,991, 5,495,420, 5,491,955, 5,491,954, 5,487,216, 5,487,212, 5,486,197, 5,485,668, 5,477,609, 5,473,810, 5,409,499, 5,364,410, 5,358,624, 5,344,005, 5,341,922, 5,306,280, 5,284,240, 5,271,495, 5,254,126, 5,242,458, 5,236,083, 5,234,449, 5,230,424, 5,226,535, 5,224,948, 5,213,210, 5,199,561, 5,188,636, 5,179,818, 5,178,629, 5,171,251, 5,165,217, 5,160,339, 5,147,383, 5,102,420, 5,100,433, 5,099,994, 5,089,013, 5,089,012, 5,080,667, 5,056,658, 5,052,551, 5,007,922, 4,994,074, 4,967,902, 4,961,498, 4,896,767, 4,572,363, 4,555,016, 4,549,649, 4,533,041, 4,491,218, 4,483,437, 4,424,898, 4,412,614, D260,955, 4,253,563, 4,249,656, 4,127,133, D245,069, 3,972,418, 3,963,031, 3,951,261, 3,949,756, 3,943,933, 3,942,532, 3,939,969, 6,270,518, 6,213,940, 6,203,564, 6,191,236, 6,138,440, 6,135,385, 6,074,409, 6,053,086, 6,016,905, 6,015,427, 6,011,121, 5,988,367, 5,961,538, 5,954,748, 5,948,001, 5,948,000, 5,944,739, 5,944,724, 5,939,191, 5,925,065, 5,910,148, 5,906,624, 5,904,704, 5,904,692, 5,903,966, 5,891,247, 5,891,167, 5,889,075, 5,865,836, 5,860,517, 5,851,219, 5,814,051, 5,810,852, 5,800,447, 5,782,864, 5,755,729, 5,746,311, 5,741,278, 5,725,557, 5,722,991, 5,709,694, 5,709,692, 5,707,391, 5,701,664, 5,695,879, 5,683,418, 5,669,490, 5,667,528, 5,662,682, 5,662,663, 5,649,962, 5,645,553, 5,643,628, 5,639,506, 5,615,766, 5,608,962, 5,584,860, 5,534,857, 5,573,542, 5,569,302, 5,568,746, 5,566,822, 5,566,821, 5,562,685, 5,560,477, 5,554,171, 5,549,907, 5,540,117, 5,531,763, 5,527,323, 5,520,702, 5,520,084, 5,514,159, 5,507,798, 5,507,777, 5,503,266, 5,494,620, 5,480,411, 5,480,403, 5,462,558, 5,462,543, 5,460,263, 5,456,697, 5,456,696, 5,442,896, 5,435,438, 5,425,746, 5,425,445, 5,423,859, 5,417,036, 5,411,523, 5,405,358, 5,403,345, 5,403,331, 5,394,971, 5,391,176, 5,386,908, 5,383,905, 5,383,902, 5,383,387, 5,376,101, D353,672, 5,368,599, D353,002, 5,359,831, 5,358,511, 5,354,298, 5,353,922, 5,350,373, 5,349,044, 5,335,783, 5,335,775, 5,330,442, 5,325,975, 5,318,577, 5,318,575, 5,314,433, 5,312,437, 5,310,348, 5,306,290, 5,306,289, 5,306,288, 5,294,389, 5,282,832, 5,282,533, 5,280,674, 5,279,783, 5,275,618, 5,269,807, 5,261,886, 5,261,210, 5,259,846, 5,259,845, 5,249,672, 5,246,104, 5,226,912, 5,225,485, 5,217,772, 5,217,486, 5,217,485, 5,207,679, D334,860, 5,197,597, 5,192,303, D333,401, D333,400, 5,181,923, 5,178,277, 5,174,087, 5,168,619, 5,163,946, 5,156,615, 5,154,283, 5,139,514, 5,133,738, 5,133,723, 5,131,534, 5,131,131, 5,129,511, 5,123,911, 5,121,836, 5,116,358, 5,102,418, 5,099,676, 5,092,455, 5,089,011, 5,089,010, 5,087,263, 5,084,063, 5,084,058, 5,078,730, 5,067,959, 5,059,213, 5,059,212, 5,051,107, 5,046,513, 5,046,350, 5,037,429, 5,024,322, 5,019,093, 5,002,550, 4,984,941, 4,968,315, 4,946,468, 4,932,963, 4,899,743, and 4,898,156;

which are each hereby incorporated by reference in their entirety.

Polymeric drug delivery systems comprising the polymers of the invention can be readily processed into pastes or solvent cast to yield films, coatings, microspheres and fibers with different geometric shapes for design of various medical devices, and may also be processed by compression molding and extrusion. In one embodiment, a polymer or polymers can be coated onto or applied onto a medical device, such as, e.g., by forming the polymer or polymers into a covering. In another embodiment, the polymer or polymers can be formed into a medical device, such as, e.g., an implant.

In one embodiment of the present invention, a polymer containing a functional group or active agent may used to form a covering, such as, e.g., a coating or a sheath, that partially or completely covers and/or surrounds a medical device. Such a covering may cover a portion of the medical device or it may completely cover a medical device. The covering may be divided into separate portions or several smaller coverings may be present on the medical device.

In one embodiment of the invention, a polymer may surround the medical device, or a portion thereof, and may have the form of a coating, a layer, a film, and combinations thereof. The polymer may be in the form of a solid or a semi-solid, such as a gel.

In one embodiment, the polymer may be in the form of a sheath, a wrap, a tube or a cuff covering all or a portion of the medical device.

The polymer may be rigid, semi-rigid, or non-rigid.

In one embodiment, the coating of polymer is from about 100 nm to about 1 cm thick, e.g., from about 1 μm to about 1 mm thick. However, some entirely porous implants may benefit from longer lasting effects enabled by a coating that completely fills the interstices of the device with, in some cases, a thin coating on those surfaces proximal to bone or other tissue upon placement in the body.

In another embodiment, the polymer covers all or a portion of the surface in a thickness of about 0.5 μm to about 2.0 mm.

In one embodiment, the polymer coating is comprised of microspheres. In some cases it may be preferable to have a formulation of microspheres typically but not necessarily less than 10 microns in diameter that can be applied to the surface of a medical device before placement in the body. A sterile liquid may be used to coat the device to adhere such microspheres for minutes to weeks to enable uncoated medical devices to benefit from the same or similar therapeutic benefits as coated devices.

A polymer, compound and/or composition of the invention can be applied or coated onto a medical implant by any means known in the art including, but not limited to, solvent methods such as, for example, dipping and spray-drying, and non-solvent methods such as chemical vapor deposition, extrusion coating, covalently grafting or dipping in molten polymer, compound and/or composition of the invention. The method of preparation may vary depending on the polymer, compound and composition and/or the medical implant. The medical implant can be formed from or coated with one or more layers of the same or different polymer, compound and/or composition of the invention.

In another example, a polymer, compound and/or composition of the invention can be coated onto a medical implant in the shape of a membrane or tube for use in the treatment of injury or damage to the peripheral nervous system or a block of solid or foamed composition containing pathways drilled or otherwise formed to encouraged nerve growth or bone growth. In the above instances, bioerosion of the disc, membrane, tube or block would yield or generate an active agent included within the polymer or composition.

In one embodiment, the polymer is formed into a device. A polymer, compound and/or composition of the invention can be formed into a medical device by any means known in the art including, but not limited to, molding (e.g., compression or blow molding) and extrusion. The medical device can be formed from one or more of the same or different polymer, compound and/or composition of the invention.

A polymer, compound and/or composition of the invention can be formed, that is, physically configured, into various shapes, geometries, structures and configurations including, but not limited to, a film, fiber, rod, coil, corkscrew, hook, cone, pellet, tablet, tube (smooth or fluted), disc, membrane, microparticle, nanoparticle, "biobullet" (i.e., bullet shaped), seed (i.e., bullet shaped or targeted seed), as well as those described in the above identified products, patents and articles, including in some cases forming medical implants that have the same, similar or completely different functional characteristics compared to those functional characteristics of the medical devices described in the above identified products, patents and articles. The above-mentioned shapes, geometries, structures and configurations may contain additional features that will further enhance the desired application or use. For example, a polymer, compound and/or composition of the invention in the form of a rod, coil, or cone may have barbs that spring out upon insertion from a needle or cannula or when warmed to body temperature to reduce movement and/or expulsion.

The shape, geometry, structure or configuration of a device, such as a medical implant, will vary depending upon the use of the device. For example, for treatment of a spinal cord injury or concussion to the brain, a polymer, compound and/or composition of the invention can be formed into a medical implant in the shape of a disc for placement under the dura or dura mater. In another example, a polymer, compound and/or composition of the invention can be formed into a medical implant in the shape of a membrane or tube for use in the treatment of injury or damage to the peripheral nervous system or a block of solid or foamed composition containing pathways drilled or otherwise formed to encourage nerve growth or bone growth. In another example, in the treatment of cancer, a polymer, compound and/or composition of the invention can be formed into a medical implant in the shape of a pellet, microsphere, rod, membrane, disc, bullet, hook, rod or cone, with or without barbs, for insertion in a tumor excision site or for insertion within a tumor. In the above instances, bioerosion of the medical implant would yield or generate an active agent.

The invention also contemplates that the shape, geometry, structure or configuration of a medical implant of the invention can change depending on the mode of delivery or administration and can enhance the therapeutic effect of the medical implant. For example, a medical device of the invention may be in the form of a linear rod when inserted in needles and stored but may become coil-like or form a multiplicity of coils or corkscrew shapes as the medical implant is pushed out of the needle by a trochar. As a result of the change of the shape, geometry, structure or configuration of the medical implant, expulsion from the tumor or tumor excision site by hydraulic pressures or body movements can be prevented and as much mass of active ingredient can be delivered to a small region with as small a diameter needle as possible.

The polymers of the present invention may take the form of a shape memory polymer, which is a stimulus responsive material that can change its shape in response to outside stimuli. Usually this is a temperature-related effect. It depends on the morphology of the material in combination with various processing parameters. Thus, many materials of widely different polymeric chemistry can behave as shape memory. See, e.g., A Lendlein and S Kelch, "Shape Memory Polymers", *Encyclopedia of Polymer Science and Technology*, Ed III (publ J Wiley & Sons, New York, 2003).

First, the material may be programmed by deforming the sample, usually at an elevated transition temperature, and cooling it in the distorted form so that it remains in this temporary state. It will remain there a long time but on reheating to above the programming transition temperature it will revert to its natural undeformed state. Shape memory materials are all elastomers. They have a molecular structure consisting of network linked at certain net points either by physical or chemical cross-linking processes. The elastomer contains two types of polymer blocks whose phases are immiscible and have differing Tm or Tg values.

Shape memory effects are usually recognized by tensile tests in a hot chamber over a range of transitions and seeing how the dimensions alter. The upper limit is the melting point of the highest Tm block. A cyclical regimen will show how well the polymer recovers its original shape.

Examples of shape memory polymers are polyester-urethanes with hard and soft segments. A typical hard switching one is made from butane-1,4-diol and MDI with low Tg but crystalline polycaprolactone blocks. The Tm of the hard 4G-MDI block is the upper temperature limit. Another segmented polyether-urethane is the one from polyTHF and butane diol with MDI. Here, the molecular weight of the soft poly (THF) segment is important—if it is too high the recovery may suffer. Biodegradable shape memory polymers are possible based upon polycaprolactone diols capped with methacrylate groups and copolymerized with a low Tg amorphous vinyl component such as polybutyl acrylate.

Other compositions could include block copolyester-ethers with hard segments such as polylactide, glycolide and soft segments such as polyTHF diol or caprolactone-diol. Polyanhydride links could be incorporated and if a phosgene route was used to make the polyanhydride it could also generate carbamoyl chlorides and urethane links at the same time form suitable amine precursors.

The mode of delivery or administration of a medical device of the invention may vary depending upon the desired application and include those known in the art as well as those set forth herein.

The thickness of the polymer, compound and/or composition as either the medical implant itself or as applied or coated onto a medical implant will vary depending upon one or more factors such as the physical and/or chemical characteristics of the polymer, compound and/or composition, the medical implant and/or the application or use.

For example, a coronary artery stent may be formed from or applied or coated with a polymer, compound and/or composition of the invention to a thickness of about ≦30-50 µm while a vascular stent may be applied or coated with a polymer, compound and/or composition of the invention to a thickness of about ≦100 µm and a drug delivery device may be applied or coated with a polymer, compound and/or composition of the invention to a thickness of about ≦5 mm. In another example, round films/membranes for buccal (sublingual) administration (e.g., placement in lining of cheek, under the tongue) will have diameters of up to about 10 mm (1 cm) and a thickness of about 0.5-2.0 mm.

In the present invention, a covering may be affixed to a medical device in several ways. In one embodiment, the covering may be placed on the outside of the medical device, and through the natural properties of the polymer (i.e., stickiness or adhesiveness), adhere to the device. In one embodiment, the covering may fit snugly, form-fitting, or loosely around the medical device, such that no adhesive is required to affix the covering to the medical device. In another embodiment, a covering of the invention may be affixed to the medical device by means of a biocompatible adhesive, the characteristics of which would be understood by one skilled in the art.

In another embodiment of the invention, a covering may be affixed to a medical device by means of a device external to both the covering and the medical device. For example, the covering may be affixed to the medical device by means of an external clamp, retaining pin, or other such device commonly known in the art. External retaining devices used to affix a covering to a medical device may also be used to retain the shape of the covering. External retaining devices may retain the covering adjacent to the medical device by existing on the outside of the covering, on the inside of the covering (i.e., in between the covering and the medical device), or as a combination both outside and inside of the covering. In yet another embodiment, the covering may be affixed to the medical device by means of a fastener.

Non-limiting examples of materials that can be used to make an external fixing device for a covering of the present invention include surgical steel, nylon, polyethylene, and combinations thereof.

As a non-limiting example of the present invention, a medical device may be covered by a first covering in the form of a polymeric sheath, which is in turn covered by an external retaining device in the form of a semi-rigid or rigid sleeve. Such an external retaining device may be made of metal, plastic, a polymeric substance, or a combination thereof. Such an external retaining device may also be formed of; covered by, or impregnated with a polymer according to the present invention as described herein, or may be covered by or impregnated with an active agent that may be the same as or different than an active agent present in the first therapeutic device according to the present invention. An external retaining device may also contain a polymer that contains a functional group as described above. In another embodiment of the invention, an external retaining device that is formed from a polymer according to the present invention may contain at least one functional group and/or active agent in any of the forms as described above for a first covering.

In one embodiment, a cuff or sleeve comprising a polymer that generates an active agent, such as, e.g., an anti-inflammatory, an anti-infective, an antiseptic agent, or an anti-proliferative agent, is provided. Such a cuff can be made of the polymer entirely or made of an inert substance that is coated with the polymer. The cuff may adjoin or penetrate tissue layers to ensure delivery to the most likely sites of infection. The simplest version of the embodiment would be to coat the surfaces of a suitable device with the polymer and thereby enable a slow release of active agent along its length within the moist and enzyme rich milieu of body tissue.

In preferred embodiments, the medical device is coated with a polymer composition comprising a active agent including, but not limited to, an anti-inflammatory agent, an anti-infective agent, an antiseptic, and an anti-proliferative agent or drug. Polymers and compositions thereof with specific physical properties can be developed by one of skill in the art using the guidance given herein. In some preferred embodiments, a vascular medical device may be further coated with a polymer that has lubricative qualities.

A polymer, compound and/or composition of the invention may be combined or admixed with other ingredients prior to or while being formed into or coated onto a medical device or into a particular coating for a medical device. Examples of suitable additives include, but are not limited to, stabilizers, mechanical stabilizers, plasticizers, hardeners, emulsifiers, other polymers including other biocompatible and biodegradable polymers (e.g., biocompatible and biodegradable polyanhydrides as set forth in U.S. application Ser. No. 09/917,231 and PCT Application No. US/01/23740, biocompatible and biodegradable polyazo compounds as set forth in U.S. application Ser. No. 09/917,595 and PCT Application No. US/01/23748, biocompatible and biodegradable polyesters, polythioesters, and polyamides as set forth in U.S. application Ser. No. 09/917,194 and PCT Application No. US/01/23747, each of which is incorporated by reference in its entirety), radioopaque and/or radioisotopic materials (e.g., boron, iodine, etc.), suppositories, and other diagnostic or therapeutic agents or drugs.

An added ingredient may enhance stability of the polymer, compound and/or composition itself, the medical implant itself and/or may enhance the diagnostic or therapeutic effect and/or may enhance or enable diagnostic activity. For example, if the added ingredient is a diagnostic or therapeutic agent or drug, bioerosion of the polymer would not only generate the active agent but would also release the diagnostic or therapeutic agent. In another example, by adding a radioopaque material, visualization of both the targeted area (e.g., tumor site, tumor) and the medical implant (e.g., catheter) would be enabled during and/or after (e.g., angioplasty, dental applications, joint injections, etc) insertion of the medical implant. In another example, the radioopaque material may also be used to control and/or enhance bioerosion of the medical implant and thereby control and/or enhance generation of the active agent by the generation of heat resulting from neutron capture.

An added ingredient may also enhance the overall mechanical stability of the medical implant (e.g., carbon fibers). The type of additive used would vary and depend so upon the desired property and application.

In one embodiment, a medical device is coated with a therapeutic co-polymer of two or more monomers or more monomers that each independently have different linker groups. In other preferred embodiments, the medical device is coated with a therapeutic polymer composition that is comprised of at least two therapeutic polymers that are mixed after polymerization.

In one embodiment, a medical device having at least one surface is provided, comprising a first polymer on all or a portion of the surface, wherein the polymer is capable of breaking down (e.g., including, but not limited to, hydrolyzing) in the to form one or more active agents, such as a first active agent and a second active agent, under physiologic conditions. The first and second active agents can be the same or different active agents. In one embodiment, the first and second agents can both be incorporated into the backbone of the polymer or attached directly to the backbone, for example, through a linker or spacer molecule, or by direct or indirect chemical linkage to a chemical group attached to the backbone of the polymer; or the second active agent can be dispersed within the polymer matrix of the polymer or appended to the polymer, while the first active agent is incorporated into the backbone of the polymer or attached directly to the backbone, for example, through a linker or spacer molecule, or by direct or indirect chemical linkage to a chemical group attached to the backbone of the polymer; or the first and second active agent can be dispersed within the polymer matrix of the polymer or appended to the polymer. The polymer can also comprise additional active agents, such as a third active agent, a fourth active agent, a fifth active agent, and so on, where the additional active agents are released from the polymer upon hydrolysis, as described herein. For example, the additional active agents can be incorporated into the backbone of the polymer or attached directly to the backbone, for example, through a linker or spacer molecule, or attached to the backbone by direct or indirect chemical linkage to a chemical group attached to the backbone of the polymer; or dispersed within the polymer matrix of the polymer or appended to the polymer as described herein, or otherwise annexed to or associated with the polymer such that the additional active agents dissociate from the polymer upon hydrolysis.

In one embodiment, the medical device having at least one surface is provided, wherein the device comprises more than one polymer on all or a part of the surface, such as, e.g., a first polymer and a second polymer, which can be the same or different. The first polymer is capable of breaking down (e.g., including, but not limited to, hydrolyzing) in the physiologic milieu to form a first active agent, and the second polymer is capable of breaking down (e.g., including, but not limited to, hydrolyzing) in the physiologic milieu to form a second active agent. In one embodiment, the medical device comprises a polymer comprising at least one active agent, wherein the active agent or agents are incorporated into the polymer backbone. The first and second polymers can also comprise one or more additional active agents that are, e.g. incorporated, attached, appended or dispersed within the polymer, as described herein, or otherwise annexed to or associated with the polymer such that the additional active agents dissociate from the polymer upon hydrolysis.

In one embodiment, the medical device has at least one surface, comprising more than one polymer on all or a part of the surface, such as, e.g., a first polymer and a second polymer. The polymers can be the same or different. The first polymer is capable of breaking down (e.g., including, but not limited to, hydrolyzing) in the physiologic milieu to form a first active agent, and the second polymer is capable of breaking down (e.g., including, but not limited to, hydrolyzing) in the physiologic milieu to form a second active agent, and the first and second active agents combine in vivo to form a third active agent. In one embodiment, the medical device comprises a polymer comprising at least one active agent, wherein the active agent or agents are incorporated into the polymer backbone. The first and second polymers can comprise one or more additional active agents that are, e.g., incorporated, attached, appended or dispersed within the polymer, as described herein, or otherwise annexed to or associated with the polymer such that the additional active agents dissociate from the polymer upon hydrolysis.

For example, in one embodiment, the polymer is used as a coating for a device such as a stent that experiences expansion, contraction or torsion in application or use. In the case of vascular stents, the use of such a polymer coating could be used to reduce the incidence of inflammation and resulting hyperproliferation of cells that results in occlusion of the vessel (restenosis). In one embodiment, the linking group is a dicarboxlyic acid hydrocarbon chain with eight carbon atoms.

In one embodiment, the medical device is a stent. The stent can be any suitable stent, such as, e.g., stents described herein. Suitable stents include, for example, coronary vascular stents, peripheral vascular stents, urethral stents, biliary stents, stents used for supporting the lumen of other anatomical tubes, and stents used for other medical and veterinary treatments.

In one embodiment, the device is a stent having at least one surface, comprising a first polymer on all or a portion of the surface, wherein the polymer is capable of breaking down (e.g., including, but not limited to, hydrolyzing) in the to form an active agent under physiological conditions. In one embodiment, the medical device comprises a polymer comprising at least one active agent, wherein the active agent or agents are incorporated into the polymer backbone. The stent can be any stent suitable for use in the present invention. The stent can comprise additional polymers and/or additional active agents, such as, e.g., a second active agent, a third active agent, and so on, where the additional active agents are, e.g., incorporated, attached, appended or dispersed within the polymer, as described herein, or otherwise annexed to or associated with the polymer such that the additional active agents dissociate from the polymer upon hydrolysis. The stent can comprise active agents that combine in vivo to form a new active agent or agents.

In a preferred embodiment an implantable stent is coated with the therapeutic polymer(s). The implantable stent can be made of many materials well known to those in the art, including but not limited to, electropolished 316L stainless steel and other metallic alloys as well as polymeric materials. In preferred embodiments, the polymer coating that exhibits: 1) adequate wettability and adhesiveness to the surface of the stent to be coated, 2) adequate flexibility when crimped onto a balloon catheter, maneuvered into position, and then expanded in position in the body, 3) adequate hardness to avoid premature removal of the coating or portions thereof or pitting or other damage to the coating during implantation of the stent and thereafter (e.g., from handling, flow of blood or other body fluids, or movement of organs or the recipient's body), and 4) appropriate rates of degradation, enabling therapeutic drug levels to be maintained for predictable lengths of time without causing toxicity locally or systemically. For such a device used as a coronary, renal, or biliary stent, the preferred coating, or set of coatings, applied to the stent preferably has a thickness from about 100 nm to about 100 μm, and most preferably has a thickness from about 1 μm to about 30 μm. For stents used in other medical or veterinary applications, coatings or sets of coatings preferably have a thickness less than about 100 μm.

In another embodiment, the therapeutic polymer is used as a coating(s) for an implantable orthopedic device, including hip, knee, shoulder, or elbow replacements, fixation devices, or devices for other orthopedic application. In the case of orthopedic and dental implants such a coating could be used to maintain bone strength or induce bone penetration of the device to stabilize it and/or to reduce pain and inflammation and/or to reduce infections. In one embodiment, the linking group is preferably a dicarboxylic acid hydrocarbon chain with four six, eight or ten carbon atoms.

In one embodiment, the medical devices are orthopedic implants, including hip, knee, and shoulder implants, and internal and external fixation devices and spinal implants. These orthopedic devices can be made of many kinds of materials well known to those in the art, including but not limited to, electropolished 316L stainless steel and other metallic alloys, inorganic ceramics including calcium phosphate and hydroxyapatite, cadaveric bone from humans and other animals, naturally-occurring and synthetic analogs of bone, biodegradable and non-degradable polymers (such as polymers of glycolic acid, lactic acid, and caprolactone, and copolymers thereof), and blends of the above materials. In one embodiment, the orthopedic implants are coated with a therapeutic polymer of the invention such that the polymer coating that exhibits: 1) adequate wettability and adhesiveness to the surfaces of the implant to be coated, such that the coating wets and penetrates into porous spaces percolating to the exposed surfaces of the device, 2) adequate flexibility when handled by the clinician, maneuvered into position, and then interfaced to tissue in the body, 3) adequate hardness to avoid premature removal of the coating or portions thereof or pitting or other damage to the coating during implantation and thereafter (e.g., from handling, flow of blood or other body fluids, or movement of organs or the recipient's body), and 4) appropriate rates of degradation, enabling therapeutic drug levels to be maintained for predictable lengths of time without causing toxicity locally or systemically.

Compositions comprising a polymer can be used to coat orthopedic devices for fixation of bone fractures such as pins or screws, thereby decreasing the local inflammation and bone resorption associated with these devices. Films comprising an aromatic polyanhydride are also believed to be useful as orthopedic devices to enhance the healing process of bone fractures.

In one embodiment, a polymer is coated onto or applied onto or formed into sutures, staples and other related devices. In the case of sutures, staples and other devices such a coating could be used to reduce infections, pain and/or inflammation in the vicinity of the suture or staple.

In one embodiment, fibers useful as suture materials can also be comprised of a polymer. For example, polymer fibers are used frequently in oral surgery to suture cleft palates. Use of a polymer, which degrades to an active agent, such as, e.g., a therapeutic salicylate, would enhance the regeneration of the tissue via the sutures while decreasing the pain and inflammation associated with the surgery via the degradation products.

Films, membranes, pastes, gels, chips and microspheres comprising the polymer can also be used to decrease dental pain and promote healing within a tooth, in the pulp chamber and root canal.

Films or membranes comprising a polymer can also be used in guided bone or tissue regeneration.

In one embodiment, the polymers, compounds and/or compositions of the invention can be formed into micronized particles or microparticles (e.g., microspheres, nanospheres and/or microcapsules). Microparticles of a polymer, compound and/or composition of the invention may be prepared by any means known in the art and may include one or more of the same or different polymer, compound and/or composition of the invention. For example, the microparticles can be prepared-using an oil-in-water emulsion method whereby a polymer of the invention is dissolved in an organic solvent. The polymer solution is then added to a stirring solution of water and PVA (polyvinyl alcohol, which stabilizes the microparticle) resulting in the precipitation of the desired microparticles. Optionally, a homogenizer could be used. The solution is then allowed to settle, the solvent is decanted off the solution and the microparticles are then dried. The microparticles, e.g., microspheres, can be applied to the surface of a medical device before placement in the body. A sterile liquid may be used to coat the device to adhere such microspheres for minutes to weeks to enable uncoated medical devices to benefit from the same or similar therapeutic benefits as coated devices. In one embodiment, the microspheres are typically but not necessarily less than 10 microns in diameter.

In another oil-in-water emulsion method, the polymer solution is added to a solution of water and a surfactant such as PVA, which is stirred rapidly at high shear rates with, for example, a homogenizer or dispersator. After the addition of the polymer solution, the solvent is allowed to evaporate while stirring is continued. The resulting microparticles are recovered by decantation, filtration or centrifugation and dried.

A microparticle of the invention can also be prepared by Southern Research Institute's (Southern Research Institute, Birmingham, Ala.) continuous microencapsulation process as set forth in U.S. Pat. No. 5,407,609, which is incorporated herein by reference in its entirety, and is described in FIG. 1, attached hereto.

According to Southern Research Institute's continuous microencapsulation process described in FIG. 1, proteins, peptides, small molecules, water-soluble drugs, hydrophobic drugs, and drugs encapsulated in lactide/glycolide polymers can be microencapsulated to sizes of about 1-250 μm, preferably <100 μm, more preferably, <10 μm with minimal exposure to polymer solvent, high encapsulation efficiency and good yields. As shown in FIG. 1, a drug, polymer and polymer solvent dispersion is added to a mechanically agitated water/surfactant mixture to form an emulsion of microdroplets, which is then extracted with water to remove solvent and produce hardened microcapsules or microspheres for collection by centrifugation, filtration or the like.

The microparticles of the invention may be formed into various shapes and geometries (e.g., spheres, and regular or irregular spheroid shapes) as well as incorporated into various formulations or compositions (e.g., gelatin capsule, liquid formulation, spray dry formulations, formulations for use with dry powder or aerosol inhalers, compressed tablet, topical gels, topical ointments, topical powder).

As would be understood by one of skill in the art, the desired size of a microparticle of the invention will depend on the desired application and mode of delivery. Modes of administration or delivery of a microparticle of the invention include those set forth herein, including orally, by inhalation, by injection, and topically. The present invention contemplates the administration of a microparticle of the invention that upon degradation or bioerosion yields a smaller particle and/or active agent for the effective treatment of a targeted organ. The present invention also contemplates administration of one or more of the same or different microparticles of the invention having either all the same size or a mixture of two or more different sizes. By varying the size of the microparticle, the rate of bioerosion and/or the rate of generation of active drug and/or the location of active drug generation can be controlled. As a result, timed (e.g., delayed and/or sustained) generation of active drug can be achieved.

For example, treatment of the inflamed wall of the colon (e.g., the treatment of inflammatory bowel disease, infections, and the like) may be achieved by oral administration of a microparticle of the invention containing as the active agent an anti-inflammatory drug. Such a microparticle of about 1-10 μm in size may be administered such that upon reaching the ileum region of the small intestine, the microparticle is about 0.1-1.0 μm in size, and about 0.01-0.1 μm in size upon reaching the colon. See for example, A. Lamprecht et al., *Abstracts/Journal of Controlled Release*, Vol. 72, pp. 235-237 (2001). Once in the intestine, the microparticle can be physically entrapped by the villi and/or microvilli of the intestinal wall and/or by the mucous lining of the intestinal wall, thereby retarding expulsion, and prolonging gastrointestinal residence time and enabling timed sustained generation of the active agent in the proximity of the intestinal wall upon bioerosion of the polymer.

Similarly, about 0.1-100 μm, preferably about 0.1-10 μm, more preferably about 0.1-1 μm, microparticle of the invention may be administered orally such that blood levels of the microparticle enable perfusion of the active agent into the surrounding tissue upon bioerosion. In yet another example, oral administration of a microparticle of the invention of about #0.6 μm, preferably about #0.3 μm, more preferably about 0.1 μm, may be used to deliver an active drug through the intestine and eventually to the liver via the lymph system. See for example, P. Jani et al., *Pharm. Pharmacol.*, Vo. 42, pp. 821-826 (1990); M. Desai et al., *Pharmaceutical Research*. Vol. 13, No. 12, pp. 1838-1845 (1996)

A microparticle of the invention of about 1 to 50 μm may be applied topically or ocularly. Preferably, the microparticle is about 5 to 20 μm.

For subcutaneous or intramuscular injection, about 1-70 μm microparticle of the invention may be used. In one preferred embodiment, about 10-70 μm microparticle of the invention is used for subcutaneous or intramuscular injection. In another preferred embodiment, ≦10 μm microparticle of the invention is used to create a product that feels smooth when applied to human skin. In another preferred embodiment, about 1-3 μm microparticle of the invention is used for skin penetration. However, various microparticle sizes may be used, as exemplified in PowderJect's Smart Particle™ (PowderJect Pharmaceuticals, England, U.K., including those described in U.S. Pat. Nos. 6,328,714, 6,053,889 and 6,013,050) in tissue (e.g., skin, mucosa) penetration applications which appear to rely more on shape and strength of the microparticle rather than size.

A microparticle of the invention may also be used in an inhaled delivery (e.g., direct inhalation at a certain velocity, or by aerosol spray) to the lungs, including deep lungs, or pulmonary region. For example, a microparticle of the invention of about 0.5-10 μm, preferably about 1-5 μm, more preferably about 1-3 μm, even more preferably about 1-2 μm may be formulated into an aerosol. For direct inhalation, about 0.5-6 μm, more preferably about 1-3 μm, microparticle may be used. See for example, ARADIGM's (Aradigm Corporation, Hayward, Calif.) AERx® System as well as those described in U.S. Pat. Nos. 6,263,872, 6,131,570, 6,012,450, 5,957,124, 5,934,272, 5,910,301, 5,735,263, 5,694,919, 5,522,385, 5,509,404, and 5,507,277, and MicroDose's (MicroDose Technologies Inc., Monmouth Junction, N.J.) MicroDose DPI Inhaler as well as those described in U.S. Pat. Nos. 6,152,130, 6,142,146, 6,026,809, and 5,960,609.

A microparticle of the invention of about ≦10 μm may be used for intraarticular injections in the treatment of, for example, arthritis.

A microparticle of the invention of about 0.1-100 μm, preferably about 0.1-10 μm, more preferably about 0.1-1 μm, may be admixed with a suppository (e.g., glycerin suppository).

Figure 3:
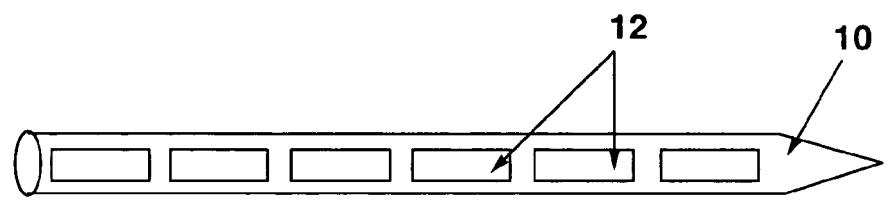
FIG. 3 is an illustration of the placement of pellets, "biobullets," or seeds 10 of the invention inside the hollow cavity or chamber of a bioerodable needle-type carrier.
Figure 4:
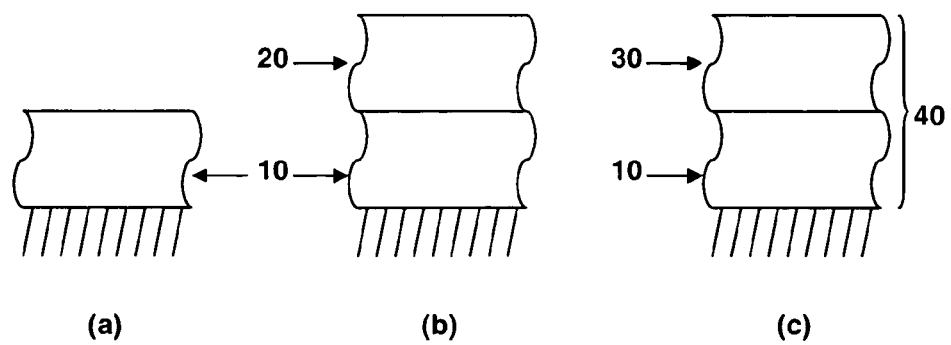
FIG. 4 is an illustration of the possible structuring of layers of coatings, in which one or more of these layers contains a polymerized drug, for implantable medical and veterinary devices. (a) Single layered coating. (b) Multiple layered coating in which the layers may have different compositions and physical properties, including thickness, and in which the top layer(s) is/are not comprising of the polymerized drug and the bottom layer(s) is/are comprised of a polymerized drug. (c) Bilayered coating in which the top and bottom layers are comprised of polymerized drugs with different compositions.

A polymer, compound and/or composition of the invention may also be formed into pellets, "biobullets" (i.e., bullet shaped) or seeds (e.g., bullet-shaped seeds) for inclusion in an implantable and/or injectable bioerodable, hollow carrier 12 (e.g., barrel, bullet, capsule, syringe or needle) as exemplified in FIGS. 2 and 3. Both animal and human applications are contemplated. FIG. 2 illustrates several hollow needle-type carriers 12 for use in the invention. In one embodiment, hollow carriers 12 have a diameter ranging from about 0.5-10 mm.

FIG. 3 illustrates placement of pellets, "biobullets," or seeds 10 of the invention inside the hollow cavity or chamber of a bioerodable needle-type carrier. According to the invention, one or more of the same or different pellet, "biobullet," or seed 10 of the invention may be placed inside the hollow carrier 12 or delivery device. The pellet, "biobullet" or seed 10 may be any size that will enable placement inside the hollow carrier 12.

According to the invention, upon bioerosion of the pellet, "biobullet," or seed 10, an active agent is generated.

The invention also contemplates that the hollow carrier 12 may also be formed from a polymer, compound and/or composition of the invention such that upon bioerosion of the hollow carrier 12, an active agent may be released and/or its contents (e.g., pellets, "biobullets" or seeds of the invention) may be released.

In one preferred embodiment, pellets, "biobullets," or seeds 10 are made from a polymer of the invention containing salicylic acid admixed with follicle stimulating hormone (F.S.H.) and/or lutenizing hormone (L.H.) which are then placed in the hollow cavity or chamber of a bioerodable hollow carrier 12 or as part of a depot formulation (e.g. Lupron Depot®) for a timed release delivery of the hormones up to about 96 hours in order to stimulate ovulation.

According to the invention, a pellet, "biobullet" or seed 10 of the invention and/or one or more hollow carriers 12 containing a pellet, "biobullet," or seed 10 of the invention may be placed in a delivery device (e.g., injector, gas-driven applicator). The delivery device may be further equipped with an axially slideable sleeve (e.g., plunger), protrusions to prevent movement of the delivery device upon application (e.g., chamfered protrusions), and handgrips. Examples of suitable carriers and/or delivery devices include, but are not limited to, those described in U.S. Pat. Nos. 6,001,385, 5,989,214, 5,549,560; WO 96/13300, WO 96/09070, WO 93/23110, and EP 068053, each of which is herein incorporated by reference in its entirety.

For example, U.S. Pat. No. 5,989,214 and WO 96/13300 describe an apparatus for injecting the body of humans or animals with a pharmaceutical preparation, wherein the preparation is arranged in a rigid carrier, wherein the apparatus includes: a chamber into which the carrier can be transported; and a channel connecting onto the chamber for transporting the carrier into the body including fixation means for fixing the end of the channel relative to the skin of the body for injecting in order to prevent a movement of the channel in the direction perpendicularly of the axis of the barrel and where according to one embodiment the fixation means are formed by chamfered protrusions formed on the part adapted for contact with the skin of the body and extending substantially in the direction of the axis of the channel. U.S. Pat. No. 5,549,560, WO 93/23110, and EP 068053 describe a device for injecting humans and animals with a pharmaceutical preparation, wherein the preparation is held in a rigid carrier and the carrier is carried through the skin into the body by means of gas pressure, and wherein during carrying of a rigid carrier into the body by means of gas pressure the device with which the carrier is carried into the body is held against the body. U.S. Pat. No. 5,549,560, WO 93/23110, and EP 068053 also describe a device for injecting animals or humans with a pharmaceutical preparation, wherein a chamber is present in which a carrier containing the pharmaceutical preparation can be placed, a barrel connecting onto this chamber and means for carrying the carrier by means of gas pressure through the barrel into the body for injecting, wherein means are present for blocking the use of the device when it is not pressed against a body. U.S. Pat. No. 6,001,385 and WO 96/09070 describe "bullets" that are at least partly manufactured from substantially fully destructurized starch, particularly implants, suitable as vehicles for introducing active agents into the human or animal body in a transdermal manner.

The present invention also relates to methods of using compositions comprising at least one active agent linked via the polymer backbone in any application wherein delivery of the active agent or agents is desired. Route of delivery is selected in accordance with drug being administered and the condition being treated. In one embodiment, the polymers decompose harmlessly while delivering a selected low molecular weight drug at the site of implantation within a known time period.

Another aspect of the present invention provides a method for site-specific or systemic drug delivery by implanting in the body of a patient in need thereof an implantable drug delivery device containing a therapeutically effective amount of a biologically or pharmaceutically active compound in combination with polymer of the present invention.

In one embodiment, the polymers of the invention can be particularly useful as a controlled release source for an active agent, or as a medium for the localized delivery of an active agent or agents to a selected site. For example, the polymers of the invention can be used for the localized delivery of a therapeutic agent to a selected site within the body of a human patient (i.e. within or near a tumor), where the degradation of the polymer provides localized, controlled, release of the therapeutic agent.

In one embodiment, a method for delivering an active agent to a patient is provided. The method comprises providing a medical device having at least one surface, comprising a first polymer on all or a portion of the surface, wherein the polymer is capable of breaking down (e.g., including, but not limited to, hydrolyzing) in the physiologic milieu to form a first active agent, and administering the device to the patient such that the first active agent is delivered to the patient. The device can comprise additional polymers and/or additional active agents, such as, e.g., a second active agent, a third active agent, and so on, where the additional active agents are, e.g., incorporated, attached, appended or dispersed within the polymer, as described herein, or otherwise annexed to or associated with the polymer such that the additional active agents dissociate from the polymer upon hydrolysis and are delivered to the patient. The device can comprise active agents that combine in vivo to form a new active agent or agents that is delivered to the patient. The active agent or agents can be delivered to any suitable site or sites in a patient, such as, for example, the circulatory system (e.g., a vein or an artery), a tissue, an organ (e.g., lung, liver, spleen, kidneys, brain, eye, heart, muscle, and the like), a bone, cartilage, connective tissue, epithelium, endothelium, nerves, a tumor, or any other site suitable for delivery of an active agent or agents.

Suitable sites will typically be sites that are or will be in need of treatment with an active agent or agents, such as, e.g., an injured site or a site that may become injured, for example, due to a disease, a medical condition, or during or after a medical procedure, such as, e.g., a balloon angioplasty and/or implantation of a medical device.

In one embodiment, a method for delivering an active agent to an interior surface of a vein or artery is provided. The method comprises providing a medical device having at least one surface, comprising a first polymer on all or a portion of the surface, wherein the polymer is capable of breaking down (e.g., including, but not limited to, hydrolyzing) in the physiologic milieu to form a first active agent, and positioning the medical device at or near the interior surface of the vein or artery such that the first active agent dissociates upon hydrolysis and is delivered to the interior surface of the vein or artery. The device can comprise additional polymers and/or additional active agents, such as, e.g., a second active agent, a third active agent, and so on, where the additional active agents are, e.g., incorporated, attached, appended or dispersed within the polymer, as described herein, or otherwise annexed to or associated with the polymer such that the additional active agents dissociate from the polymer upon hydrolysis and are delivered to the interior surface of the vein or artery. The device can comprise active agents that combine in vivo to form a new active agent or agents that are delivered to the interior surface of the vein or artery.

In one embodiment, the method prevents, reduces, and/or inhibits the development of restenosis in the blood vessel. Restenosis can be defined as, for example, the narrowing of the vessel to about 80%, about 70%, about 60%, about 50%, about 40%, about 30%, about 20%, about 10% or less, of the diameter of the vessel after removal of any blockages from the vessel and the placement of the device into the vessel.

The compositions, devices and methods of the present invention are useful for treating a wide array of diseases and conditions, including, for example, those set forth below and/or otherwise described herein.

In cardiology, such compositions, devices and methods can be used, for example, to develop coatings for stents, sutures and pacemakers, or other devices used in cardiology as otherwise referenced herein.

In ophthalmology, such compositions, devices and methods can be used, e.g., to develop a lens replacement for cataracts with a translucent polymer; for a direct injection of microspheres into the eye to provide a depot of anti-inflammatory therapy; or for the treatment of glaucoma.

In otolaryngology, such compositions, devices and methods can be used, e.g., to develop antibiotics for otic administration (e.g., amoxicillin microspheres); for reconstructive surgery (e.g., bone restructuring); as a treatment for tuberomandibular joint (TMJ) pain by direct injection; as a treatment of chronic sinusitis by injection of microspheres; or for compositions delivered via inhalers (e.g., dry powders or admixed with non-CFC propellants).

In bone and orthopedic applications, such compositions, devices and methods can be used, e.g., to develop orthopedic injections of inventive compositions; for bone implants; for the prevention of bone erosion; for wound healing by inhibiting osteoclasts and preventing spurious bone growth; as bone putty; for spinal cage bone pins (e.g., mixture of inventive polymers with hydroxyappetite fillers and other fillers); as a coating for orthopedic implants to decrease pain, inflammation, bone erosion and infections; as combinations of poly-NSAIDS plus poly-antibiotics to treat osteomyelitis or other bone infections by direct injection into the marrow; for the treatment of bone cancer with antiproliferatives; for the treatment of trauma; as prosthetic devices and coatings therefore; or other devices used in bone and orthopedic applications as otherwise referenced herein.

In neurology, such compositions, devices and methods can be used, e.g., to develop microspheres injections for injection into the cerebral spinal fluid In oncology, such compositions, devices and methods can be used, e.g., to treat any suitable cancer, such as, e.g., liver cancer, ovarian cancer, prostate cancer, and breast cancer; for delivery to any surgical site where cancer is removed and there exists a concern that not all cancer cells were removed; or to develop compositions of poly-antiproliferatives sprinkled into the peritoneum, which slowly erode and circulate through the lymphatics where the primary metastases congregate.

In dentistry, such compositions, devices and methods can be used, e.g., to develop alveolar bridges, tooth implants, patches for treating long-term pain, microspheres to treat or prevent dry socket, chips and wafers, chewing gum, dental floss and microspheres coatings on toothbrushes; and for the prevention of bone erosion.

In gastroenterology, such compositions, devices and methods can be used, e.g., for oral administration of inventive polymers with antacids to treat ulcers, heartburn and other acid-related diseases; for the treatment of irritable bowel syndrome with inventive compositions having a particular particle size; or for use of the compositions (e.g., a poly-NSAID) to prevent or treat inflammation at a colostomy sinus.

In obstetrics and gynecology, such compositions, devices and methods can be used, e.g., for the prevention of toxic shock syndrome by using the inventive compositions in fibers of tampons; for the treatment of yeast infections; for the treatment of chlamydia infections; as suppositories; as a cervical ring to treat or prevent cramps or premenstrual syndrome; and as surgical meshes and coatings to treat hernias.

Surgical applications of such compositions, devices and methods include, e.g., as coatings for bladder catheters; as coatings for indwelling catheters; as coatings for biosensors, particularly the leads, to prevent scarring and granulomas and to avoid signal interference and increase battery life; as compositions as surgical adhesives; as microspheres sprinkled into any surgical field to prevent adhesions; and for subdural barriers or films to prevent swelling and inflammation.

The compositions, devices and methods can also be used in wound healing applications, including, e.g., as sutures, surgical meshes, bandages, and other mechanical wound closure products or coatings thereof. The compositions can be also be in the form of microparticles (e.g., microspheres, microplatelets or other microstructures) as a powder or pellets to be applied locally (e.g., sprinkling) to the affected area.

In dermatology, such compositions, devices and methods can be used, e.g., to develop sunscreens; insect repellants (admixed or polymerized compounds, e.g., DEET; Merck IR 3535; citronella); bandages; as microspheres in patches to deliver systemically active drugs; for the treatment of psoriasis (poly-methotrexate optionally combined with poly-NSAID); for the treatment of seborrhea; and for the treatment of dandruff.

Polymers of the present invention can also be incorporated into oral formulations and into products such as skin moisturizers, cleansers, pads, plasters, lotions, creams, gels, ointments, solutions, shampoos, tanning products and lipsticks for topical application.

Formulations

The polymers of the invention can be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical, ocular, pulmonary or subcutaneous routes. For some routes of administration, the polymer can conveniently be formulated as micronized particles.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered subcutaneously, intramuscularly, intravenously, intraspinally, intracranially intraspinal, intracranial, or intraperitoneally by infusion or injection. Solutions of the polymer can be prepared with a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present polymers can be applied in pure form. However, it will generally be desirable to administer them as compositions or formulations, in combination with a dermatologically acceptable carrier, which may be a solid or a liquid. Examples of useful dermatological compositions which can be used to deliver the polymers of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful solid carriers include finely divided solids such as talc, clay, microcrystalline cellulose, silica, alumina and the like. Useful liquid carriers include alcohols or glycols or alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Doses

Useful doses of the polymers can be determined using techniques known in the art, such as, e.g., by comparing their in vitro activity with the in vivo activity of the therapeutic agent in animal models. Methods for the extrapolation of effective doses in mice, and other animals, to humans are known to the art; for example, see U.S. Pat. No. 4,938,949. Additionally, useful doses can be determined by measuring the rate of hydrolysis or enzymatic degradation for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician, and is easily determinable by one of ordinary skill in the art.

The quantity of polymeric drug to be administered to a host that is effective for the selected use can be readily determined by those of ordinary skill in the art without undue experimentation. The quantity essentially corresponds stoichiometrically to the amount of drug which is known to produce an effective treatment for the selected use The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The total amount of active agent released will vary depending on the particular active agent and treatment protocol involved, as is easily determined by one ordinarily skilled in the art. The amount of active agent released will typically be from about 0.1 µg to about 10 g, preferably from about 1 µg to about 100 mg, more preferably from about 10 µg to about 10 mg, more preferably from about 50 µg to about 1 mg.

Preferably, the polymers are formulated to provide local release of an effective amount of an active agent or agent over a period of at least about 2, about 5, about 10, about 20, or about 40 days. The compositions can also preferably be formulated to provide local release of an effective amount of the agent over a period of up to about 3 months, about 6 months, about 1 year, or about 2 years.

The active agent can be released from the polymer at any rate suitable for appropriate delivery of the active agent to the patient. In one embodiment, the active agent is released at a rate from about 0.01 µg per day to about 100 mg per day, from about 1 µg per day to about 10 mg per day, or from about 10 µg per day to about 1 mg per day.

It will be appreciated that the greater the potency of the coating, the better with regard to minimizing the space required for the administered product, the potential cost of the product, the ease of manufacturing the product, and the potential impact on other desired properties of the medical implant.

The polymers of the present invention can be characterized by techniques known in the art. Degradation and drug release profiles of the polymer drug delivery systems of the present invention can also be determined routinely.

The range of therapeutically effective dosages, that is, the dosage levels necessary to achieve the desired result, of a microparticle of the invention will be influenced by the route of administration, the therapeutic objectives, and the condition of the patient. As such, a polymer of the invention may be administered as a single daily dose, several times daily, every other day, weekly, etc. depending on the dosage requirements. Individual determinations will need to be made to identify the optimal dosage required.

Co-Polymers and Blends of Polymers

The therapeutic polymers and compositions thereof used in some applications, such as for coating implantable medical and veterinary devices, including stents and orthopedic implants, may require greater elasticity or flexibility while retaining sufficient hardness and adhesiveness to remain intact on the device as the device is handled or otherwise manipulated by the clinician or surgeon or within the body of the patient, such as, e.g., when the device interacts (e.g., mechanically and chemically) with the surrounding tissue or fluid or luminal wall, or, in the case of a stent, with the intraluminal wall of a vessel in which the vessel and stent experience pulsatile motion due to the pulsatile nature of blood flow and the contraction of the vessel wall by the associated smooth muscle. To provide desired physical properties, including mechanical strength, modulus, and elongation without failure, it is possible to create coating comprised of a co-polymer of two or more monomers used to create the two or more polymers that have physical properties and other performance characteristics bracketing those properties and characteristics desired.

In one embodiment, copolymers of similarly sized or "sequential" linkers, i.e. adipic acid (6 carbon) and suberic acid (8 carbons) are made in order to "fine tune" the physical properties of the polymer to a state between the two available linkers. However, "non-sequential" co-polymers are also contemplated, for example a co-polymer containing adipic acid (6 C) and sebacic acid (10 C) linkers. Additionally, co-polymers comprising three or more linker group moieties are also contemplated.

In one embodiment, the co-polymer is formed from the monomers salicylic acid and adipic acid, and salicylic acid and suberic acid, about 50% or more mole percent of the co-polymer is the monomer salicylic acid and adipic acid.

Alternatively or in combination with one or more of the co-polymers described above, it is possible to create a physical blend of two or more polymers or co-polymers in which the individual polymers or co-polymers blended each have a set of physical properties and performance characteristics that meet or exceed requirements for a coating for the specified implantable medical or veterinary device and its application but may have one or more physical properties and performance characteristics that are insufficient for that device and its application, such that the combination of properties and characteristics provided by the blend meet or exceed the required properties and characteristics needed for the device and its application.

These blends may be of polymers that are miscible or inmiscible in each other. For example, it is possible to make a co-polymer or blend of polymers or co-polymers in which one monomer in the co-polymer or one polymer or co-polymer in the blend has a hardness that exceeds the requirements for the coating for the device and its application but a flexibility insufficient and another monomer in the co-polymer or another polymer or co-polymer in the blend that has a flexibility sufficient but a hardness insufficient for the device and its application. The physical properties and performance characteristics of the copolymer can be fine tuned further by selecting the percentage of each monomer in the copolymer or the percentage of each polymer or co-polymer in the blend towards the combination of monomers or polymers or co-polymers that produce a coating that has physical properties and performance characteristics closer to the desired set.

In an exemplary embodiment, a polymer comprising salicylic acid or a derivative of salicylic acid, such as diflunisal, and linkers of dicarboxylic acids in which the pair of carboxylic acids within the diacid are separated by a linear alkyl chain, is coated on a stent or other device experiencing expansion, contraction, or torsion in application or use. A coating comprising a polymer in which the alkyl chain comprises six atoms of carbon (known as adipic acid) may crack or craze upon change in dimensions (e.g., expansion for a stent), whereas a coating comprising a polymer in which the alkyl chain comprises eight atoms of carbon (known as suberic acid) may be excessively tacky or otherwise adhere to the materials used in handling and implantation (e.g., the balloon used for expansion of the stent). For such applications, in the absence of an admixed drug or other additive that alters the physical properties and performance characteristics in a predictable and repeatable manner, a suitable coating can comprise, for example, a polymer of salicylic acid and suberic acid or a copolymer of monomers of salicylic; acid and dicarboxylic acid or a physical blend of polymers or co-polymers of salicylic acid and dicarboxylic acid that approximate the tradeoffs in physical properties and performance characteristics, including hardness, tackiness, and flexibility, of polymers created with a linker of suberic acid.

In another exemplary embodiment, a polymer comprising salicylic acid or a derivative of salicylic acid, such as diflunisal, and linkers of dicarboxylic acids with linear alkyl chains, and is coated on an orthopedic implant for use as a hip, knee, shoulder, elbow replacement, a fixation device, or another orthopedic application. In the absence of an admixed drug or other additive that alters the physical properties and performance characteristics in a predictable and repeatable manner, a suitable coating can comprise, e.g., a polymer of salicylic acid and a dicarboxylic acid linker with four, six, eight or ten carbon atoms in the linear alkyl chain (known as succinic and adipic acids, respectively) or a copolymer of monomers of salicylic acid and dicarboxylic acid or a physical blend of polymers or co-polymers of salicylic acid and dicarboxylic acid that approximate the tradeoffs in physical properties and performance characteristics, including hardness, tackiness, and flexibility, of polymers created with a linker of succinic or adipic acids.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e. not in the backbone of the polymer) with bonds that hydrolyze to release the second therapeutic agent under physiological conditions; 3) the polymer of the invention can incorporate two therapeutic agents into the polymer backbone; or 4) two polymers of the invention, each with a different therapeutic agent can be administered together (or within a short period of time). Of course, more than one therapeutic agent can be used in each of the above cases.

Thus, the invention also provides a medical device comprising a polymer that hydrolyzes to form a first active agent and a second active agent that is dispersed within, the polymer matrix of a polymer of the invention. The invention also provides a medical device comprising a polymer that hydrolyzes to form a first active agent having a second active agent appended to the polymer (e.g. with bonds that will hydrolyze to release the second therapeutic agent under physiological conditions).

The polymers of the invention can also be administered in combination with other active agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

Suitable drug combinations for incorporation into the polymers or the compositions of the invention include for example, a first active agent that is classified as a nonsteroidal anti-inflammatory drug (NSAID), such as, e.g., salicylic acid or diflunisal, combined with a second active agent classified as an anti-cancer and/or anti-neoplastic agent (e.g., paclitaxel or methotrexate) or as an immunosuppressive (e.g., rapamycin).

Preferred drug combinations for incorporation into the polymers or the compositions of the invention include the following: amoxicillin/clavulanic acid; and imipenem cilastatin.

Admixing Component Materials

The formation of a composite of two or more materials results in a new material that can have physical properties and performance characteristics substantially different from any of the individual component materials comprising the new material. In the case of polymers, these altered physical properties can include an increase or decrease in glass transition temperature, tensile or shear moduli, effective viscosity, yield strength and elongation, elongation at failure, tackiness or adhesiveness, hardness, color, rate of thermal or biological breakdown, surface texture, or wettability by water or other fluid. For example, the mechanical properties of bone, a composite of inorganic calcium phosphates and organic collagen molecules, are distinct from the mechanical properties of either calcium phosphates or collagen alone.

In one embodiment, a polymer of the invention is admixed with an anti-proliferative agent, such sirolimus, everolimus or paclitaxel, or other material or agent, such as specific RNA and DNA sequences and their chemical mimics or derivatives, calcium phosphate, hydroxyapatite, an antibiotic, an immunosuppressive agent, or another agent. These added compounds can alter the mechanical properties of the polymer (e.g., by modifying the degradation rate, the tensile modulus, the yield strength, and/of the elongation at which failure of the material occurs). Coatings made from the therapeutic polymer will also exhibit the altered mechanical properties.

The extent to which the admixture of one or more drugs or other therapeutic agents changes the physical properties and performance characteristics of the coating will depend on the amount or concentration of each of the drugs or agents, with a trend that increasing the amount or concentration of a drug or agent is expected to increase, if at any changes occurs at all, one or more of these properties or characteristics. In practice, coatings with 20 or more percent admixed drug or agent can be achieved by blending the admixed compound into the polymer prior to coating or by first applying the polymer as a coating and then absorbing the compound to be admixed into the coating by exposing the coating to a solution with the compound.

In an exemplary embodiment, a coating of a polymer with an admixed drug, applied on an expandable stent, comprises a dicarboxylic acid with more than six carbon atoms in the linear alkyl chain, or a co-polymer or physical blend of polymers or co-polymers that approximate the physical properties and performance characteristics of the polymer with a linker with more than six carbon atoms in the linear alkyl chain, such that these polymers approximate the physical properties and performance characteristics of a polymer with a linker of suberic acid (8C).

In another exemplary embodiment, a coating of a polymer with an admixed drug, applied on an orthopedic implant, comprises a dicarboxylic acid with more than four carbon atoms in the linear alkyl chain, or a co-polymer or physical blend of polymers or co-polymers that approximate the physical properties and performance characteristics of the polymer with a linker with more than four carbon atoms in the linear alkyl chain, such these polymers approximate the physical properties and performance characteristics of a polymer with a linker of succinic (4C) or adipic (6C) acid.

In some embodiments, compositions comprising polymers may have optimum physical and chemical properties derived by blending compounds into the polymer that decrease or increase the rate of penetration of water and/or enzymes into the polymer matrix and, thereby, decrease or increase the rate of breakdown of the polymer, thereby modulating the duration of generation of drug from the components of the polymer backbone and/or the release of admixed drug or agent. In addition, qualities such as shelf life (e.g., stability in the presence of elevated temperatures, humidities, or electromagnetic radiation), rates of depolymerization (e.g., by hydrolysis or proteolytic activity) or oxidation, and rates of hydration can be varied by adding antioxidants or lipophilic molecules to reduce oxidation or hydration of the polymer blend, respectively. In some cases, the qualities of the admixed drug or agent may influence the physical or chemical properties, including shelf life, tolerance to sterilization methods, or degradation rate of the final product. For example, the admixed drug or agent may extend the shelf life, increase the types and/or dosages of sterilant that can be applied without changing other properties of the material, or decrease or increase the degradation rate of the final product.

Layering Coatings of Polymers

The polymers of the invention can be layered onto devices with other polymers of the invention, or other polymers in general, to form coatings with desirable properties. The therapeutic polymers can be structured and/or layered as a coating with one or more additional coatings that may or may not be biodegradable (i.e., degradable by hydrolysis or enzymatic/proteolytic activity when placed in contact or exposed to body tissues or fluids). The additional coatings may contain the same polymerized active compound, a different polymerized active compound, no polymerized active compound, or one or more admixed drugs or agents. This structuring may be in the form of a layer of a coating on the exposed surface of the coating of the therapeutic polymer such that this coating lies between the polymerized active compound, and the body tissues and/or fluids following implantation. Alternatively, a second polymer or smaller molecular-weight species may be physically blended with the therapeutic polymer, and a series of layered coatings of therapeutic polymer compositions that have different chemical compositions and/or physical (e.g., mechanical) properties. Several, but not all, of the possible structuring of layers are depicted in FIG. 1.

In some embodiments of the invention, layering permits refinement of the rate or duration of generation, release, or elution of active agents over time, including the possibility of having one or more outer coatings with higher or lower permeability to modulate the breakdown of one or more inner coatings and thereby result in a more constant release of active agent over particular periods of time. In embodiments in which one or more outer coatings are biodegradable, the breakdown and resulting increase in permeability of these outer coatings can compensate for a rate of generation (by breakdown of the polymer) or release of an active agent that varies with time by increasing the rate of permeation of the active agent from the inner coating through the outer coatings. Such embodiments can be used to create a rate of delivery of drug from the coatings on the device that vary less temporally (i.e., are more closely more zero-order) and that can be adjusted based on the preferred shape and, therefore, surface area of the device and changes in surface area that occur as the coatings erode.

Multiple layers of polymers generating, eluting, or releasing inert and active products upon breakdown may be designed for specific applications, including those applications in which one class or member of a class of agents is to be generated, eluted, or released from the coating before a second class or a second member of the first class of agents is generated, eluted, or released from the coating. An example of such a layered coating, as depicted in FIG. 1c, is a coating in which an anti-inflammatory agent (e.g., from the class of NSAIDs) is generated, eluted, or released from the coating 30 substantially before an anti-proliferative agent is generated, eluted, or released from the coating 10. Such types of layered coatings 40 enable tuning of the rate of generation, elution, or release of drugs from the coating over time, such that a near constant, gradually increasing, gradually decreasing, or a combination thereof amount of drug most appropriate for treatment of tissues in the vicinity of the device can be delivered to these tissues.

In some embodiments of the invention, one or more inert polymer coatings may applied as one or more top coats on one or more coatings of one or more polymers, including coatings with admixed drugs or other agents. Top coating can be applied to increase the hardness and/or or lubricity of the coating and, thereby, the device during insertion or use. Additionally, top coating can be applied to vary (e.g., increase or decrease) the rate of hydration or enzyme penetration and, thereby, vary (e.g., increase or decrease) the rate of generation of the drug from the polymer backbone or release of an admixed drug or other agent from the underlying coating. Finally, top coatings can be applied to increase the shelf life of the final product by limiting the penetration of water or oxygen into the underlying therapeutic polymer coating. In preferred embodiments, the top coatings will be biodegradable.

In one embodiment of the invention, the preferred rate of drug delivery may be achieved by using multiple layers of polymer. In some cases different concentrations of the same admixed drug may be used in each layer or different copolymers having different rates of drug generation and/or polymers with different breakdown rates for release of admixed drugs or agents may be used in each layer, thereby achieving a predictable and repeatable timing of delivery of one or more bioactive agents. Such layering effects can be enhanced by a combination of layers of inert polymer and/or layers with inert polymer with admixed drug or agents and/or layers with therapeutic polymers and admixed drugs or agents and/or layers with only therapeutic polymers. In an exemplary embodiment, an outer coating that would provide an initially high dose of anti-inflammatory agent that is followed by the release or generation of an anti-proliferative agent from underlying layers.

In one embodiment, a medical device is coated with more than one layer of polymer, where at least one layer is the therapeutic polymer of the invention. The polymers include but are not limited to "inert" polymers that do not breakdown or breakdown into non-therapeutic agents. One or more coatings or layers of an inert or therapeutic polymers can be used to advantage with the therapeutic polymers of the invention to regulate the release of active agents released from or generated by therapeutic polymer underlying the coating or layer of polymer. In more preferred embodiments, the active agent(s) is predictably and repeated released over time. For example, the active agent may be released from the set of coatings at a steadily increasing or decreasing rate, or at a nearly constant rate over time. In other more preferred embodiments, the outer layer(s) of polymer slow or prevent the penetration of water and/or enzymes to the inner layer(s) of therapeutic polymer. These embodiments are useful to lengthen the shelf-life of the medical device, and/or to regulate the release or generation of the active agent in underlying layers. In most preferred embodiments, the layer(s) of therapeutic polymer on the medical device are further coated with a layer of polymer which is polylactic acid, a polymerized form of amino acids, a polymerized form of fatty acid metabolites, and derivatives and/or combinations of any of these.

FIGS. 16-27 provide further illustrations of the characteristics of the polymers of the present invention.

EXAMPLES

Figure 8A:
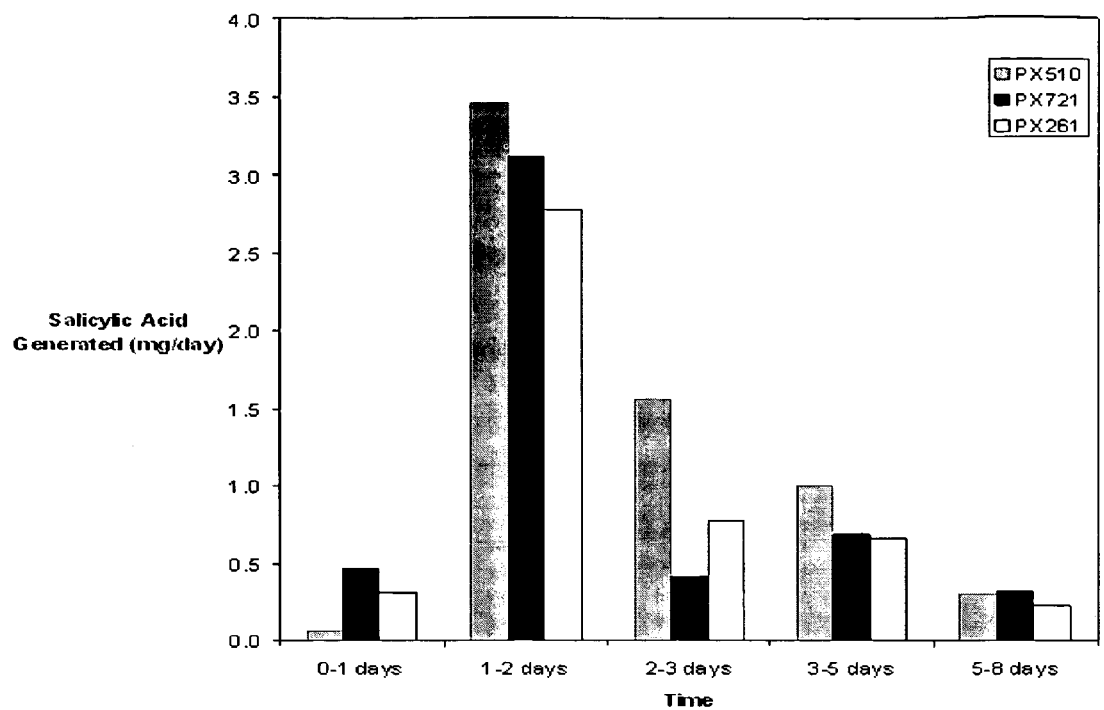
FIG. 8A is a graph showing the rate of generation of salicylic acid by the bioerosion of a coating of polymerized salicylic acid.
Figure 8B:
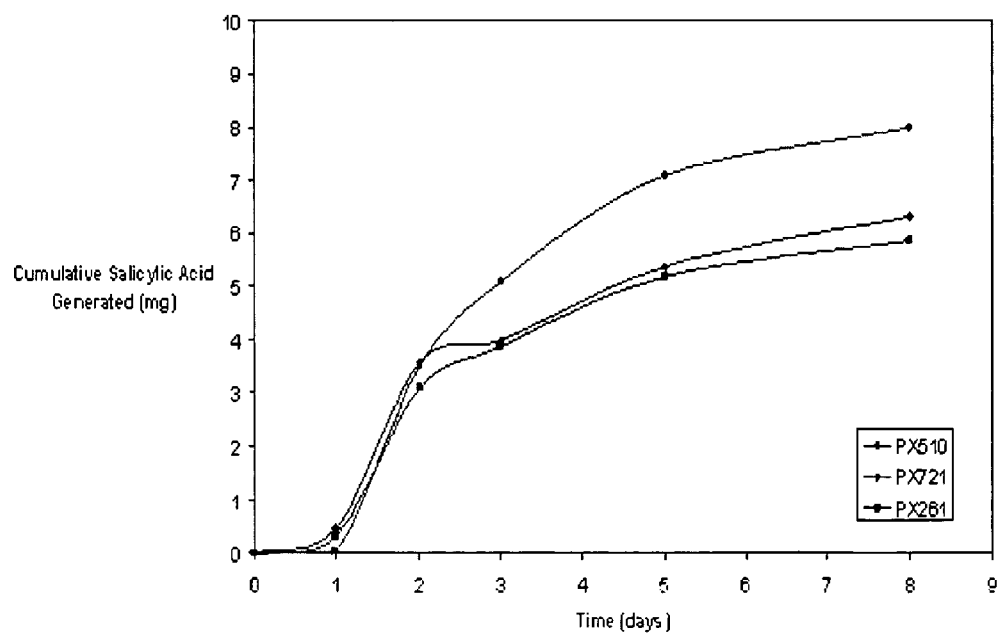
FIG. 8B is a graph showing the cumulative mass of salicylic acid generated by the bioerosion of a coating of polymerized salicylic acid.

Examples 1-4 teach the making of co-polymers of salicylic acid and dicarboxylic acid linker groups of various lengths, and illustrate some of the altered physical properties obtainable with compositions comprising therapeutic co-polymer(s). Example 1 makes and compares polymers comprising salicylic acid with one linker moiety (the homo-linker polymer) with a copolymer composed of a 50:50 mole percent composition of two monomer, salicylic acid and adipic acid and salicylic acid and suberic acid. FIGS. 8A and 8B shows the rate that salicylic acid is released from the copolymer is intermediate between the two homo-linker polymers.

Example 1

Figure 9A:
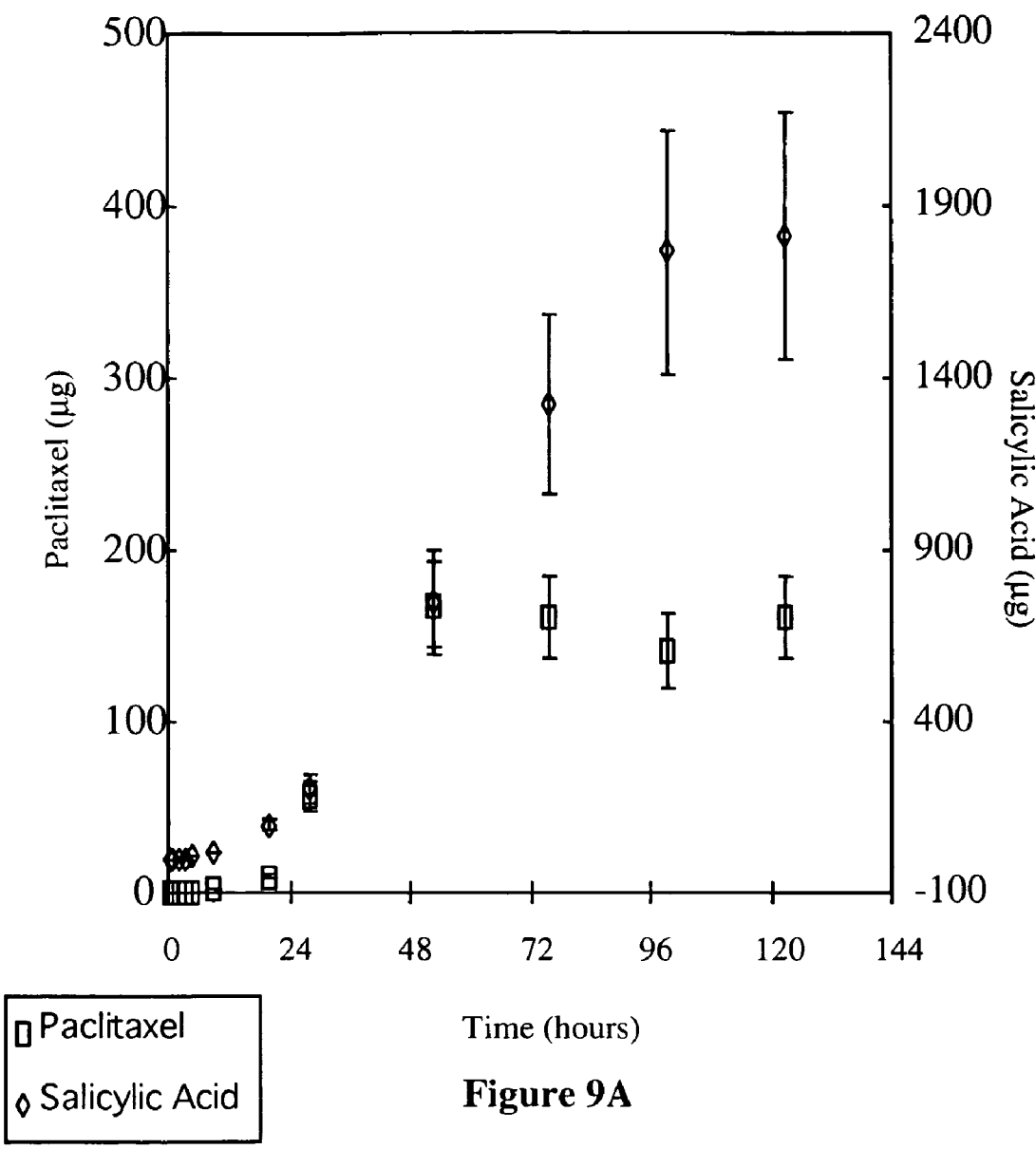
FIG. 9A is a graph showing the cumulative masses in a bathing solution of PBS resulting from simultaneous generation of salicylic acid by the bioerosion of a coating of polymerized salicylic acid (PX510) and release of paclitaxel from that coating.
Figure 9B:
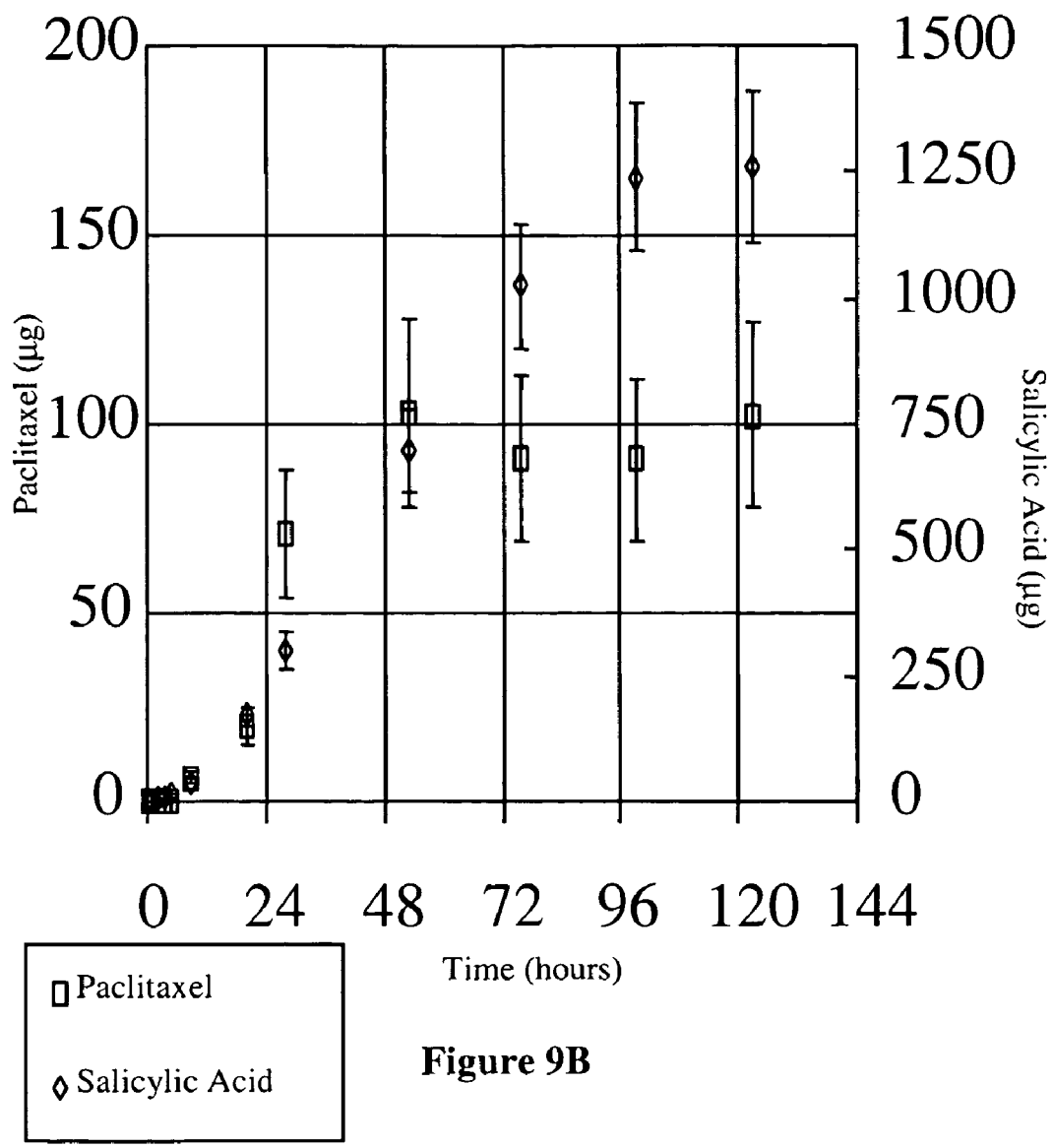
FIG. 9B is a graph showing the cumulative masses in a bathing solution of PBS resulting from simultaneous generation of salicylic acid by the bioerosion of a coating of polymerized salicylic acid (PX749) and release of paclitaxel from that coating.

Data obtained for 316L stainless steel coupons with a 30 mm×20 mm×~5 µm thick coating of therapeutic polymer composed of salicylic acid and adipic acid (PX510), suberic acid (PX261), sebacic acid (PX749), or dodecandoic acid (PX125), a copolymer formed by polymerizing a 50:50 mole percent mixture of monomers composed of salicylic acid and adipic and suberic acids, respectively (PX721), or PX510 or PX749 admixed with 14% of the anti-proliferative agent paclitaxel. FIGS. 5 and 6 present data for hardness and flexibility, respectively, obtained using accepted ASTM methods. FIG. 7 presents data for adhesion between the polymerized drugs and the coupons obtained using an accepted ASTM method. FIG. 8 presents data for the generation of salicylic acid into an incubating solution of pH 7.4 phosphate buffered saline (PBS) maintained at 37° C., expressed as either the mass of salicylic acid generated per day (FIG. 8*a*) or the cumulative mass of salicylic acid generated (FIG. 8*b*). FIG. 9 presents data for the simultaneous generation of salicylic acid and release of paclitaxel into an incubating solution of pH 7.4 phosphate buffered saline (PBS) maintained at 37° C., expressed as the cumulative mass of salicylic acid generated, for PX510 (FIG. 9*a*) and PX749 (FIG. 9*b*). These data demonstrate that the hardness of a coating of polymerized salicylic acid and a dicarboxylic acid linker can be varied by varying the number of carbon atoms in the dicarboxylic acid linker, that the rate of generation of salicylic acid by bioerosion is substantially independent of the number of carbon atoms for the range of linkers examined, and that simultaneous generation of salicylic acid and release of paclitaxel can be achieved by admixing paclitaxel into a polymerized drug of salicylic acid.

Example 2

Data obtained for therapeutic polymer composed of salicylic acid and adipic acid (PX510), suberic acid (PX261), sebacic acid (PX749), or a copolymer formed by polymerizing a 50:50 mole percent mixture of monomers composed of salicylic acid and adipic and suberic acids, respectively (PX721). FIG. 10 presents data for the thermomechanical properties, including glass transition temperature ($T_g$), tensile modulus, yield strength, and ultimate elongation (also known as the elongation at failure), as measured using differential scanning calorimetry (DSC) and dynamic mechanical analysis (DMA). Data for DMA was obtained using a Perkin Elmer DMA 7e for pressed films with dimensions of approximately 1 cm length×3 mm width×0.8 mm thickness. These data demonstrate that the thermomechanical properties of a polymerized drug can be varied by varying the number of atoms of carbon in the dicarboxylic acid linker.

Example 3

Data obtained for wires coated with the therapeutic polymer PX510 composed of salicylic acid and adipic acid admixed with 1.8% of the immunosuppresive agent sirolimus. FIG. 11 presents data for the simultaneous generation of salicylic acid and release of sirolimus into an incubating solution of pH 7.4 PBS, containing 25% ethanol and maintained at 28° C., expressed as the cumulative mass of salicylic acid generated. These data demonstrate that simultaneous generation of salicylic acid and release of sirolimus can be achieved by admixing sirolimus into a polymerized drug of salicylic acid.

Example 4

Figure 13A:
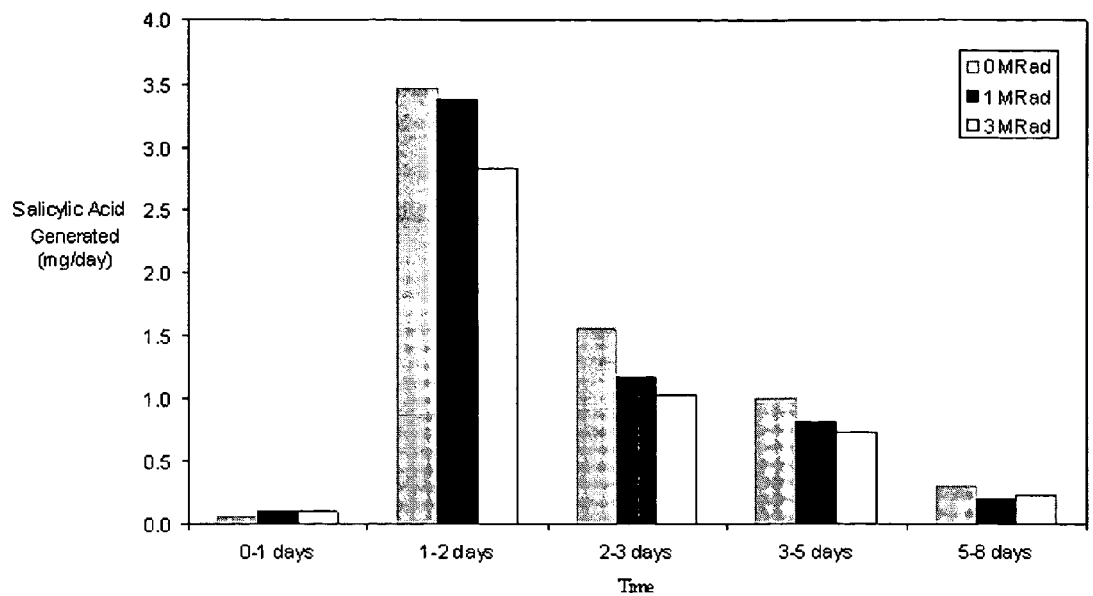
FIG. 13A is a graph showing the rate of generation of salicylic acid by the bioerosion of a coating of untreated and E beam-treated polymerized salicylic acid.
Figure 13B:
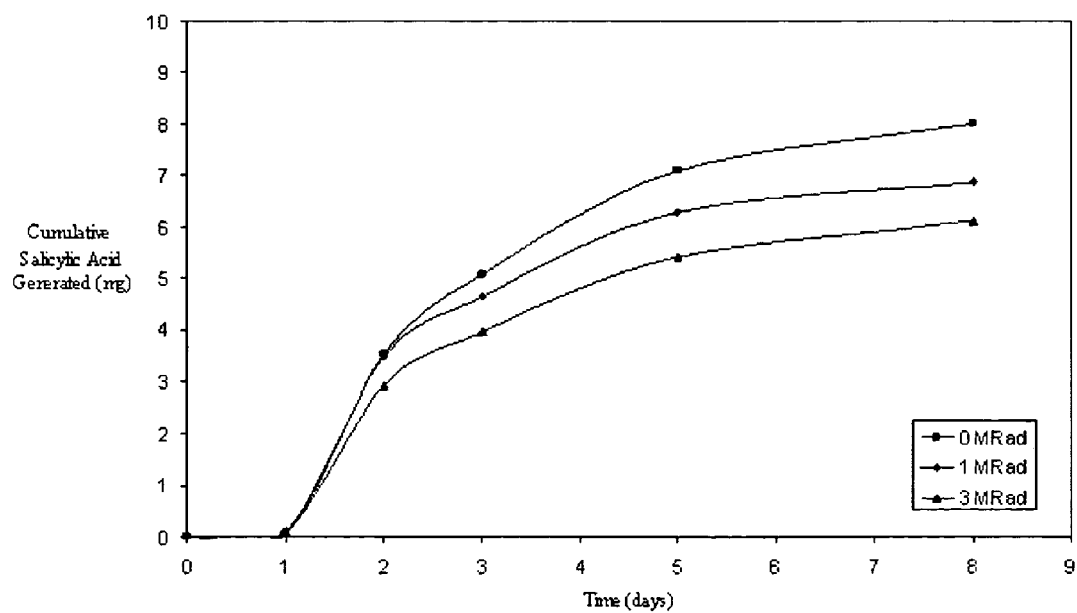
FIG. 13B is a graph showing the cumulative mass of salicylic acid generated by the bioerosion of a coating of untreated and E beam-treated polymerized salicylic acid.

Data obtained for 316L stainless steel coupons with a 30 mm×20 mm×~5 µm thick coating of therapeutic polymer of PX510, PX261, or PX721, untreated, treated with 0, 1, or 3 MRad of E beam, or treated with 25-35 KGys of gamma irradiation. FIG. 12 presents data for changes in molecular weight (as measured by gel permeation chromatography) and hardness, flexibility, and adhesion (as described in Example 1) for treated coatings of polymerized salicylic acid relative to similar untreated coatings. FIG. 13 presents data for the generation of salicylic acid from untreated and E beam-treated coatings into an incubating solution of pH 7.4 phosphate buffered saline (PBS) maintained at 37° C., expressed as either the mass of salicylic acid generated per day (FIG. 13*a*) or the cumulative mass of salicylic acid generated (FIG. 13*b*). These data demonstrate that there is no substantial change in the physical properties or rates or duration of generation of salicylic acid from coatings of polymerized salicylic acid composed of dicarboxylic acid linkers with a range of molecular weight upon treatment with E beam.

Example 5

Figure 14:
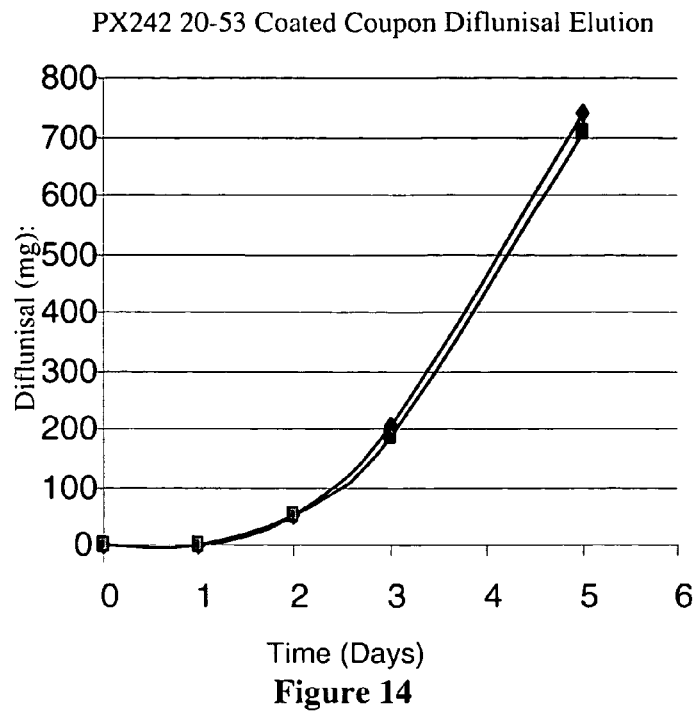
FIG. 14 is a graph showing poly-diflunisal anhydride polymer (PX24220-53) and diflunisal elution in μg overtime (days). Diamonds and square represent two replicates of poly-diflunisal coated coupons.
Figure 15:
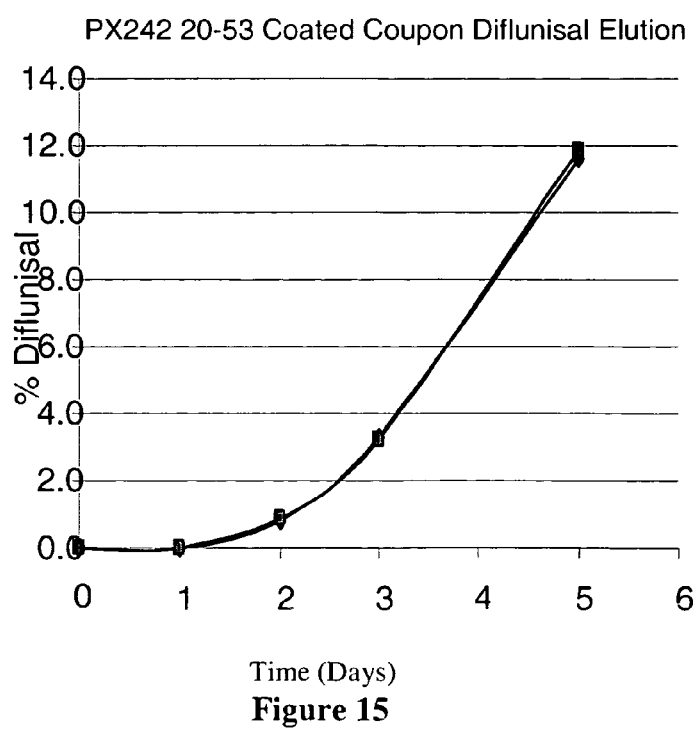
FIG. 15 is a graph showing poly-diflunisal anhydride polymer (PX24220-53) and diflunisal elution in percent diflunisal over time (days). Diamonds and square represent two replicates of poly-diflunisal coated coupons.
Figure 16:
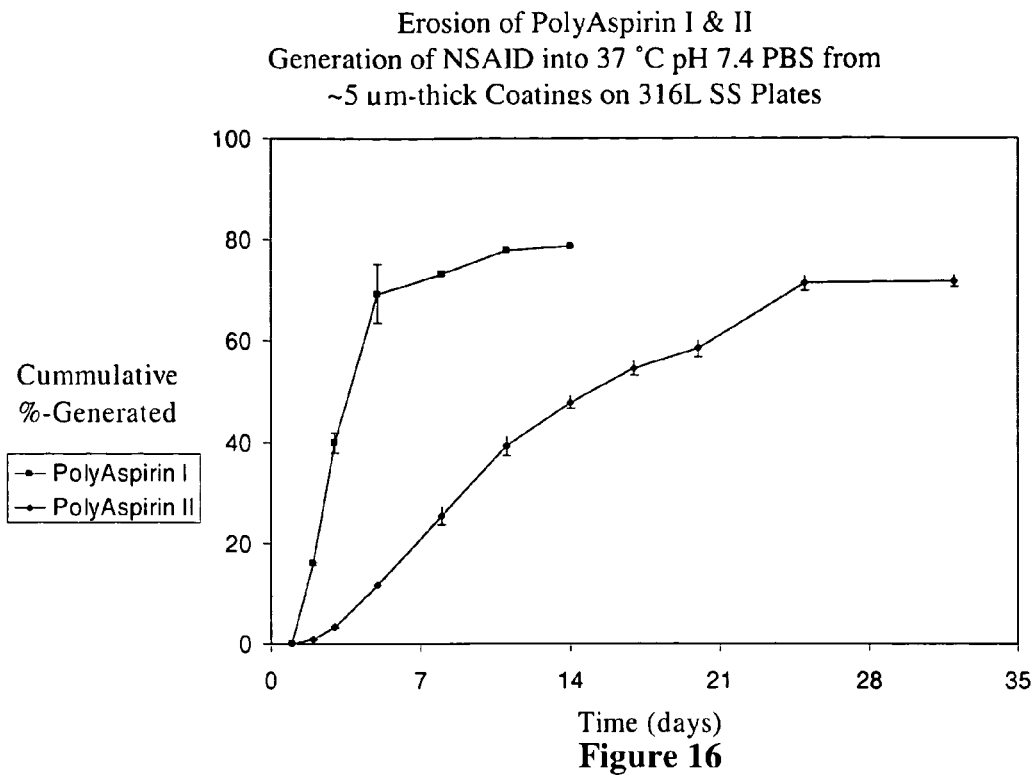
FIG. 16 is a graph showing the erosion of poly-salicylic anhydride polymer (PolyAspirin I) and of poly-diflunisal anhydride polymer (PolyAspirin II) in cumulative percent generated over time.
Figure 17:
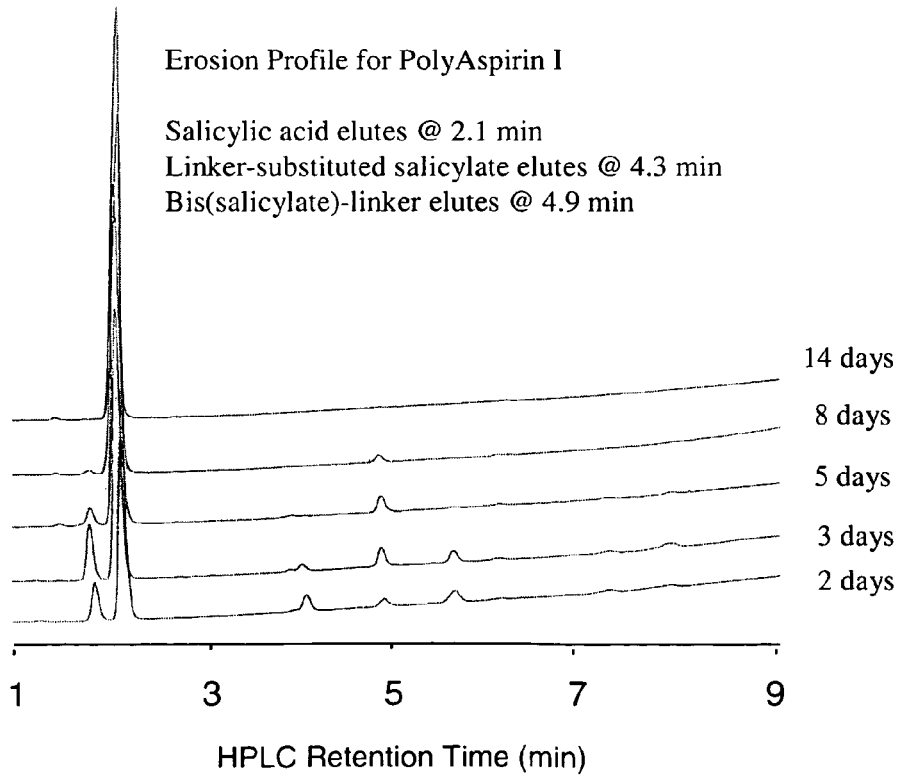
FIG. 17 is a graph showing the erosion profile for a poly-salicylic anhydride polymer (PolyAspirin I).
Figure 18:
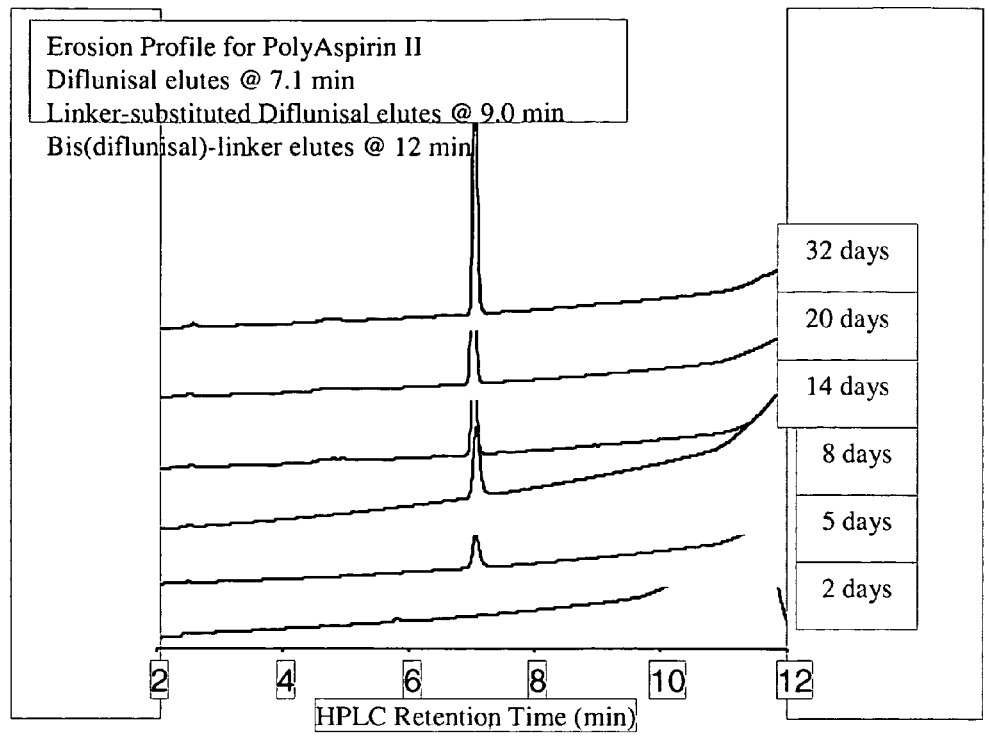
FIG. 18 is a graph showing the erosion profile for a poly-diflunisal anhydride polymer (PolyAspirin II).
Figure 19:
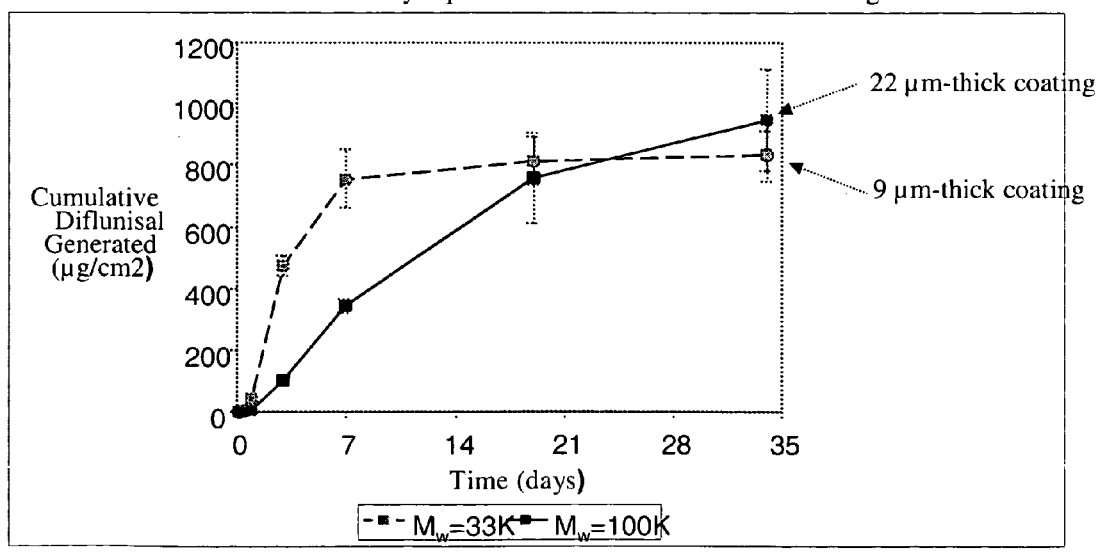
FIG. 19 is a graph showing the effect of molecular weight on erosion of poly-diflunisal anhydride polymers (PolyAspirin II) of different molecular weights in cumulative diflunisal generated over time.
Figure 20:
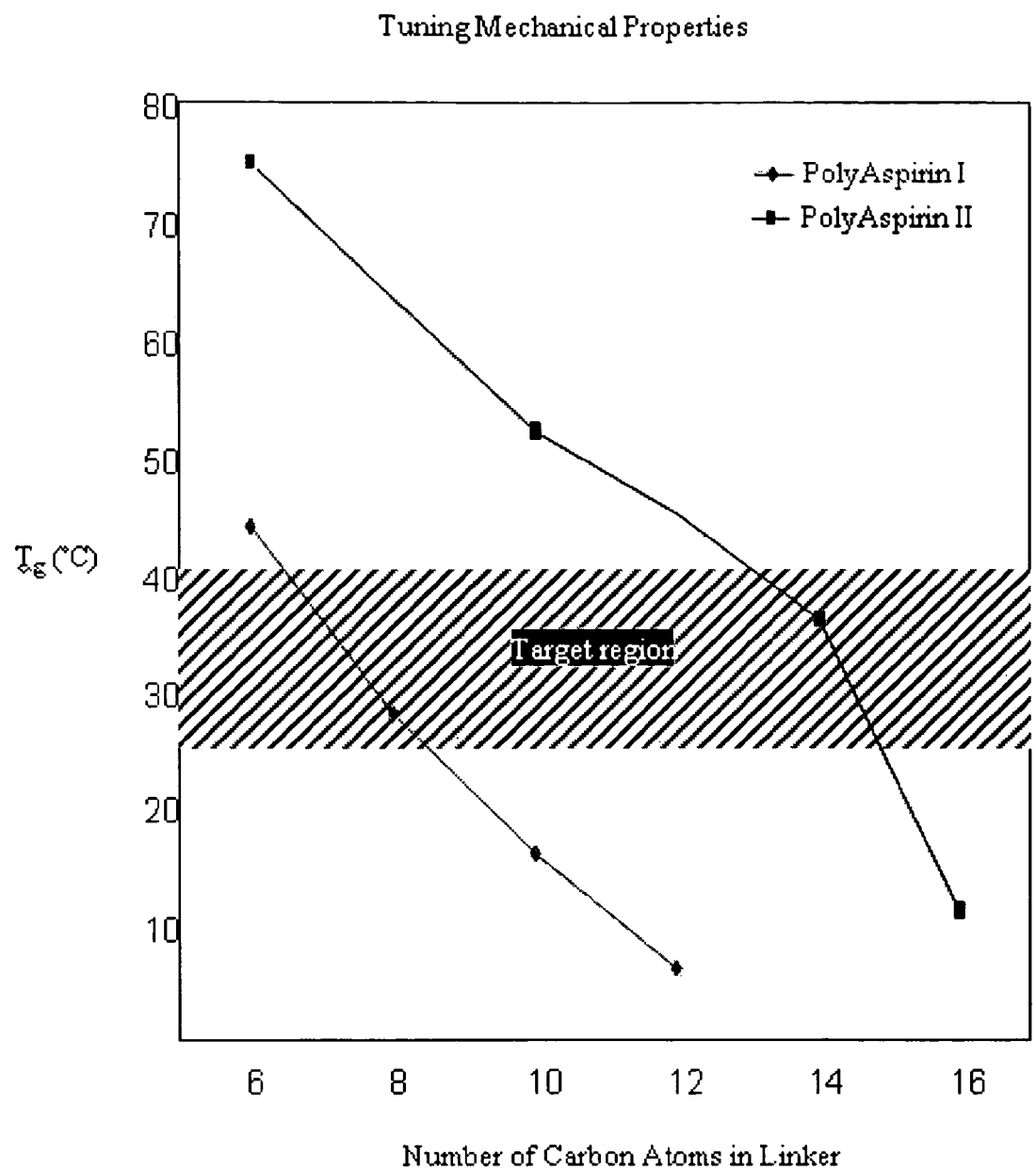
FIG. 20 is a graph showing the tuning mechanical properties of poly-salicylic anhydride polymer (PolyAspirin I) and of poly-diflunisal anhydride polymer (PolyAspirin II) in $T_g$(° C.) over "Number of Carbon Atoms in Linker."
Figure 24:
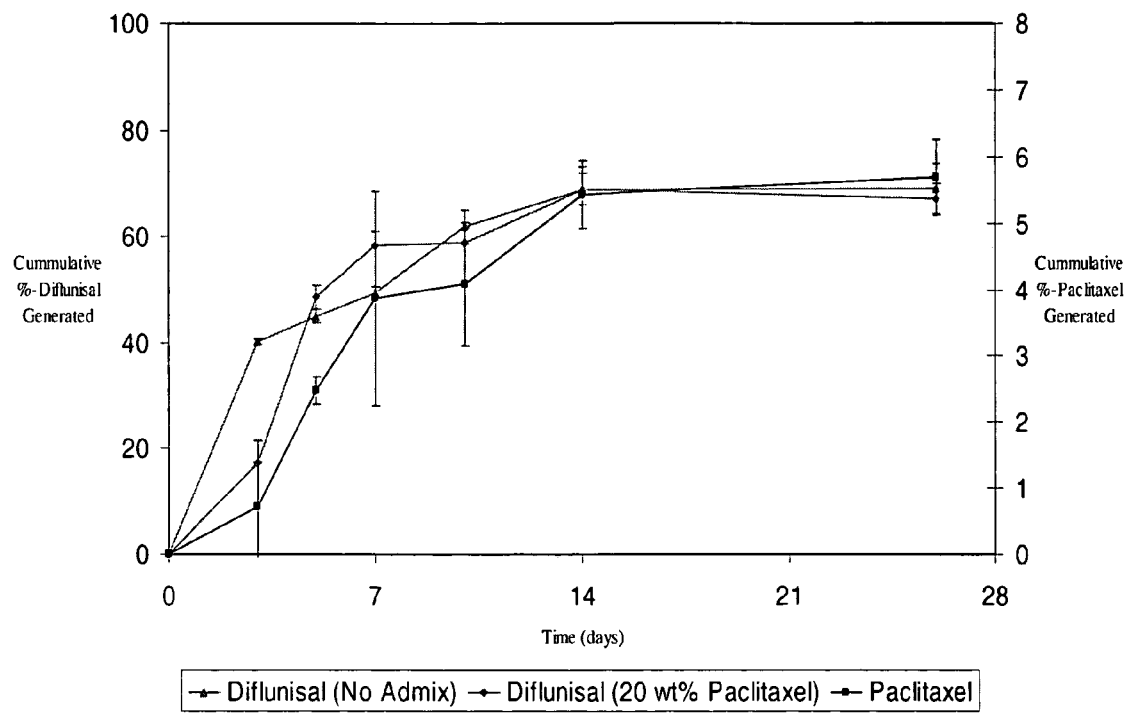
FIG. 24 is a graph showing the erosion of poly-diflunisal anhydride polymer (PolyAspirin II) and poly-diflunisal anhydride polymer admixed with paclitaxel in cumulative percent diflunisal generated and cumulative percent paclitaxel generated over time.
Figure 25:
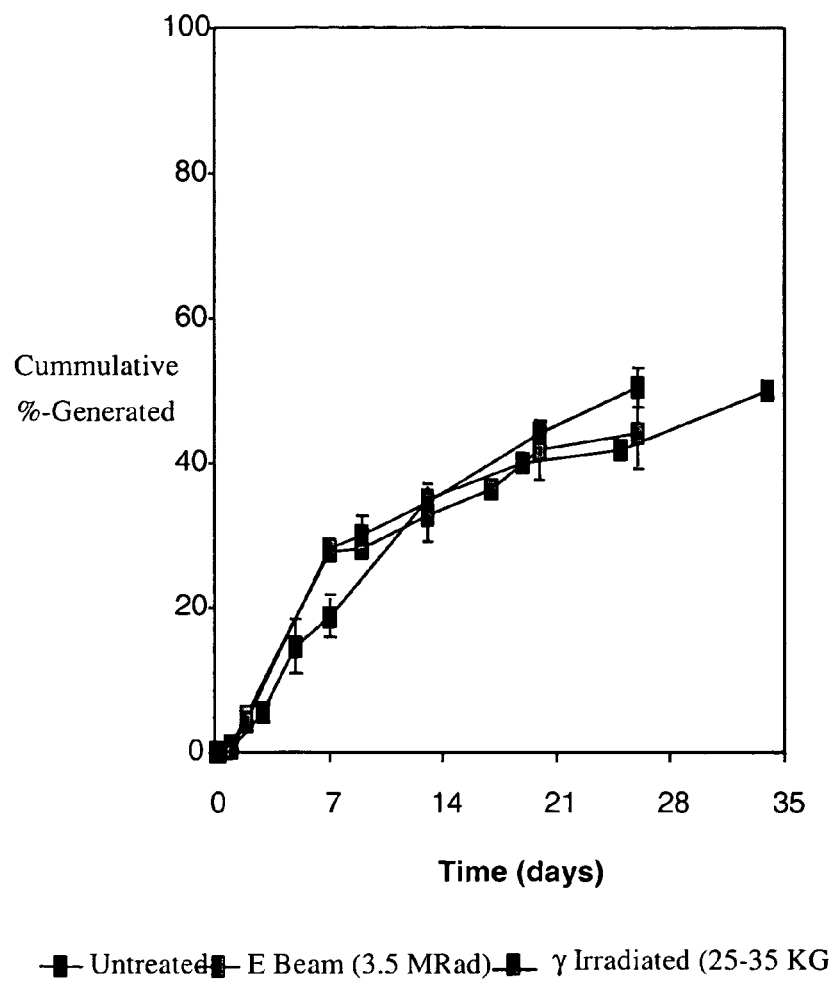
FIG. 25 is a graph showing the erosion of untreated or sterilized poly-diflunisal anhydride polymer (PolyAspirin II) in cumulative percent generated over time.

FIGS. 14 and 15 show the degradation rate of poly-diflunisal-sebacic acid anhydride coated onto steel coupons. Poly-salicylic acid has a 5 fold faster degradation/drug generation rate than poly-diflunisal when both polymers have the same linkers. Poly-salicylic acid anhydride polymers will be more useful for applications where a more rapid release of admixed drug or short term therapy is needed, while poly-diflunisal anhydride polymers with the same linkers produce a product that will last longer and be more potent, enabling the same thickness film to provide longer lasting therapeutic benefit.

Example 6

Swine Stent Model

A total of 8 stents were implanted in the coronary arteries of 3 miniswine for 28 days. The stent implants were Polymerix [nicknamed MARGI] 15 mm in length with an unexpanded diameter of 1.6 mm. Each stent had a nominal coating of 1 mg of PolySAID II (a polymer of diflunisal). Treatment stents containing sirolimus or paclitaxel had 20% added drug by weight representing 800 mg of polymer and 200 mg drug; control stents were with polymer alone.

Stent Matrix for Light Microscopy (n=8)

|  |  | Artery | | | Date of |
| --- | --- | --- | --- | --- | --- |
| Animal # | CVPath# | LAD | LCx | RCA | Arrival |
| 2P 315 | 10424 | X (CTL) | X (PXL) | X (SR) | Jan. 31, 2003 |
| 2P 316 | 10425 | X (SR) |  | X (PXL) | Jan. 31, 2003 |
| 2P 339 | 10426 | X (PXL) | X (SR) | X (CTL) | Jan. 31, 2003 |

CTL = control,
PXL = paclitaxel,
SR = sirolimus,

All stents were processed for light microscopic evaluation. Before processing, the vessels and hearts were x-rayed to locate and assess stent placement. For processing, the stented vessel segments were dehydrated in a graded series of ethanol and embedded in methylmethacrylate plastic. After polymerization, two to three millimeter sections were sawed from the proximal, mid and distal portions of each stent. Sections from the stents were cut on a rotary microtome at four to five microns, mounted and stained with hematoxylin and eosin and elastic Van Gieson stains. All sections were examined by light microscopy for the presence of inflammation, thrombus, neointimal formation, vessel wall injury and potential localized toxic effects associated with drug-coated stents.

Myocardial sections were taken from the anterior, lateral, posterior and septal walls of the left ventricle distal to the stent and from the apical region of the left ventricle. To determine localized affects of the polymer and/or drug, the myocardium was also sampled beneath the area of stent placement. All sections were cut at 4-6 microns; mounted and stained with hematoxylin and eosin and examined for the presence of infarct, thromboembolus and inflammation.

A vessel injury score was calculated according to the Schwartz method. The cross-sectional areas (external elastic lamina [EEL], internal elastic lamina [IEL] and lumen) of each section were measured with digital morphometry. Neointimal thickness was measured as the distance from the inner surface of each stent strut to the luminal border. Percent area stenosis was calculated with the formula [(Neointimal Area/IEL Area)×100]. Ordinal data was also collected for fibrin deposition and inflammation and hemorrhage around the stent struts and percent endothelialization of the lumen surfaces. Values are expressed as mean±SD. Mean variables were compared between the groups with the use of ANOVA with Fishers Post Hoc Correction for analysis of the data. A value of $P \leq 0.05$ was considered statistically significant.

TABLE 1

Morphometric comparison of cross-sectional vessel areas and neointimal response of Drug-Coated and Control Groups.

| Treatment Group | EEL Area mm2 | IEL Area mm2 | Lumen Area mm2 | Intimal Area mm2 | Stenosis (%) | Intimal Thick. mm | Injury Score |
|---|---|---|---|---|---|---|---|
| Control PolyNSAID II (n = 2) | 5.75 ± 0.21 | 4.60 ± 0.12 | 3.03 ± 0.21 | 1.56 ± 0.38 | 33.82 ± 7.1 | 0.22 ± 0.05 | 0.31 ± 0.14 |
| Sirolimus (n = 3) | 6.07 ± 0.61 | 4.78 ± 0.39 | 3.81 ± 0.62 | 0.96 ± .50 | 20.31 ± 10.1 | 0.10 ± 0.05 | 0.45 ± 0.69 |
| Paclitaxel (n = 3) | 8.41 ± 2.95 | 6.84 ± 2.56 | 4.70 ± 0.64 | 2.14 ± 2.10 | 27.21 ± 17.11 | 0.05 ± 0.01 | 0.35 ± 0.48 |
| P-value C vs SR | 0.31 | 0.61 | 0.20 | 0.23 | 0.20 | 0.007 | 0.80 |
| C vs PXL | 0.55 | 0.32 | 0.04 | 0.74 | 0.65 | 0.08 | 0.91 |

Values are expressed as the means ± SE.
The number in parentheses correspond the number of stents.

TABLE 2

Morphometric comparison of drug effects on vessel healing compared to control stents

| Treatment Group | % Struts (Fibrin) | % Struts Hemorrhage | Ave Inflammation score | % Struts with underlying medial necrosis |
|---|---|---|---|---|
| Control PolyNSAID II (n = 2) | 4.16 ± 5.89 | 8.33 ± 11.79 | 1.5 ± 0.71 | 0 |
| Sirolimus (n = 3) | 57.78 ± 43.47 | 28.33 ± 30.14 | 2.3 ± 0.58 | 0.68 ± 0.68 |
| Paclitaxel (n=) | 100 | 100 | 2.0 | 8.67 ± 3.51 |
| P-Value C vs SR | 0.20 | 0.45 | 0.24 | 0.49 |
| C vs PXL | <0.0001 | 0.007 | 0.27 | 0.04 |

Values are expressed as the mean ± SE. The number in parentheses correspond the number or stents.

Values are expressed as the means±SE. The number in parentheses correspond the number or stents.

X-rays of the vessels show good tracking of the stents in the vessels.

All stented vessels show patent lumens and complete neointimal incorporation of the stents. Control stents were widely expanded and struts well apposed to the vessel walls while malapposition was noted with paclitaxel-eluting stents. Neointimal growth varied in thickness over the struts and was both eccentric and concentric in location. In control stents, the neointima is well organized and consists of circumferentially arranged smooth muscle cells around the lumen. In contrast, drug-eluting stent displayed varying degrees of delayed healing. In particular paclitaxel-eluting stents showed malapposition with underlying medial necrosis with extensive accumulation of fibrin, hemorrhage, and inflammatory cells around the stent struts. Stents coated with sirolimus were generally showed less neointimal growth and were more healed than those coated with paclitaxel. There was; however, still persistent fibrin deposition, hemorrhage and inflammatory cells. The polymer coating was still present by histology.

The results are depicted in FIGS. 29-36.

Example 7

Rabbit Stent Model

Male New Zealand White rabbits (n=24) were randomized to received 48 stents as follows:
1. Bare=24
2. PolyAspirin I (thin-coating)=2
3. PolyAspirin I (thick-coating)=11
4. PolyAspirin II=11

The stents were harvested at 7 and 28 days.

| Stent Matrix (7 day animals) | | Stent Matrix (28 day animals) | |
| --- | --- | --- | --- |
| Stent Type | No Stent | Stent Type | No Stent |
| Bare | 8 | Bare | 16 |
| PolyAspirin I (thin-coating) | 2 | PolyAspirin I (thin-coating) | 0 |
| PolyAspirin I (thick-coating) | 3 | PolyAspirin I (thick-coating) | 8 |
| PolyAspirin II | 3 | PolyAspirin II | 8 |

Stent Procedure:

A one-inch midline neck incision was created using a size 10 scalpel blade. With blunt dissection techniques, the muscles underneath the fascia on the left side of the trachea were exposed. The muscles were separated along their connective tissue junction, and the carotid artery exposed. The artery was then separated from the vagus nerve. Proximal and distal suture loops were placed on the artery to allow for retraction. A No. 5F Cordis sheath was inserted into the left common carotid artery. Heparin (150 IU/kg) was administered intra-arterially via the sheath. A 5F Cook catheter was placed in the descending aorta (via the sheath) just below the diaphragm. Renograffin was then injected (1-2 ml) over a 2 second period to obtain a control angiogram of the distal aorta and both iliac arteries. The Cook catheter was removed.

Both iliac arteries were injured by endothelial denudation prior to stent delivery. A balloon catheter was placed in the distal iliac artery, using standard fluoroscopy methods, and inflated to 4 ATM. The catheter was then withdrawn proximally in its inflated state a distance of approximately 1.5 to 2 cm. The balloon was deflated, repositioned in the distal iliac and vessel denudation was repeated at a higher pressure of 6 ATM over the same segment of vessel initially denuded.

Each rabbit iliac artery received a PolyAspirin I (thin or thick coating) or PolyAspirin II-coated stent (15 mm in length) and a control stainless steel stent (of identical design) in the contralateral iliac; all stents were provided by the sponser. Stents arrived packaged in individually sealed vials and stored at −4° C. and were manually crimped on a 3.0 mm diameter angioplasty balloon before implantation. The stent catheter is delivered to each iliac artery over a guide wire using fluoroscopic guidance. Stents are deployed by inflation to 6 atmospheres for 30 seconds to securely deploy the prosthesis within the vessel. Following stent deployment, angiography (same procedure as above) is performed to document stent patentcy. The proximal left carotid arteryis then ligated, the muscle and fascia sutured with a 3.0 dexon absorbable suture, and the neck incision closed with a 4.0 silk non-absorbable suture. At euthanasia, a 5F sheath is placed in the right carotid artery and jugular vein, and an angiogram is repeated. The stented iliac arteries and distal aorta will be taken out and processed for light microscopy.

Euthanasia, Fixation, and Light Microscopy

Before euthanasia, animals received bromodeoxyuridine (BrdU) for monitoring cell proliferation as described previously by our laboratory (Farb A, Tang A L, Shroff S, Sweet W, Virmani R. Neointimal responses 3 months after (32)P beta-emitting stent placement. Int J Radiat Oncol Biol Phys. 2000 Oct. 1; 48(3):889-98). Animals were anesthetized as above (ketamine IM, isoflurane via facemask and ventilation with 100% oxygen; anesthesia was maintained with inhaled isoflurane). A 5F sheath was placed in the right carotid artery, and a pre-euthanasia angiogram of the iliac arteries was performed. A 5F sheath was inserted into the jugular vein. Immediately prior to perfusion-fixation, rabbits received 1000 units of intravenous heparin. Euthanasia was accomplished with an injection of 1 ml of Beuthanasia given under deep anesthesia. The arterial tree was perfused at 100 mm Hg with lactated Ringer's until the perfusate from the jugular vein was clear of blood. The arterial tree was then perfused at 100 mm Hg with 10% formalin for 15 minutes. The distal aorta to the proximal femoral arteries was excised and cleaned of periadventitial tissue. Arteries were radiographed using a Faxitron. The stents were then processed for plastic embedding (see below).

Light Microscopy Procedures

For light microscopy, the stented vessel segments were dehydrated in a graded series of ethanol and embedded in methylmethacrylate plastic. After polymerimerization, two to three mm sections were sawed from the proximal, mid and distal portions of each single stent. Sections from the stents were cut on a rotary microtome at 6 µm, mounted and stained by hematoxylin and eosin and Movat Pentachrome. All sections were examined by ligh microscopy for the presence of inflammation, thrombus, and neointimal formation and vessel wall injury.

Histomorphometric Analysis

Microscopic images of plastic embedded Movat pentachrome stained sections were captured on a Macintosh 8100/80 using a Sony CCD video camera mounted on an Olympus microscope. The area encompassed by the external (EEL) and internal elastic lamina (IEL) and lumen were measured using morphometry software (IP labs, Signal Analytics, Vienna, Va.). The intima was measured at and between stent struts (mean intimal thickness is the average of these two measurements). The media and adventitia thickness were determined between stent struts. Subtracting the lumen from IEL or the IEL from EEL, respectively, derived the intimal and medial area. Percent luminal stenosis was calculated using the formula [1−(lumen/IEL)]×100. To compare neointimal organization and healing, ordinal data were collected on the proximal section from each stent and included fibrin deposition, granuloma and giant cell reaction, medial necrosis and hemorrhage around the stent struts and were expressed as a percentage of the total number of struts in each section. An overall inflammation and fibrin value was also scored for the proximal section (value 0 for no inflammation/fibrin to a value of 3 representing marked inflammation/fibrin. Endothelial coverage was semi-quantified and expressed as the percentage of the lumen circumference covered by endothelium. Each coated stent was analyzed against the bare control stents implanted in the same animals. Unpaired t-tests were used to calculate the significance of differences between variable means of the treatment groups. A value of $P \leq 0.05$ was considered statistically significant.

Immunohistochemisty

Tissue sections in methyl methacrylate were deplasticized in xylenes, methyl acetate and acetone before staining. Heating the sections with steam for 20 min was performed for antigen recovery. The sections were preincubated with 0.3% hydrogen peroxide and Protein Block Serum-Free (X0909, Dako Corp, Calif.) and incubated overnight at 4° C. at room temperature with a monoclonal antibody against α-smooth muscle actin (1:1000 dilution, Dako). Identification of BrdU positive nuclei was identified immunohistochemically using a mouse monoclonal anti-BrdU antibody (1:400 dilution, DAKO Co., Carpinteria, Calif.) after incubating tissue sections in 2 N HCl for 15 minutes at 37° C. Systemic distribution of BrdU was confirmed by intense staining of intestinal crypt cell in all animals receiving the agent. Smooth muscle cells and macrophage were identified using monoclonal antibodies directed against α-SM actin (1:1000 dilution, Sigma Chemical Co. and RAM 11 (1:200 dilution Dako) at 4° C. overnight. Primary antibody labeling was performed using a biotinylated link antibody, directed against mouse using a peroxidase based LSAB kit (Dako). Positive staining (rose reaction product) was visualized using a 3-amino-9-ethylcarbazole (AEC) substrate-chromogen system. After immunostaining, the sections were counterstained with Gill's hematoxylin, washed and mounted in aqueous media.

Stent Deployment

Pre-stent balloon arterial dilatation was evident by angiography. Bilateral iliac stent deployment in the rabbit was accomplished successfully. The catheters tracked well and were easily placed in the iliac arteries along with the stents. All arteries were widely patent at follow-up angiography at 7 or 28 days after implant; there was no evidence of thrombosis. Further, X-ray analysis of stents showed good expansion and stent struts were well opposed to the arterial wall.

Quantitative Findings

Stents Harvested at 7 Days

TABLE 2

Morphometric comparison of cross-sectional vessel areas and neointimal responses of polymer-coated and control stents deployed in rabbit iliac arteries for 7 days.

| Group | ADV THK (mm) | MEDIA THK (mm) | INTIMA THK (mm) | LUMEN AREA (mm$^2$) | IEL AREA (mm$^2$) | EEL AREA (mm$^2$) |
|---|---|---|---|---|---|---|
| Bare stent (n = 8) | 0.036 ± 0.001 | 0.047 ± 0.003 | 0.020 ± 0.003 | 4.89 ± 0.09 | 5.34 ± 0.09 | 5.69 ± 0.09 |
| PolyAsp I (n = 2) (thin) | 0.036 ± 0.003 | 0.048 ± 0.008 | 0.013 ± 0.003 | 4.83 ± 0.06 | 5.31 ± 0.12 | 5.65 ± 0.15 |
| PolyAsp I (n = 9) | 0.031 ± 0.004 | 0.051 ± 0.009 | 0.015 ± 0.003 | 4.83 ± 0.06 | 5.23 ± 0.10 | 5.54 ± 0.21 |
| PolyAsp II (n = 8) | 0.033 ± 0.002 | 0.045 ± 0.006 | 0.015 ± 0.006 | 4.76 ± 0.36 | 5.19 ± 0.38 | 5.36 ± 0.38 |
| P value | ns | ns | ns | ns | ns | ns |

| Group | STENT AREA (mm$^2$) | ADV AREA (mm$^2$) | MEDIAL AREA (mm$^2$) | INTIMAL AREA (mm$^2$) | STENOSIS (%) | Injury Score |
|---|---|---|---|---|---|---|
| Bare stent (n = 17) | 5.37 ± 0.09 | 5.90 ± 0.89 | 0.34 ± 0.01 | 0.46 ± 0.03 | 8.45 ± 0.53 | 0.035 ± 0.01 |
| PolyAsp I (n = 2) (thin) | 5.32 ± 0.11 | 5.87 ± 0.12 | 0.34 ± 0.04 | 0.38 ± 0.05 | 7.15 ± 0.74 | 0.070 ± 0.07 |
| PolyAsp I (n = 9) | 5.23 ± 0.13 | 5.76 ± 0.13 | 0.33 ± 0.04 | 0.39 ± 0.06 | 7.37 ± 1.01 | 0.19 ± 0.19 |
| PolyAsp II (n = 8) | 5.23 ± 0.37 | 5.71 ± 0.38 | 0.34 ± 0.03 | 0.43 ± 0.04 | 8.43 ± 1.30 | 0.056 ± 0.03 |
| P value | ns | ns | ns | ns | ns | ns |

The values are reported as the means ± SE for 3 sections (proximal, middle, and distal) from each stent.
Abbreviations:
ADV = adventitia;
IEL = internal elastic lamina;
EEL = external elastic lamina.
The numbers in parenthesis correspond to the number of stents.

TABLE 3

Morphometric comparison of polymer effects on vessel healing compared with control stents deployed in rabbit iliac arteries for 7 days.

| Group | Struts with Fibrin (%) | Fibrin Score | Endothelium (%) | RBCS (%) | Giant Cells (%) | Inflamm. Score |
|---|---|---|---|---|---|---|
| Bare stent (n = 8) | 77.92 ± 12.16 | 1.75 ± 0.25 | 94.79 ± 2.19 | 52.92 ± 13.10 | 14.58 ± 4.92 | 1.25 ± 0.16 |
| PolyAsp I (Thick) (n = 3) | 75.00 ± 14.43 | 2.00 ± 0.00 | 75.00 ± 16.67 | 47.22 ± 19.44 | 16.67 ± 8.33 | 2.68 ± 0.15 |

TABLE 3-continued

Morphometric comparison of polymer effects on vessel healing compared with control stents deployed in rabbit iliac arteries for 7 days.

| Group | Struts with Fibrin (%) | Fibirn Score | Endothelium (%) | RBCS (%) | Giant Cells (%) | Inflamm. Score |
|---|---|---|---|---|---|---|
| PolyAsp I Thin (n = 2) | 70.83 ± 20.83 | 2 ± 0.00 | 87.5 ± 4.17 | 50.00 ± 0.00 | 4.17 ± 4.17 | 1.00 ± 0.00 |
| PolyAsp II (n = 3) | 72.22 ± 20.03 | 1.67 ± 0.33 | 86.11 ± 13.89 | 50.00 ± 14.43 | 19.44 ± 2.78 | 1.33 ± 0.33 |
| P value | ns | ns | ns | ns | PII vs PI (thin) P = 0.048 | ns |

The values are reported as the means ± SE for proximal sections of each stent.
Inflamm. = inflammation score.

Stents Harvested at 28 Days

TABLE 4

Morphometric analysis of aspirin-polymer stents deployed in rabbit iliac arteries for 28 days.

| Group | ADV THK (mm) | MEDIA THK (mm) | INTIMA THK (mm) | LUMEN AREA (mm$^2$) | IEL AREA (mm$^2$) | EEL AREA (mm$^2$) |
|---|---|---|---|---|---|---|
| Bare stent (n = 16) | 0.040 ± 0.002 | 0.050 ± 0.004 | 0.093 ± 0.007 | 4.15 ± 0.15 | 5.17 ± 0.19 | 5.49 ± 0.20 |
| PolyAsp I (n = 9) | 0.0041 ± 0.004 | 0.050 ± 0.005 | 0.103 ± 0.005 | 4.12 ± 0.22 | 5.20 ± 0.26 | 5.51 ± 0.28 |
| PolyAsp II (n = 8) | 0.37 ± 0.001 | 0.044 ± 0.003 | 0.075 ± 0.006 | 4.15 ± 0.30 | 5.04 ± 0.03 | 5.34 ± 0.36 |
| P value | ns | ns | PI vs PII P = 0.002 | ns | ns | ns |

| Group | STENT AREA (mm$^2$) | ADV AREA (mm$^2$) | MEDIAL AREA (mm$^2$) | INTIMAL AREA (mm$^2$) | STENOSIS (%) | Injury Score |
|---|---|---|---|---|---|---|
| Bare stent (n = 16) | 5.21 ± 0.19 | 5.70 ± 0.20 | 0.32 ± 0.02 | 1.02 ± 0.06 | 19.6 ± 0.84 | 0.108 ± 0.025 |
| PolyAsp I (n = 9) | 5.23 ± 0.26 | 5.71 ± 0.29 | 0.31 ± 0.03 | 1.08 ± 0.08 | 20.8 ± 1.30 | 0.124 ± 0.065 |
| PolyAsp II (n = 8) | 5.07 ± 0.34 | 5.55 ± 0.36 | 0.30 ± 0.02 | 0.89 ± 0.07 | 17.8 ± 0.73 | 0.035 ± 0.028 |
| P value | ns | ns | ns | ns | PI vs PII P = 0.056 | ns |

The values are reported as the means ± SE for 3 sections (proximal, middle, and distal) from each stent.
Abbreviations:
ADV = adventitia;
IEL = internal elastic lamina;
EEL = external elastic lamina.
The numbers in parenthesis correspond to the nimber of stents.

TABLE 5

Morphometric comparison of polymer effects on vessel healing compared with control stents deployed in rabbit iliac arteries for 28days.

| Group | Struts with Fibirn (%) | Fibirn Score | Endothelium (%) | RBCS (%) | Giant Cells (%) | Inflamm. Score |
|---|---|---|---|---|---|---|
| Bare stent (n = 16) | 13.90 ± 4.45 | 0.56 ± 0.13 | 100 | 4.36 ± 2.25 | 22.28 ± 5.45 | 0.56 ± 0.16 |
| PolyAsp I (n = 8) | 18.75 ± 11.97 | 0.63 ± 0.26 | 92.71 ± 7.30 | 0 | 45.83 ± 7.39 | 1.00 ± 0.27 |

TABLE 5-continued

Morphometric comparison of polymer effects on vessel healing compared with control stents deployed in rabbit iliac arteries for 28days.

| Group | Struts with Fibrin (%) | Fibirn Score | Endothelium (%) | RBCS (%) | Giant Cells (%) | Inflamm. Score |
|---|---|---|---|---|---|---|
| PolyAsp II (n = 8) | 22.92 ± 7.84 | 0.88 ± 0.23 | 100 | 5.21 ± 2.19 | 38.83 ± 10.15 | 1.38 ± 0.26 |
| P value | ns | ns | ns | PI vs PII P = 0.032 | PI vs Bare P = 0.019 | PII vs Bare P = 0.01 |

The values are reported as the means ± SE for proximal sections of each stent.
Inflamm. = inflammation score.

BrdU Counts

The following tables summarize the number of BrdU positive nuclei in the various polymer-coated stents assessed at 7 and 28 days. Four high power fields were selected at random from the neointima of the mid section from each stent. The total numbers of cells within each region of interest were counted; Brdu positive cells and are expressed per unit area ($mm^2$) or as a percentage of total cell numbers (ie., BrdU index).

TABLE 6

Analysis of cell proliferation in polymer and control stents deployed in rabbit iliac arteries for 7 days.

| Group | Total Cells per ($mm^2$) | Brdu+ Cells ($mm^2$) | BrdU index |
|---|---|---|---|
| Bare stent (n = 6) | 3336 ± 676 | 1859 ± 459 | 54.5 ± 4.9 |
| PolyAsp I (Thick) (n = 3) | 4220 ± 766 | 2231 ± 935 | 48.1 ± 14.1 |
| PolyAsp I Thin (n = 2) | 4113 ± 984 | 1227 ± 147 | 16.1 ± 11.4 |
| PolyAsp II (n = 3) | 2978 ± 1194 | 960 ± 289 | 40.6 ± 10.5 |
| P value | ns | ns | PI (thin) vs bare = 0.0862 |

TABLE 7

Analysis of cell proliferation in polymer and control stents deployed in rabbit iliac arteries for 28 days.

| Group | Total Cells per ($mm^2$) | Brdu+ Cells ($mm^2$) | BrdU index |
|---|---|---|---|
| Bare stent (n = 8) | 5556 ± 1910 | 49 ± 13 | 1.5 ± 0.4 |
| PolyAsp I (Thick) (n = 3) | 5284 ± 2337 | 84 ± 38 | 1.6 ± 0.4 |
| PolyAsp II (n = 3) | 3497 ± 433 | 50 ± 11 | 1.6 ± 0.4 |
| P value | ns | ns | ns |

All sections from the stented vessels showed widely patent lumens and for the majority good stent strut apposition to the arterial wall; occasional stent struts showed malapposition. Most stents are fully covered with a mildly thickened layer of organizing thrombus composed mostly of fibrin, acute and chronic inflammatory cells, extravasated red blood cells, and early smooth muscle cell infiltration. The inflammatory cell infiltration of the thrombus consisted mainly of mononuclear macrophages and multiple giant cell reaction around most of the struts. There was no significant difference in intimal thickness or the percentage of stenosis among groups (Table 2). The native lumen surfaces are endothelialized between the struts with occasional stent struts showing an absence of endothelium. There are no medial lacerations, fractures or rupture of the external elastic lamina as well as no effects of the polymer coating on the medial layer. The polymer coatings (PolyAspirin I and U) are not easily apparent in stents harvested at 7 days.

All sections from the stented vessels at 28 days showed widely patent lumens with good stent strut apposition to the arterial wall. Most stents are fully covered with a thickened layer of smooth muscle cells, proteoglycans and collagen; occasion fibrin deposition around struts however is noted. The inflammatory cell infiltration of the consisted mainly of mononuclear macrophages and multiple giant cell reaction around stent struts.

Overall intimal thickness and the percentage of stenosis was significantly less in PolyAspirin II versus PolyAspirin I stents (see Table 4); no statistical differences however, were found, when coated stents were compared with bare control stents. The native lumen surfaces showed near complete endothelization. There are no medial lacerations, fractures or rupture of the external elastic lamina as well as no effects of the polymer coating on the medial layer. The polymer coating PolyAspirin I was not apparent in stents harvested at 28 days. In contast, PolyAspirin II polymer was evident by histology as a thickened grayish staining around stent struts. In some sections, macrophage giant cells appear to contain the PolyAspirin II polymer (see micrographs below). The giant cells associated with PolyApirin I however, were smaller in appearance than with PolyAspirin II. Although the density of inflammatory infiltrate at 28 days is considerably less than 7 days, the giant cell reaction with both polymer stents is increased compared with the bare stents.

The results are depicted in FIGS. 37-43.

Example 8

Stent Coating

Solutions of polymer (PX184-55-80 (linear random C14 diflunisal); PX990-63-57 (80% C16 diflunisal/20% C14 diflunisal tetra); and PX727-63-25 (25% C8 salicylate tetra)) in chloroform were prepared (i.e., 20 mg of polymer in 1980 mg chloroform). The stents were spray coated with the solution, and allowed to air dry for 15 minutes. This spray coating process was repeated three times. The coated stents were vacuum dried at 30 degrees C. overnight.

The coated stents were observed under scanning electron microscopy (SEM), which are depicted in FIGS. 44-46. The results were positive in that there is about 700 micrograms of polymer on each stent, which corresponds to about a 5 micron thickness.

All publications, patents, and patent application documents are incorporated by reference herein in their entirety, as though individually incorporated by reference. The invention has been described with reference to various specific and preferred embodiments and techniques. However, it should be understood that many variations and modifications may be made while remaining within the spirit and scope of the invention.

The invention claimed is:

1. A medical device having at least one surface, comprising: 1) a polymer comprising salicylic acid incorporated into the polymer backbone on all or a portion of the surface, wherein the salicylic acid is disassociated from the polymer upon hydrolysis; and 2) a second active agent selected from paclitaxel and rapamycin that is dispersed within the polymer matrix of the polymer such that the second active agent is released upon degradation of the polymer.

2. The medical device of claim 1, wherein the medical device is a stent.

3. A stent of claim 2, comprising at least two or more surfaces.

4. A stent of claim 3, wherein all or a portion of the two or more surfaces are covered with the polymer.

5. A stent of claim 4, wherein the polymer covers all or a portion of the surface in a thickness of about 100 nm to 1 cm.

6. A stent of claim 4, wherein the polymer covers all or a portion of the surface in a thickness of about 0.5 μm to about 2.0 mm.

7. A stent of claim 4, wherein the active agent is disassociated from the polymer over a period of about 2 days to about 2 years.

8. The medical device of claim 1, wherein the polymer covers all or a portion of the surface in a thickness of about 100 nm to 1 cm.

9. The medical device of claim 1, wherein the polymer covers all or a portion of the surface in a thickness of about 0.5 μm to about 2.0 mm.

10. The medical device of claim 1, wherein the salicylic acid is disassociated from the polymer over a period of about 2 days to about 2 years.

11. A medical device of claim 1, wherein a third active agent is dispersed within the polymer matrix of the polymer such that the third active agent is released upon degradation of the polymer.

12. A medical device of claim 1, wherein a third active agent is appended to the polymer such that the third active agent is released under physiological conditions.

13. The device of claim 1 wherein the second agent is paclitaxel.

14. The device of claim 1 wherein the second agent is rapamycin.

* * * * *